(12) United States Patent
Palsson et al.

(10) Patent No.: US 8,229,673 B2
(45) Date of Patent: Jul. 24, 2012

(54) HUMAN METABOLIC MODELS AND METHODS

(75) Inventors: Bornhard O. Palsson, La Jolla, CA (US); Imandokht Famili, San Diego, CA (US); Markus W. Covert, San Diego, CA (US); Christophe H. Schilling, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 812 days.

(21) Appl. No.: 10/402,854

(22) Filed: Mar. 27, 2003

(65) Prior Publication Data

US 2004/0029149 A1 Feb. 12, 2004

Related U.S. Application Data

(60) Provisional application No. 60/368,588, filed on Mar. 29, 2002.

(51) Int. Cl.
*G01N 33/50* (2006.01)
*G01N 33/48* (2006.01)

(52) U.S. Cl. .......................................... 702/19; 702/20
(58) Field of Classification Search ........................ None
See application file for complete search history.

(56) References Cited

U.S. PATENT DOCUMENTS

| | | | |
|---|---|---|---|
| 5,273,038 A | 12/1993 | Beavin et al. | |
| 5,556,762 A | 9/1996 | Pinilla et al. | |
| 5,639,949 A | 6/1997 | Ligon et al. | |
| 5,689,633 A | 11/1997 | Cotner et al. | |
| 5,914,891 A | 6/1999 | Arkin et al. | |
| 5,930,154 A | 7/1999 | Thalhammer-Reyero | |
| 5,947,899 A | 9/1999 | Scollan et al. | |
| 5,980,096 A | 11/1999 | Thalhammer-Reyero | |
| 6,132,969 A | 10/2000 | Stoughton et al. | |
| 6,165,709 A | 12/2000 | Friend et al. | |
| 6,200,803 B1 | 3/2001 | Roberts | |
| 6,221,597 B1 | 4/2001 | Roberts | |
| 6,302,302 B1 | 10/2001 | Albisetti | |
| 6,329,139 B1 | 12/2001 | Nova et al. | |
| 6,351,712 B1 | 2/2002 | Stoughton et al. | |
| 6,370,478 B1 | 4/2002 | Stoughton et al. | |
| 6,379,964 B1 | 4/2002 | del Cardayre et al. | |
| 6,983,227 B1 * | 1/2006 | Thalhammer-Reyero | 703/2 |
| 7,127,379 B2 | 10/2006 | Palsson et al. | |
| 2002/0012939 A1 * | 1/2002 | Palsson | 435/6 |
| 2002/0051998 A1 | 5/2002 | Schmidt et al. | |
| 2002/0168654 A1 | 11/2002 | Maranas et al. | |
| 2003/0059792 A1 | 3/2003 | Palsson et al. | |
| 2003/0113761 A1 | 6/2003 | Tan et al. | |
| 2003/0224363 A1 | 12/2003 | Park et al. | |
| 2003/0233218 A1 | 12/2003 | Schilling | |
| 2004/0009466 A1 | 1/2004 | Maranas et al. | |
| 2004/0029149 A1 | 2/2004 | Palsson et al. | |

FOREIGN PATENT DOCUMENTS

| | | |
|---|---|---|
| WO | WO 92/09300 | 6/1992 |
| WO | WO 00/46405 | 8/2000 |
| WO | WO 01/36658 | 5/2001 |
| WO | WO 01/57775 A3 | 9/2001 |
| WO | WO 02/055995 | 7/2002 |
| WO | WO 02/061115 | 8/2002 |

OTHER PUBLICATIONS

Biaudet et al., "Micado—a network-oriented database for microbial genomes," Comput. Appl. Biosci., 13:431-438 (1997).
Bronk, J., "Human metabolism: functional diversity and integration," Addison Wesley Longman, Essex, England (1999).
Chvatal, _., "," *Linear Programming*, New York, W.H. Freeman and Co. (1983).
Covert et al., "Metabolic modeling of microbial strains in silico," *Trends in Biochemical Sciences*, 26:179-186 (2001).
Covert et al., "Regulation of gene expression in flux balance models metabolism," *J. Theor. Biol.*, 213:78-88 (2001).
Dauner and Sauer, "Stoichiometric growth model for riboflavin-producing *Bacillus subtilis*," *Biotechnol. Bioeng.*, 76:132-143 (2001).
Dauner et al., "*Bacillus subtilis* metabolism and energetics in carbon-limited and excess-carbon chemostat culture," *J. Bact.*, 183:7308-7317 (2001).
Dauner et al., "Metabolic flux analysis with a comprehensive isotopomer model in *Bacillus subtilis*," *Biotechnol. Bioeng*; ., 76:144-156 (2001).
DeCamp et al., "Protein engineering principles and practice," Ed. Cleland and Craik, Wiley-Liss, New York, pp. 467-505 (1996).
Devine, K., "The *Bacillus subtilis* genome project: aims and progress," *TIBTECH*, 13:210-216 (1995).
Devlin, T., "Textbook of biochemistry with clinical correlations," 4th ed., John Wiley and Sons, New York, NY (1997).

(Continued)

*Primary Examiner* — Jason Sims
(74) *Attorney, Agent, or Firm* — Jones Day

(57) ABSTRACT

The invention provides in silico models for determining the physiological function of human cells, including human skeletal muscle cells. The models include a data structure relating a plurality of *Homo sapiens* reactants to a plurality of *Homo sapiens* reactions, a constraint set for the plurality of *Homo sapiens* reactions, and commands for determining a distribution of flux through the reactions that is predictive of a *Homo sapiens* physiological function. A model of the invention can further include a gene database containing information characterizing the associated gene or genes. A regulated *Homo sapiens* reaction can be represented in a model of the invention by including a variable constraint for the regulated reaction. The invention further provides methods for making an in silico *Homo sapiens* model and methods for determining a *Homo sapiens* physiological function using a model of the invention.

44 Claims, 4 Drawing Sheets

OTHER PUBLICATIONS

Dooley et al., "An all D-amino acid opioid peptide with central analgesic activity from a combinatorial library," *Science*, 266:2019-2022 (1994).

Edwards and Palsson, "Systems properties of the haemophilus influenzae Rd metabolic genotype," *J. Biol. Chem.*, 274:17410-17416 (1999).

Edwards and Palsson, "The *Escherichia coli* MG1655 in silico metabolic genotype: its definition, characteristics, and capabilities," *Proc. Natl. Acad. Sci. USA*, 97:5528-5533 (2000).

Edwards et al., "Characterizing the metabolic phenotype: a phenotype phase plane analysis," *Biotech. Bioeng.*, 77:27-36 (2002).

Edwards et al., "In silico predictions of *Escherichia coli* metabolic capabilities are consistent with experimental data," *Nat. Biotech.*, 19:125-130 (2001).

European Journal of Biochemistry, Blackwell Science, Malden, Massachusetts.

Fell and Small, "Fat synthesis in adipose tissue an examination of stoichiometric constraints," *Biochem. J.*, 238:781-786 (1986).

Goto et al., *Bioinformatics*, vol. 14, pp. 591-599, 1998, see p. 591, col. 1. Availability Section; pp. 592-594, Implementation Section; Figures 1-3; and Tables 1-4.

Houghten et al., "Generation and use of synthetic peptide combinatorial libraries for basic research and discovery," *Nature*, 354:84-86 (1991).

Kunst et al., "The complete genome sequence of the gram-positive bacterium *Bacillus subtilis*," *Nature*, 390:249-256 (1997).

Majewski and Domach, "Simple constrained—optimization view of acetate overflow in *E. coli*," *Biotech. Bioeng.*,35:732-738 (1990).

Maughan, et al., "Biochemistry of exercise and training," Oxford University Press Oxford, England (1997).

Moszer et al., "SubtiList: the reference database for the *Bacillus subtilis* genome," *Nucl. Acids Res.*, 30(1):62-65 (2002).

Ogata et al., *Nucleic Acids Research*, vol. 27, pp. 29-34, 1999, see p. 34, Availability Section Tables 1-3; Figures 1 and 2; and pp. 30-32, Pathway Database Section.

Palsson, B., "The challenges of in silico biology," *Nat. Biotech*, 18:1147-1150 (2000).

Salway, J., "Metabolism at a glance," 2nd ed. Blackwell Science, Malden, CA (1999).

Sauer and Bailey, "Estimation of P-to-O ratio in *Bacillus subtilis* and its influence on maximum riboflavin yield," *Biotechnol. Bioeng.*, 64:750-754.

Schilling and Palsson, "Assessment of the metabolic capabilities haemophilus influenzae Rd through a genome-scale pathway analysis," *J. Theor. Biol.*, 203:249-283 (2000).

Schilling and Palsson, "The underlying pathway structure of biochemical reaction networks," *Proc. Natl. Acad. Sci. USA*, 95:4193-4198 (1998).

Schilling et al., "Combining pathway analysis with flux balance analysis for the comprehensive study of metabolic systems," *Biotech. Bioeng.*, 71:286-306 (2000).

Schilling et al., "Metabolic pathway analysis: basic concepts and scientific applications in the post-genomic era," *Biotech. Prog.*, 15:296-303 (1999).

Schilling et al., "Theory for the systemic definition of metabolic pathways and their use in interpreting metabolic function from a pathway-oriented ,perspective," *J. Theor. Biol.*, 203:229-248 (2000).

Schilling et al., "Toward metabolic phenomics: analysis of genomic data using flux balances," *Biotech. Prog.*, 15:288-295 (1999).

Schuster et al., "," *J. Theor. Biol.*, 203:249-283 (2002).

Shuster et al., "Exploring the pathway structure of metabolism" *Bioinformatics*, 18:351-361 (2002).

Sorlie et al., "Gene expression patterns of breast carcinomas distinguish tumor subclasses with clinical implications," *Proc. Natl. Acad. Sci. USA*, 98 (19):10869-10874 (2001).

Thomas, R., "Boolean formalization of genetic control circuits," *J. Theor. Biol.*, 42:563-585 (1973).

Thomas, R., "Logical analysis of systems comprising feedback loops," *J. Theor. Biol.*, 73:631-656 (1978).

Vanrolleghem et al., "Validation of a metabolic network for *Saccharomyces cerevisiae* using mixed substrate studies," *Biotech. Prog.*, 12:434-448 (1996).

Varma and Palsson, "Stoichiometric flux balance models quantitatively predict growth and metabolic by-product secretion in wild-type *Escherichia coli* W3110," *Appl. Env. Micro.*, 60:3724-3731 (1994).

Varma and Palsson,"Metabolic flux balancing: basic concepts, scientific and practical use," *Biotech.*, 12:994-998 (1994).

Adamowicz et al., "Nutritional complementation of oxidative glucose metabolism in *Escherichia coli* via pyrroloquinoline quinone-dependent glucose dehydrogenase and the Entner-Doudoroff pathway," *Appl. Environ. Microbiol.* 57(7):2012-2015 (1991).

Akutsu, "Estimation Algorithm of Genetic Network," *Mathmatical Science (Suri-Kagaku) Science* 37(6):40-46 (1999). (Original and Translation submitted herewith).

Alberty, "Calculation of Biochemical Net Reactions and Pathways by Using Matrix Operations," *Biophys. J.* 71(1):507-515 (1996).

Alm et al., "Genomic-sequence comparison of two unrelated isolates of the human gastric pathogen Helicobacter pylori," *Nature* 397(6715):176-80 (1999).

Alon et al., "Broad patterns of gene expression revealed by clustering analysis of tumor and normal colon tissues probed by oligonucleotide arrays," *Proc. Natl. Acad. Sci. USA*.96(12):6745-6750 (1999).

Alter et al., "Singular value decomposition for genome-wide expression data processing and modeling," *Proc. Natl. Acad. Sci. USA* 97(18):10101-10106 (2000).

Altschul et al., "Gapped BLAST and PSI-BLAST: A New Generation of Protein Database Search Programs," *Nucleic Acids. Res.* 25(17):3389-3402 (1997).

Alves et al., "Systemic properties of ensembles of metabolic networks: application of graphical and statistical methods to simple unbranched pathways," *Bioinformatics* 16(6):534-547 (2000).

Andre, "An overview of membrane transport proteins in *Saccharomyces cerevisiae*," *Yeast* 11(16):1575-1611 (1995).

Anonymous, "The yeast genome directory" *Nature* 387(6632 Suppl):5 (1997).

Appel et al., "A new generation of information retrieval tools for biologists: the example of the ExPASy WWW server," *Trends Biochem. Sci.* 19(6):258-260 (1994).

Arigoni et al., "A Genome-Based Approach for the Identification of Essential Bacterial Genes," *Nature Biotechnol.* 16(9):851-856 (1998).

Aristidou and Penttila, "Metabolic engineering applications to renewable resource utilization," *Curr. Opin. Biotechnol.* 11(2)187-198 (2000).

Attanoos et al., "Ileostomy polyps, adenomas, and adenocarcinomas," *Gut* 37(6):840-844 (1995).

Baba et al., "Construction of *Escherichia coli* K-12 in-frame, single-gene knockout mutants: the Keio collection," *Mol. Syst. Biol.* 2:2006-2008 (2006).

Bailey and Elkan, "Fitting a mixture model by expectation maximization to discover motifs in biopolymers," *Proc. Int. Conf. Intell. Syst. Mol. Biol.* 2:28-36 (1994).

Bailey and Gribskov, "Combining evidence using p-values: application to sequence homology searches," *Bioinformatics* 14(1):48-54 (1998).

Bailey, "Complex Biology With No Parameters," *Nat. Biotechnol.* 19(6):503-504 (2001).

Bairoch and Apweiler, "The SWISS-PROT Protein Sequence database and its supplement TrEMBL in 2000," *Nucleic Acids Res.* 28(1):45-48 (2000).

Ball et al., "Integrating functional genomic information into the *Saccharomyces* genome database," *Nucleic Acids Res.* 28(1):77-80 (2000).

Baltz et al., "DNA Sequence Sampling of the *Streptococcus pneumonia* Genome to Identify Novel Targets for Antibiotic Development," *Microbial. Drug Resist.* 4(1):1-9 (1998).

Ban et al., "Thymine and uracil catabolism in *Escherichia coli*," *J. Gen. Microbiol.* 73(2):267-272 (1972).

Bansal, "Integrating co-regulated gene-groups and pair-wise genome comparisons to automate reconstruction of microbial pathways," *Bioinformatics and Bioengineering.Conference* 209-216 (2001).

Bard et al., "Sterol mutants of *Saccharomyces cerevisiae*: chromatographic analyses," *Lipids* 12(8):645-654 (1977).

Baxevanis, "The Molecular Biology Database Collection: 2002 update," *Nucleic Acids Res.* 30:1-12 (2002).

Beard et al., "Energy Balance for Analysis of Complex Metabolic Networks," *Biophys. J.* 83(1):79-86 (2002).

Beckers et al., "Large-Scale Mutational Analysis for the Annotation of the Mouse Genome," *Curr. Opin. Chem. Biol.* 6(1)17-23 (2002).

Bell, et al., "Composition and functional analysis of the *Saccharomyces cerevisiae* trehalose synthase complex," *J. Biol. Chem.* 273(50):33311-33319 (1998).

Benjamini and Hochberg, "Controlling the False Discovery Rate: A Practical and Powerful Approach to Multiple Testing," *J.R. Statist. Soc. B* 57:289-300 (1995).

Benson et al., "GenBank," *Nucleic Acids Res.* 28(1):15-18 (2000).

Berry, "Improving production of aromatic compounds in *Escherichia coli* by metabolic engineering," *Trends Biotechnol.* 14(7):250-256 (1996).

Bialy, "Living on the Edges," *Nat. Biotechnol.* 19(2):111-112 (2001).

Bianchi and Zanella, "Hematologically important mutations: red cell pyruvate kinase (third update)," *Blood Cells Molecules Diseases* 15:47-53 (2000).

Birkholz, "Fumarate reductase of Helicobacter pylori—an immunogenic protein," *J. Med.Microbiol.* 41(1):56-62 (1994).

Birner et al., "Roles of phosphatidylethanolamine and of its several biosynthetic pathways in *Saccharomyces cerevisiae*," *Mol. Biol. Cell.* 12(4):997-1007 (2001).

Blackstock and Weir, "Proteomics: quantitative and physical mapping of cellular proteins," *Trends Biotechnol.* 17(3):121-127 (1999).

Blattner et al., "The Complete Genome Sequence of *Escherichia coli* K-12," *Science* 277(5331):1453-1474 (1997).

Bochner, "New technologies to assess genotype-phenotype relationships," *Nat. Rev. Genet.*4(4):309-314 (2003).

Boles et al., "A family of hexosephosphate mutases in *Saccharomyces cerevisia*," *Eur. J. Biochem.* 220(1):83-96 (1994).

Boles et al., "Characterization of a glucose-repressed pyruvate kinase (Pyk2p) in *Saccharomyces cerevisiae* that is catalytically insensitive to fructose-1,6-bisphosphate," *J. Bacteriol.* 179(9):2987-2993 (1997).

Boles et al., "Identification and characterization of MAE 1 ,the *Saccharomyces cerevisiae* structural gene encoding mitochondrial malic enzyme," *J. Bacteriol.* 180(11):2875-2882 (1998).

Bonarius et al., "Flux Analysis of Underdetermined Metabolic Networks: The Quest for the Missing Constraints," *Trends Biotechnol.* 15(8):308-314 (1997).

Bonarius et al., "Metabolic flux analysis of hybridoma cells in different culture media using mass balances," *Biotechnol. Bioeng.* 50(3):299-318 (1996).

Bono et al., "Reconstruction of amino acid biosynthesis pathways from the complete genome sequence," *Genome Res.* 8(3):203-210 (1998).

Bottomley et al., "Cloning, sequencing, expression, purification and preliminary characterization of a type II dehydroquinase from Helicobacter pylori," *Biochem. J.* 319(Pt 2):559-565 (1996).

Bourot and Karst, "Isolation and characterization of the *Saccharomyces cerevisiae* SUT1 gene involved in sterol uptake," *Gene* 165(1):97-102 (1995).

Burgard and Maranas, "Probing the Performance Limits of the *Escherichia coli* Metabolic Network Subject to Gene Additions or Deletions," *Biotechnol. Bioeng.* 74(5):364-375 (2001).

Burgard and Maranas, "Review of the Enzymes and Metabolic Pathways (EMP) Database," *Metab. Eng.* 3(3):193-194(2) (2001).

Burgard et al., "Minimal reaction sets for *Escherichia coli* metabolism under different growth requirements and uptake environments," *Biotechnol. Prog.* 17(5):791-797 (2001).

Burgard et al., "Optknock: a bilevel programming framework for identifying gene knockout strategies for microbial strain optimization," *Biotechnol. Bioeng.* 84(6):647-657 (2003).

Burns, "Acetyl-CoA carboxylase activity in Helicobacter pylori and the requirement of increased CO2 for growth," *Microbiology* 141(Pt 12):3113-3118 (1995).

Callis, "Regulation of Protein Degradation," *The Plant Cell* 7:845-857 (1995).

Carrier and Keasling, "Investigating Autocatalytic Gene Expression Systems through Mechanistic Modeling," *J. Theor. Biol.* 201(1):25-36 (1999).

Chadha et al., "Hybrid process for ethanol production from rice straw," *Acta Microbiol. Immunol. Hung.* 42(1):53-59 (1995).

Chadha et al., "Simultaneous saccharification and fermentation of rice straw into ethanol," *Acta Microbiol. Immunol. Hung.* 42(1):71-75 (1995).

Chalker et al., "Systematic identification of selective essential genes in Helicobacter pylori by genome prioritization and allelic replacement mutagenesis," *J. Bacteriol.* 183(4):1259-1268 (2001).

Chartrain et al., "Metabolic engineering and directed evotion for the production of pharmaceuticals," *Curr. Opin. Biotech.* 11(2):209-214 (2000).

Chen et al., "Characterization of the respiratory chain of Helicobacter pylori," *FEMS Immunol. Med. Microbiol.* 24(2):169-174 (1999).

Cherry et al., "SGD: *Saccharomyces* Genome Database," *Nucleic Acids Res.* 26(1):73-79 (1998).

Christensen and Nielsen, "Metabolic network analysis. A powerful tool in metabolic engineering," *Adv. Biochem. Eng. Biotechnol.* 66:209-231 (2000).

Ciriacy and Breitenbach, "Physiological effects of seven different blocks in glycolysis in *Saccharomyces cerevisiae*," *J. Bacteriol* 139(1):152-160 (1979).

Clarke, "Stability of Complex Reaction Networks," *Adv. Chem. Phys.* 43:1-125 (1980).

Clarke, "Complete set of steady states for the general stoichiometric dynamical system," *J Chem Phy* 75(10):4970-4979 (1981).

Clarke, "Stoichiometric network analysis," *Cell Biophys.* 12:237-253 (1988).

Clifton and Fraenkel, "Mutant studies of yeast phosphofructokinase.," *Biochemistry* 21(8):1935-1942 (1982).

Clifton et al., "Glycolysis mutants in *Saccharomyces cerevisiae*.," *Genetics* 88(1):1-11 (1978).

Compan et al., "Anaerobic activation of arcA transcription in *Escherichia coli*: roles of Fnr and ArcA," *Mol. Microbiol.* 11(5):955-964 (1994).

Costanzo et al., "YPD, PombePD and WormPD: model organism volumes of the BioKnowledge library, an integrated resource for protein information," Nucleic Acids Res. 29(1):75-9 (2001).

Cotter et al., "Aerobic regulation of cytochrome d oxidase (cydAB) operon expression in *Escherichia coli*: roles of Fnr and ArcA in repression and activation," Mol. Microbiol. 25(3):605-615 (1997).

Cover and Blaser, "Helicobacter pylori infection, a paradigm for chronic mucosal inflammation: pathogenesis and implications for eradication and prevention," *Adv. Intern. Med.* 41:85-117 (1996).

Covert and Palsson, "Constraints-based models: Regulation of Gene Expression Reduces the Steady-state Solution Space," *J. Theor. Biol.* 221:309-325 (2003).

Covert and Palsson, "Transcriptional Regulation in Constraints-based Metabolic Models of *Escherchia coli*," *J. Biol. Chem.* 277(31):28058-28064 (2002).

Cupp and McAlister-Henn, "Cloning and Characterization of the gene encoding the IDH1 subunit of NAD(+)-dependent isocitrate dehydrogenase from *Saccharomyces cerevisiae*," *J. Biol. Chem.* 267(23):16417-16423 (1992).

Dafoe et al., "In Silico Knowledge Discovery Biomedical databases," Proceedings of the SPIE Fifth Workshop on Neural Networks, San Francisco, Nov. 7-10, 1993.

Dandekar et al., "Pathway Alignment: Application to the Comparative Analysis of Glycolytic Enzymes," *Biochem. J.* 343:115-124 (1999).

D'Haeseleer et al., "Genetic network inference: from co-expression clustering to reverse engineering," *Bioinformatics* 16(8):707-726 (2000).

Danchin, "Comparison Between the *Escherichia coli* and *Bacillus subtilis* Genomes Suggests That a Major Function of Polynucleotide Phosphorylase is to Synthesize CDP," *DNA Res.* 4(1):9-18 (Feb. 1997).

Dantigny et al., "Transition rate kinetics from ethanol oxidation to glucose utilisation within a structured model of baker's yeast," *Appl. Microbiol. Biotechnol.* 36:352-357 (1991).

Datsenko and Wanner, "One-step inactivation of chromosomal genes in *Escherichia coli* K-12 using PCR products," *Proc. Natl. Acad. Sci. USA* 97(12):6640-6645 (2000).

Daum et al., "Biochemistry, cell biology and molecular biology of lipids of *Saccharomyces cerevisiae*," *Yeast* 14(16):1471-1510 (1998).

Daum et al., "Systematic analysis of yeast strains with possible defects in lipid metabolism," *Yeast* 15(7):601-614 (1999).

de Jong, "Modeling and simulation of genetic regulatory systems: a literature review," *J. Comput. Biol.* 9(1):67-103 (2002).

De Reuse et al., "The Helicobacter pylori ureC gene codes for a phosphoglucosamine mutase," *J. Bacteriol.* 179(11):3488-3493 (1997).

Delgado and Liao, "Identifying Rate-Controlling Enzymes in Metabolic Pathways without Kinetic Parameters," *Biotechnol. Prog.* 7:15-20 (1991).

Department of Energy, *Breaking the Biological Barriers to Cellulosic Ethanol* (2006).

Demain et al., "Cellulase, clostridia, and ethanol," *Microbio.l Mol. Biol. Rev.* 69(1):124-154 (2005).

DeRisi et al., "Use of cDNA microarray to analyse gene expression patters in human cancer," *Nat. Gene.* 14:457-460 (1996).

DeRisi et al., "Exploring the Metabolic and Genetic Control of Gene Expression on a Genomic Scale," *Science* 278(5338):680-686 (1997).

Dickson "Sphingolipid functions in *Saccharomyces cerevisiae*: comparison to mammals," *Annu. Rev. Biochem.* 67:27-48 (1998).

Dickson et al., "Serine palmitoyltransferase," *Methods Enzymol.* 311:3-9 (2000).

DiRusso and Black, "Long-chain fatty acid transport in bacteria and yeast. Paradigms for defining the mechanism underlying this protein-mediated process," *Mol. Cell. Biochem.* 192(1-2):41-52 (1999).

Duarte et al., "Reconstruction and validation of *Saccharomyces cerevisiae* iND750, a fully compartmentalized genome-scale metabolic model," *Genome Res.* 14(7):1298-1309 (2004).

Edwards and Palsson, "How Will Bioinformatics Influence Metabolic Engineering," *Biotechnol. Bioeng.* 58(2-3):162-169 (1998).

Edwards and Palsson, "Metabolic flux balance analysis and the in silico analysis of *Escherichia colia* K-12 gene deletions," *BMC Bioinform.* 1:1-10 (2000).

Edwards et al., "Characterizing Phenotypic Plasticity: A Phase Plane Analysis," *BMES/EMBS Conference, Proceedings of the First Joint*, vol. 2, p. 1217 (1999).

Edwards et al., "Genomically Based Comparative Flux Balance Analysis of *Escherichia coli* and *Haemophilus influenza*," Abstract of Papers, *Am. Chem. Soc.* 213(1-3):BIOT 50. San Francisco (1997).

Edwards and Palsson, "Robustness analysis of the *Escherichia coli* metabolic network," *Biotechnol. Prog.* 16(6):927-939 (2000).

Eisen et al., "Cluster analysis and display of genome-wide expression patterns," *Proc. Natl. Acad. Sci. USA* 95:14863-14868 (1998).

Eisenberg et al., "Protein Function in the Post-Genomic Era," *Nature* 405(6788):823-826 (2000).

Ermolaeva et al., "Prediction of Operons in Microbial Genomes," *Nucl. Acids Res.* 29(5):1216-1221 (2001).

Everett et al., "Pendred Syndrome is Caused by Mutations in a Putative Sulphate Transporter Gene (PDS)," *Nat. Genet.* 17:411-422 (1997).

Feist and Palsson, "The growing scope of applications of genome-scale metabolic reconstructions using *Escherichia coli*," *Natural Biotech.* 26(6):659-667 (2008).

Fiehn, "Metabolomics—the link between genotypes and phenotypes," *Plant Mol. Biol.* 48(1-2):155-171 (2002).

Fleischmann, "Whole-genome random sequencing and assembly of *Haemophilus influenzae* Rd," *Science* 269(5223):496-512 (1995).

Finel, "Does NADH play a central role in energy metabolism in Helicobacter pylori?," *Trends Biochem. Sci.* 23(11):412-413 (1998).

Fiorelli et al., "Chronic non-spherocytic haemolytic disorders associated with glucose-6-phosphate dehydrogenase variants," *Bailliere's Clinical Haematology*, 13:39-55 (2000).

Flikweert et al., "Pyruvate decarboxylase: an indispensable enzyme for growth of *Saccharomyces cerevisiae* on glucose.," *Yeast* 12(3):247-257 (1996).

Fotheringham, "Engineering biosynthetic pathways: new routes to chiral amino acids," *Curr. Opin. Chem. Biol.* 4(1):120-124 (2000).

Forst, "Network genomics—A Novel approach for the analysis of biological systems in the post-genomic era," *Mol. Biol. Rpts.* 29(3):265-280 (2002).

Forster et al., "Large-scale evaluation of in silico gene deletions in *Saccharomyces cerevisiae*," *Omics* 7(2)193-202 (2003).

Fraenkel, "The accumulation of glucose 6-phosphate from glucose and its effect in an *Escherichia coli* mutant lacking phosphoglucose isomerase and glucose 6-phosphate dehydrogenase," *J. Biol. Chem.* 243(24):6451-6457 (1968).

Fraser et al., "Microbial genome sequencing," *Nature* 06:799-803 (2000).

Fromont-Racine, et al., "Toward a functional analysis of the yeast genome through exhaustive two-hybrid screens," *Nat. Genet.* 16(3):277-282 (1997).

Fukuchi et al., "Isolation, overexpression and disruption of a *Saccharomyces cerevisiae* YNK gene encoding nucleoside diphosphate kinase," *Gene* 129(1):141-146 (1993).

Gaasterland and Selkov, "Reconstruction of Metabolic Networks Using Incomplete Information," *Proc. Int. Conf. Intel. Syst. Mol. Biol.* 3:127-135 (1995).

Galperin and Brenner, "Using Metabolic Pathway Databases for Functional Annotation," *Trends Genet.* 14(8):332-333 (1998).

Gancedo and Delgado, "Isolation and characterization of a mutant from *Saccharomyces cerevisiae* lacking fructose 1,6-bisphosphatase," *Eur. J .Biochem.* 139:651-655 (1984).

Gangloff et al., "Molecular cloning of the yeast mitochondrial aconitase gene (ACO1) and evidence of a synergistic regulation of expression by glucose plus glutamate.," *Mol. Cell. Biol.* 10(7):3551-3561 (1990).

Ge et al., "Cloning and functional characterization of Helicobacter pylori fumarate reductase operon comprising three structural genes coding for subunits C, A and B," *Gene* 204(1-2):227-234 (1997).

Glasner et al., "ASAP, a systematic annotation package for community analysis of genomes," *Nucleic Acids Res.* 31(1):147-151 (2003).

Goffeau, "Four years of post-genomic life with 6000 yeast genes," *FEBS Lett.* 480(1):37-41 (2000).

Gombert and Nielsen, "Mathematical modeling of metabolism," *Curr. Opin. Biotechnol.* 11(2):180-186 (2000).

Goryanin et al., "Mathematical simulation and analysis of cellular metabolism and regulation," *Bioinformatics* 15(9):749-758 (1999).

Goto et al., "LIGAND: chemical database for enzyme reactions," *Bioinformatics* 14(7):591-599 (1998).

Grewal et al., "Computer Modelling of the Interaction Between Human Choriogonadotropin and Its Receptor," *Protein Eng.* 7(2):205-211 (1994).

Griffin et al., "Complementary profiling of gene expression at the transcriptome and proteome levels in *Saccharomyces cerevisiae*," *Mol. Cell Proteomics* 1:323-333 (2002).

Grundy et al., "Regulation of the *Bacillus subtilis* acetate kinase gene by CcpA." *J. Bacteriol.* 175(22):7348-7355 (1993).

Guardia et al., "Cybernetic modeling and regulation of metabolic pathways in multiple steady states of hybridoma cells," *Biotech. Prog,* 16(5):847-853 (2000).

Guelzim et al., "Topological and causal structure of the yeast transcriptional regulatory network," Nat. Genet. 31(1):60-63 (2002).

Guetsova et al., "The isolation and characterization of *Saccharomyces cerevisiae* mutants that constitutively express purine biosynthetic genes," Genetics 147(2):383-397 (1997).

Hardison et al., "Globin Gene Server: A Prototype E-Mail Database Server Featuring Extensive Multiple Alignments and Data Compilation for Electronic Genetic Analysis," Genomics 21(2):344-353 (1994).

Hartig et al., "Differentially regulated malate synthase genes participate in carbon and nitrogen metabolism of *S. cerevisiae*.," *Nucleic Acids Res,* 20(21):5677-5686 (1992).

Hasty et al., "Computational Studies of Gene Regulatory Networks: In Numero Molecular Biology," *Nat. Rev. Genet.* 2(4):268-279 (2001).

Hata et al., "Characterization of a *Saccharomyces cerevisiae* mutant, N22, defective in ergosterol synthesis and preparation of [28-14C]ergosta-5,7-dien-3 beta-ol with the mutant," *J. Biochem.* 94(2):501-510 (1983).

Hatzimanikatis, et al., "Analysis and Design of Metabolic Reaction Networks Via MixedInterger linear Optimization," *AIChE Journal*, 42(5):1277-1292 (1996).
Hazell et al., "How Helicobacter pylori works: an overview of the metabolism of *Helicobacter pylori*," *Helicobacter* 2(1):1-12 (1997).
Heijnen et al., "Application of balancing methods in modeling the penicillin fermentation," *Biotechnol. Bioengin.* 21:2175-2201 (1979).
Heinisch et al., "Investigation of two yeast genes encoding putative isoenzymes of phosphoglycerate mutase.," *Yeast* 14(3):203-213 (1998).
Heinrich et al., "Metabolic regulation and mathematical models," *Prog. Biophys. Mol. Biol.* 32(1):1-82 (1977).
Henriksen et al., "Growth energetics and metabolism fluxes in continuous cultures of *Penicillium chrysogenum*," *J. Biotechnol.* 45(2):149-164 (1996).
Heyer et al., "Exploring expression data: identification and analysis of coexpressed genes," *Genome Res.* 9(11):1106-1115 (1999).
Holter et al., "Dynamic modeling of gene expression data," *Proc. Natl. Acad. Sci USA* 98(4):1693-1698 (2001).
Holter et al., "Fundamental patterns underlying gene expression profiles: simplicity from complexity," *Proc. Natl. Acad. Sci. USA* 97:8409-9414 (2000).
Hughes et al., "Functional discovery via a compendium of expression profiles," *Cell* 102(1):109-126 (2000).
Hughes et al., "Helicobacter pylori porCDAB and oorDABC genes encode distinct pyruvate: flavodoxin and 2-oxoglutarate:acceptor oxidoreductases which mediate electron transport to NADP," *J. Bacteriol.* 180(5):1119-1128 (1998).
Ideker et al., "Integrated Genomic and Proteomic Analyses of a Systematically Perturbed Metabolic Network," *Science* 292(5518):929-934 (2001).
Ince and Knowles, "Ethylene formation by cell-free extracts of *Escherichia coli*," *Arch. Microbiol.* 146(2):151-158 (1986).
Ishii et al., "DBTBS: a database of *Bacillus subtilis* promoters and transcription factors," *Nucleic Acids Res.* 29(1):278-280 (2001).
Iyer et al., "Genomic binding sites of the yeast cell-cycle transcription factors SBF and MBF," *Nature* 409(6819):533-538 (2001).
Jamshidi et al., "Dynamic simulation of the human red blood cell metabolic network," *Bioinformatics* 17(3):286-287 (2001).
Jamshidi et al., "In silico model-driven assessment of the effects of single nucleotide polymorphins (SNPs) on human red blood cell-metabolism," *Genome Res.* 12(11):1687-1692 (2002).
Jenkins and Nunn,"Genetic and molecular characterization of the genes involved in short-chain fatty acid degradation in *Escherichia coli*: the ato system," *J. Bacteriol.* 169(1):42-52 (1987).
Jenssen et al., "A Literature Network of Human Genes for High-Throughput Analysis of Gene Expression," *Nat. Gene.* 28(1):21-28 (2001).
Jorgensen et al., "Metabolic flux distributions in *Penicillium chrysogenum* during fed-batch cultivations." *Biotechnol. Bioeng*, 46(2):117-131 (1995).
Joshi and Palsson, "Metabolic dynamics in the human red cell. Part I—A comprehensive kinetic model," *J. Theor. Biol.* 141(4):515-528 (1989).
Juty et al., "Simultaneous Modeling of Metabolic, Genetic, and Product-Interaction Networks," *Brief. Bioinform*. 2(3):223-232 (2001).
Kanehisa and Goto, "Kyoto Encyclopedia of Genes and Genomes database (KEGG)," *Nucleic Acids Res.* 28(1):27-30 (2000).
Karp, "An ontology for biological function based on molecular interactions," *Bioinformatics* 16(3):269-285 (2000).
Karp, "Metabolic Databases," *Trends Biochem. Sci.* 23(3):114-116 (1998).
Karp et al., "Eco Cyc: encyclopedia of *Escherichia coli* genes and metabolism," *Nucleic Acids Res.* 27(1):55-58 (1999).
Karp et al., "HinCyc: A knowledge base of the complete genome and metabolic pathways of *H. influenzae*," *Proc. Int. Conf. Intel. Syst. Mol. Biol.* 4:116-124 (1996).
Karp et al., "Integrated pathway-genome databases and their role in drug discovery.," *Trends Biotechnol.* 17(7):275-281 (1999).
Karp et al., "The EcoCyc and MetaCyc databases," *Nucleic Acids Res.* 28(1):56-59 (2000).

Kaufman et al., "Towards a logical analysis of the immune response," *J. Theor. Biol.*114(4):527-561 (1985).
Kather et al., "Another unusual type of citric acid cycle enzyme in *Helicobacter pylori*: the malate:quinone oxidoreductase," *J. Bacteriol*. 182(11):3204-3209 (2000).
Keating et al., "An ethanologenic yeast exhibiting unusual metabolism in the fermentation of lignocellulosic hexose sugars," *J. Ind. Microbiol. Biotechnol*., 31(5):235-244 (2004).
Kelly, "The physiology and metabolism of the human gastric pathogen *Helicobacter pylori*," *Adv. Microb. Physiol*. 40:137-189 (1998).
Kim et al., "*Saccharomyces cerevisiae* contains two functional citrate synthase genes.," *Mol. Cell Biol*. 6(6):1936-1942 (1986).
Kirkman, et al., "Red cell NADP+ and NADPH in glucose-6-phosphate dehydrogenase deficiency," *J. Clin. Inv.* 55(4):875-878 (1975).
Kremling et al., "The organization of metabolic reaction networks. III. Application for diauxic growth on glucose and lactose," *Metab. Eng*. 3(4):362-379 (2001).
Kunst and Devine, "The project of sequencing the entire *Bacillus substilis* genome," *Res. Microb*. 142:905-912 (1991).
Lacroute, "Regulation of pyrimidine biosynthesis in *Saccharomyces cerevisiae*" *J. Bacteriol*. 95(3):824-832 (1968).
Latif and Rajoka, "Production of ethanol and xylitol from corn cobs by yeasts," *Bioresour. Technol*. 77(1):57-63 (2001).
Lee et al., "Incorporating qualitative knowledge in enzyme kinetic models using fuzzy logic," *Biotech. Bioeng*, 62(6):722-729 (1999).
Lendenmann and Egli, "Is *Escherichia coli* growing in glucose-limited chemostat culture able to utilize other sugars without lag?," *Microbiology*, 141(Pt 1):71-78 (1995).
Leyva-Vasquez and Setlow, "Cloning and nucleotide sequences of the genes encoding triose phosphate isomerase, phosphoglycerate mutase, and enolase from *Bacillus subtilis*," *J. Bacteriol*. 176(13):3903-3910 (1994).
Li and Wong, "Model-based analysis of oligonucleotide arrays: expression index computation and outlier detection," *Proc. Natl. Acad. Sci USA* 98(1):31-36 (2001).
Liao and Oh, "Toward predicting metabolic fluxes in metabolically engineered strains," *Metab. Eng*. 1(3):214-223 (1999).
Liao et al., "Pathway Analysis, Engineering, and Physiological Considerations for Redirecting Central Metabolism," *Biotechnol. Bioeng*. 52(1):129-140 (1996).
Link et al., "Methods for generating precise deletions and insertions in the genome of wild-type *Escherichia coli*: Application to open reading frame characterization," *J. Bacteriol*. 179(20):6228-6237 (1997).
Loftus et al., "Isolation, characterization, and disruption of the yeast gene encoding cytosolic NADP-specific isocitrate dehydrogenase," *Biochemistry* 33(32):9661-9667 (1994).
Lopez et al., "The yeast inositol monophosphatase is a lithium- and sodium-sensitive enzyme encoded by a non-essential gene pair," *Mol. Microbiol*. 31(4):1255-1264 (1999).
Lynd et al., "Biocommodity Engineering," *Biotech. Prog*. 15:777-793 (1999).
Mahadevan and Schilling, "The effects of alternate optimal solutions in constraint-based genome-scale metabolic models," *Metab. Eng*, 5(4):264-276 (2003).
Maier et al., "Hydrogen uptake hydrogenase in *Helicobacter pylori*," *FEMS Microbiol. Lett*. 141(1):71-76 (1996).
Marcelli et al., "The respiratory chain of *Helicobacter pylori*: identification of cytochromes and the effects of oxygen on cytochrome and menaquinone levels," *FEMS Microbiol. Lett*. 138(1):59-64 (1996).
Marshall and Warren, "Unidentified curved bacilli in the stomach of patients with gastritis and peptic ulceration," *Lancet*. 1(8390):1311-1315 (1984).
McAdams and Arkin, "It's a noisy business! Genetic regulation at the nanomolar scale," *Trends Genetics* 15(2):65-69 (1999).
McAdams and Arkin, "Stochastic mechanisms in gene expression," *Proc. Natl. Acad.Sci. USA* 94(3):814-819 (1997).
McAdams and Shapiro, "Circuit simulation of genetic networks." *Science* 269:650-656 (1995).
McAdams and Arkin, "Simulation of Prokaryotic Genetic Circuits," *Ann. Rev. Biophysics Biomol. Structure* 27:199-224 (1998).

McAlister-Henn and Thompson, "Isolation and expression of the gene encoding yeast mitochondrial malate dehydrogenase.," *J. Bacteriol.* 169(11):5157-5166 (1987).

McGee, "*Helicobacter pylori* rocF is required for arginase activity and acid protection in vitro but is not essential for colonization of mice or for urease activity," J. Bacteriol. 181(23):7314-7322 (1999).

Meldrum, "Automation for genomics, part one: preparation for sequencing," *Genome Res.* 10(8):1081-1092 (2000).

Mendes et al., "Non-linear optimization of biochemical pathways: Applications to metabolic engineering and parameter estimation," *Bioinformatics* 14(10):869-883 (1998).

Mendz and Hazell "Aminoacid utilization by *Helicobacter pylori,*" *Int. J. Biochem. Cell Biol.* 27(10):1085-1093 (1995).

Mendz and Hazell, "Fumarate catabolism in *Helicobacter pylori,*" *Biochem. Mol. Biol. Int.* 31(2):325-332 (1993).

Mendz and Hazell, "Glucose phosphorylation in *Helicobacter pylori,*" *Arch. Biochem. Biophys.* 300(1):522-525 (1993).

Mendz et al., "Glucose utilization and lactate production by *Helicobacter pylori,*" *J. Gen. Microbiol.* 139(12):3023-3028 (1993).

Mendz et al., "Characterisation of glucose transport in *Helicobacter pylori,*" *Biochim Biophys. Acta* 1244(2-3):269-276 (1995).

Mendz et al., "Characterization of fumarate transport in *Helicobacter pylori,*" *J. Membr. Biol.* 165(1):65-76 (1998).

Mendz et al., "De novo synthesis of pyrimidine nucleotides by *Helicobacter pylori,*" *J. Appl. Bacteriol.* 77(1):1-8 (1994).

Mendz et al., "Fumarate reductase: a target for therapeutic intervention against *Helicobacter pylori,*" *Arch. Biochem. Biophys.* 321(1):153-159 (1995).

Mendz et al., "Purine metabolism and the microaerophily of *Helicobacter pylori,*" *Arch. Microbiol.* 168(6):448-456 (1997).

Mendz et al., "Pyruvate metabolism in *Helicobacter pylori,*" *Arch Microbiol*, 162(3):187-192 (1994).

Mendz et al., "Salvage synthesis of purine nucleotides by *Helicobacter pylori,*" *J. Appl. Bacteriol.* 77(6):674-681 (1994).

Mendz et al., "The Entner-Doudoroff pathway in *Helicobacter pylori,*" *Arch. Biochem. Biophys.* 312(2):349-356 (1994).

Mendz, et al., "In situ characterization of *Helicobacter pylori* arginase," *Biochim Biophys. Acta* 1388(2):465-477 (1998).

Mewes et al., "MIPS: A database for genomes and protein sequences," *Nucleic Acids Res.* 30(1):31-34 (2002).

Mitchell, "The GLN1 locus of *Saccharomyces cerevisiae* encodes glutamine synthetase," *Genetics* 111(2):243-258 (1985).

Moszer et al., "SubtiList: the reference database for the *Bacillus subtilis* genome," *Nucleic Acids Res.* 30(1):62-65 (2002).

Mulquiney and Kuchel, "Model of 2,3-bisphosphoglycerate metabolism in the human erythrocyte based on detailed enzyme kinetic equations: computer simulation and metabolic control analysis," *Biochem. J.* 342(Pt 3):597-604 (1999).

Murray and Greenberg, "Expression of yeast INM1 encoding inositol monophosphatase is regulated by inositol, carbon source and growth stage and is decreased by lithium and valproate," *Mol Microbiol* 36(3):651-661 (2000).

Nedenskov, "Nutritional requirements for growth of *Helicobacter pylori,*" *Appl. Environ. Microbiol.* 60(9):3450-3453 (1994).

Nissen et al., "Expression of a cytoplasmic transhydrogenase in *Saccharomyces cerevisiae* results in formation of 2-oxoglutarate due to depletion of the NADPH pool," *Yeast* 18(1):19-32 (2001).

Nissen et al., "Flux distributions in anaerobic, glucose-limited continuous cultures of *Saccharomyces cerevisiae,*" *Microbiology* 143(Pt 1):203-218 (1997).

Ogasawara, "Systematic function analysis of *Bacillus subtilis* genes," *Res. Microbiol.* 151(2):129-134 (2000).

Ostergaard et al., "Increasing galactose consumption by *Saccharomyces cerevisiae* through metabolic engineering of the GAL gene regulatory network," *Nat. Biotech.* 18:1283-1286 (2000).

Oh and Liao, "Gene expression profiling by DNA microarrays and metabolic fluxes in *Escherichia coli,*" *Biotech. Prog,* 16:278-286 (2000).

Olsson et al., "Separate and simultaneous enzymatic hydrolysis and fermentation of wheat hemicellulose with recombinant xylose utilizing *Saccharomyces cerevisiae,*" *Appl. Biochem. Biotechnol.* 129-132:117-129 (2006).

Otto, et al., "A mathematical model for the influence of fructose 6-phosphate, ATP, potassium, ammonium and magnesium on the phosphofructokinase from rat erythrocytes," *Eur. J. Biochem.* 49(1):169-178 (1974).

Ouzounis and Karp, "Global Properties of the Metabolic Map of *Escherichia coli,*" *Genome Res.* 10(4):568-576 (2000).

Overbeek et al., "WIT: Integrated System for High-Throughput Genome Sequence Analysis and Metabolic Reconstruction" *Nucleic Acids Res.* 28(1):123-125 (2000).

Overkamp et al., "In vivo analysis of the mechanisms for oxidation of cytosolic NADH by *Saccharomyces cerevisiae* mitochondria," *J. Bacteriol.* 182(10):2823-2830 (2000).

Ozcan et al., "Glucose uptake and catabolite repression in dominant HTR1 mutants of *Saccharomyces cerevisiae.,*" *J. Bacteriol.* 175(17):5520-5528 (1993).

Pallotta et al., "*Saccharomyces cerevisiae* mitochondria can synthesise FMN and FAD from externally added riboflavin and export them to the extramitochondrial phase," *FEBS Lett.* 428(3):245-249 (1998).

Palmieri et al., "Identification and functions of new transporters in yeast mitochondria," *Biochim. Biophys. Acta* 1459(2-3):363-369 (2000).

Palmieri et al., "Identification of the yeast ACR1 gene product as a succinate-fumarate transporter essential for growth on ethanol or acetate," *FEBS Lett.* 417(1):114-118 (1997).

Palmieri et al., "Identification of the yeast mitochondrial transporter for oxaloacetate and sulfate," *J. Biol. Chem.* 274(32):22184-22190 (1999).

Palmieri et al., "Yeast mitochondrial carriers: bacterial expression, biochemical identification and metabolic significance," *J. Bioeneg. Biomem.,* 32(1):67-77 (2000).

Palsson, "What Lies Beyond Bioinformatics," *Nat. Biotechnol.* 15:3-4 (1997).

Papin et al., "The genome-scale metabolic extreme pathway structure in *Haemophilus influenzae* shows significant network redundancy," *J. Theor. Biol.* 215(1):67-82 (2002).

Patel and West, "Degradation of the pyrimidine bases uracil and thymine by *Escherichia coli* B" *Microbios.* 49(199):107-113 (1987).

Parks, "Metabolism of sterols in yeast," *CRC Crit. Rev. Microbiol.* 6(4):301-341 (1978).

Parks et al., "Use of sterol mutants as probes for sterol functions in the yeast, *Saccharomyces cerevisiae ,*" *Crit. Rev. Biochem. Mol. Bio.* 34(6):399-404 (1999).

Paulsen et al., "Unified inventory of established and putative transporters encoded within the complete genome of *Saccharomyces cerevisiae,*" *FEBS Lett.* 430(1-2):116-125 (1998).

Pearson et al., "Comparison of DNA Sequences With Protein Sequences," *Genomics* 46(1):24-36 (1997).

Pennisi, "Laboratory Workhouse Decoded," *Science* 277(5331):1432-1434 (1997).

Persson et al., "Phosphate permeases of *Saccharomyces cerevisiae*: structure, function and regulation," *Biochim. Biophys. Acta* 1422(3):255-272 (1999).

Peterson et al., "The Comprehensive Microbial Resource," *Nucleic Acids Res,* 29(1):123-125 (2001).

Pieper and Reineke, "Engineering bacteria for bioremediation," *Curr. Opin. Biotech.*11(3):262-270 (2000).

Pharkya et al., "Exploring the overproduction of amino acids using the bilevel optimization framework OptKnock," *Biotechnol. Bioeng,* 84(7):887-899 (2003).

Phelps et al., "Metabolomics and microarrays for improved understanding of phenotypic characteristics controlled by both genomics and environmental constraints," *Curr. Opin. Biotechnol.* 13(1):20-24 (2002).

Pitson et al., "The tricarboxylic acid cycle of *Helicobacter pylori,*" *Eur. J. Biochem.* 260(1):258-267 (1999).

Pramanik and Keasling, "Stoichiometric Model of *Escherichia coli* Metabolism: Incorporation of Growth-Rate Dependent Biomass Composition and Mechanistic Energy Requirements," *Biotechnol. Bioeng.* 56(4):398-421 (1997).

Price et al., "Determination of redundancy and systems properties of the metabolic network of *Helicobacter pylori* using genome-scale extreme pathway analysis," *Genome Res.* 12(5):760-769 (2002).

Price et al., "Genome-scale models of microbial cells: evaluating the consequences of constraints," *Nat. Rev. Microbiol.* 2(11):886-897 (2004).

Price et al., "Network-based analysis of metabolic regulation in the human red blood cell," *J. Theor. Biol.* 225(2):185-194 (2003).

Raclot et al., "Selective release of human adipocyte fatty acids according to molecular structure," *Biochem. J.* 324 (Pt3):911-915 (1997).

Rao and Arkin "Control motifs for intracellular regulatory networks," *Ann. Rev. Biomed. Eng.* 3:391-419 (2001).

Przybyla-Zawislak et al., "Genes of succinyl-CoA ligase from *Saccharomyces cerevisiae.*," *Eur. J. Biochem.* 258(2):736-743 (1998).

Qian et al., "Ethanol production from dilute-Acid softwood hydrolysate by co-culture," *Appl. Biochem. Biotechnol.* 134(3):273-284 (2006).

Reed and Palsson, "Thirteen years of building constraint-based in silico models of *Escherichia coli*" *J. Bacteriol.* 185(9):2692-2699 (2003).

Reed et al., "An expanded genome-scale model of *Escherichia coli* K-12 (iJR904 GSM/GPR)," *Genome Biol.* 4(9):R54 (2003).

Ren et al., "Genome-wide location and function of DNA binding proteins," *Science* 290(5500):2306-2309 (2000).

Regenberg et al., "Substrate specificity and gene expression of the amino-acid permeases in *Saccharomyces cerevisiae*," *Curr. Genet.* 36(6):317-328 (1999).

Remize et al., "Engineering of the pyruvate dehydrogenase bypass in *Saccharomyces cerevisiae*: role of the cytosolic Mg(2+) and mitochondrial K(+) acetaldehyde dehydrogenases Ald6p and Ald4p in acetate formation during alcoholic fermentation," *Appl. Environ. Microbiol.* 66(8):3151-3159 (2000).

Repetto and Tzagoloff, "In vivo assembly of yeast mitochondrial alpha-ketoglutarate dehydrogenase complex," *Mol. Cell. Biol.* 11(8):3931-3939 (1991).

Romero and Karp, "Nutrient-Related Analysis of Pathway/Genome Databases," *Pac. Symp. Biocomput.* 471-482 (2001).

Reynolds and Penn, "Characteristics of *Helicobacter pylori* growth in a defined medium and determination of its amino acid requirements," *Microbiology* 140(Pt 10):2649-2656 (1994).

Rhee et al., "Activation of gene expression by a ligand-induced conformational change of a protein-DNA complex," *J. Biol. Chem.* 273(18):11257-11266 (1998).

Saier, "Genome sequencing and informatics: new tools for biochemical discoveries," *Plant Physiol.* 117(4):1129-1133 (1998).

Salgado et al., "RegulonDB (version 3.2): transcriptional regulation and operon organization in *Escherichia coli* K-12," Nucleic Acids Res. 29(1):72-74 (2001).

Salmon et al., "Global gene expression profiling in *Escherichia coli* K12. The effects of oxygen availability and FNR," *J. Biol. Chem.* 278(32):29837-29855 (2003).

Sauer, "Evolutionary Engineering of Industrially Important Microbial Phenotypes," *Adv. Biochem. Eng. Biotechnol.* 73:129-169 (2001).

Sauer et al., "Metabolic Capacity of *Bacillus subtilis* for the Production of Purine Nucleosides, Riboflavin, and Folic Acid," *Biotechnol. Bioeng.* 59(2):227-238 (1998).

Sauer et al., "Metabolic flux ratio analysis of genetic and environmental modulations of *Escherichia coli* central carbon metabolism," *J. Bacteriol.* 181(21):6679-6688 (1999).

Savageau, "Biochemical systems analysis. I. Some mathematical properties of the rate law for the component enzymatic reactions," *J Theor Biol*, 25(3):365-369 (1969).

Savageau, "Development of fractal kinetic theory for enzyme-catalysed reactions and implications for the design of biochemical pathways," *Biosys.* 47(1-2):9-36 (1998).

Savinell and Palsson, "Network Analysis of Intermediary Metabolism using Linear Optimization. I. Development of Mathematical Formalism," *J. Theor. Biol.* 154:421-454 (1992).

Schaaff-Gerstenschlager and Zimmermann, "Pentose-phosphate pathway in *Saccharomyces cerevisiae*: analysis of deletion mutants for transketolase, transaldolase, and glucose 6-phosphate dehydrogenase," *Curr. Genet.* 24(5):373-376 (1993).

Schena et al., "Quantitative monitoring of gene expression patterns with a complementary DNA microarray," *Science* 270(5235):467-470 (1995).

Schilling et al., "Genome-scale metabolic model of *Helicobacter pylori* 26695," *J. Bacteriol.* 184(16):4582-4593 (2002).

Schilling et al., "Toward Metabolic Phenomics: Analysis of Genomic Data Using Flux Balances," *Biotechnol. Prog.* 15(3):288-295 (1999).

Schuster and Hilgetag "On elementary flux modes in biochemical reaction systems at steady state," *J Biol Syst*, 2(2):165-182 (1994).

Schuster et al., "A general definition of metabolic pathways useful for systematic organization and analysis of complex metabolic networks," *Nature Biotechnol.* 18(3):326-332 (2000).

Schuster et al., "Detection of elementary flux modes in biochemical networks: a promising tool for pathway analysis and metabolic engineering," *Trends Biotechnol.* 17(2):53-60 (1999).

Schwikowski et al., "A network of protein-protein interactions in yeast," *Nature Biotechnol.* 18(12):1257-1261 (2000).

Scott et al., "The Pendred Syndrome Gene Encodes a Chloride-Iodide Transport Protein," *Nat. Genet.* 21(4):440-443 (1999).

Sedivy and Fraenkel, "Fructose bisphosphatase of *Saccharomyces cerevisiae*. Cloning, disruption and regulation of the FBP1 structural gene.," *J. Mol. Biol.* 186(2):307-319 (1985).

Selkov et al., "A reconstruction of the metabolism of *Methanococcus jannaschii* from sequence data," *Genetics* 197(1-2):GC11-26 (1997).

Selkov et al., "Functional Analysis of Gapped Microbial Genomes: Amino Acid Metabolism of Thiobacillus Ferroxidans," *Proc. Nat.l Acad. Sci. USA* 97(7):3509-3514 (2000).

Selkov et al., "MPW: the metabolic pathways database," *Nucleic Acids Res.* 26(1):43-45 (1998).

Selkov et al., "The metabolic pathway collection from EMP: the enzymes and metabolic pathways database," *Nucleic Acids Res.* 24(1):26-28 (1996).

Shen-Orr et al., "Network motifs in the transcriptional regulation network of *Escherichia coli*," *Nat. Genet.* 31(1):64-68 (2002).

Sherlock, "Analysis of large-scale gene expression data," *Curr. Opin. Immunol.* 12:201-205 (2000).

Shipston and Bunch, "The physiology of L-methionine catabolism to the secondary metabolite ethylene by *Escherichia coli*," *J. Gen. Microbiol.* 135(6), 1489-1497 (1989).

Silve et al., "The immunosuppressant SR 31747 blocks cell proliferation by inhibiting a steroid isomerase in *Saccharomyces cerevisiae*," *Mol. Cell. Biol.* 16(6):2719-2727 (1996).

Skouloubris et al., "The Helicobacter pylori UreI protein is not involved in urease activity but is essential for bacterial survival in vivo," *Infect. Immun.* 66(9):4517-4521 (1998).

Smith et al., "Functional analysis of the genes of yeast chromosome V by genetic footprinting.," *Science* 274(5295):2069-2074 (1996).

Somogyi and Sniegoski, "Modeling the complexity of genetic networks: understanding the multigenic and pleitropic regulation," *Complexity* 1(6):45-63 (1996).

Stark et al., "Amino acid utilisation and deamination of glutamine and asparagine by *Helicobacter pylori*," *J. Med. Microbiol.* 46(9):793-800 (1997).

Stephanopoulos, "Metabolic Engineering," *Biotechnol. Bioeng.* 58(2-3):119-120 (1998).

Stephanopoulos, "Metabolic engineering," *Curr. Opin. Biotechnol.* 5(2):196-200 (1994).

Summers et al., "*Saccharomyces cerevisiae* cho2 mutants are deficient in phospholipid methylation and cross-pathway regulation of inositol synthesis" *Genetics*, 120(4):909-922 (1988).

Swartz, "A Pure approach to constructive biology.," *Nat. Biotechnol.* 19(8):732-733 (2001).

Syvanen, "Accessing genetic variation: Genotyping single nucleotide polymorphisms.," *Nat. Rev. Genet.* 2(12):930-942 (2001).

Szambelan et al., "Use of Zymomonas mobilis and *Saccharomyces cerevisiae* mixed with *Kluyveromyces fragilis* for improved ethanol production from Jerusalem artichoke tubers," *Biotechnol. Lett.* 26(10):845-848 (2004).

Tamayo et al., "Interpreting patterns of gene expression with self-organizing maps: methods and application to hematopoietic differentiation," *Proc. Natl. Acad. Sci. USA* 96(6):2907-2912 (1999).

Tanaka and Zerez, "Red cell enzymopathies of the glycolytic pathway," *Semin. Hematol.* 27(2):165-185 (1990).

Tandeitnik et al., "Modeling of biological neurons by artificial neural networks," Nineteenth Convention of Electrical and Electronics Engineers in Israel, Jerusalem, Israel, New York, NY USA, pp. 239-242 (1996).

Taniguchi and Tanaka, "Clarification of interactions among microorganisms and development of co-culture system for production of useful substances," *Adv. Biochem. Eng. Biotechnol.*, 90:35-62 (2004).

Tao et al., "Engineering a homo-ethanol pathway in *Escherichia coli*: increased glycolytic flux and levels of expression of glycolytic genes during xylose fermentation," *J. Bacteriol.* 183(10):2979-2988 (2001).

ter Linde, et al., "Genome-wide transcriptional analysis of aerobic and anaerobic chemostat cultures of *Saccharomyces cerevisiae*," *J Bacteriol*, 181(24):7409-7413 (Dec. 1999).

Thieffry and Thomas, "Dynamical behavior of biological regulatory networks II. Immunity control in bacteriophage lambda," *Bull. Math Biol*. 57(2):277-297 (1995).

Thomas and Surdin-Kerjan, "Metabolism of sulfur amino acids in *Saccharomyces cerevisiae*," *Microbiol Mol Biol Rev*, 61(4):503-532 (1997).

Tomb et al., "The complete genome sequence of the gastric pathogen *Helicobacter pylori*," *Nature* 388(6642):539-547 (1997).

Tomita et al., "E-Cell: Software Environment for Whole-Cell Simulation," *Bioinformatics* 15(1):72-84 (1999).

Trotter et al., "A genetic screen for aminophospholipid transport mutants identifies the phosphatidylinositol 4-kinase, STT4p, as an essential component in phosphatidylserine metabolism," *J. Biol. Chem*.273(21):13189-13196 (1998).

Uetz et al., "A comprehensive analysis of protein—protein interactions in *Saccharomyces cerevisiae*," *Nature* 403(6770):623-627 (2000).

Van den Berg,"ACS2, a *Saccharomyces cerevisiae* gene encoding acetyl-coenzyme a synthetase, essential for growth on glucose," *Eur. J. Biochem*. 231(3):704-713 (1995).

Van Dijken et al., "Alcoholic fermentation by 'non-fermentative' yeasts," *Yeast* 2(2):123-127 (1986).

Van Dijken et al., "Kinetics of growth and sugar consumption in yeasts," *Antonie Van Leeuwenhoek*, 63(3-4):343-352 (1993).

Varma and Palsson, "Metabolic capabilities of *Escherichia coli*. II: Optimal Growth Patterns.," *J. Theor. Biol*. 165:503-522 (1993).

Varma and Palsson, "Metabolic capabilities of *Escherichia coli*: I. Synthesis of Biosynthetic Precursors and Cofactors," *J. Theor. Biol*. 165:477-502 (1993).

Varma and Palsson, "Parametric sensitivity of stoichiometric flux balance models applied to wild-type *Escherichia coli* metabolism," *Biotechnol. Bioeng*. 45(1):69-79 (1995).

Varma and Palsson, "Stoichiometric flux balance models quantitatively predict growth and metabolic by-product secretion in wild-type *Escherichia coli* W3110," *Appl. Environ. Microbiol.* 60(10):3724-3731 (1994).

Varma et al., "Metabolic Flux Balancing: Basic Concepts, Scientific and Practical Use," *Biotechnology* 12:994-998 (1994).

Varma, et al., "Stoichiometric Interpretation of *Escherichia coli* Glucose Catabolism Under Various Oxygenation Rates.," *Appl Environ Microbiol*, 59(8):2465-2473 (1993).

Varner and Ramkrishna, "Mathematical Models of Metabolic Pathways," *Curr. Opin. Biotechnol*. 10(2):146-150 (1999).

Varner, "Large-scale prediction of phenotype: concept," *Biotech. Bioeng*. 69(6):664-678 (2000).

Vaseghi, et al., "In vivo Dynamics of the pentose phosphate pathway in *Saccharomyces cerevisiae*," *Meta Engin*. 1:128-140 (1999).

Velculescu et al., "Analysing uncharted transcriptomes with SAGE," *Trends Genet*. 16(10):423-425 (2000).

Venter et al., "Shotgun sequencing of the human genome," *Science* 280(5369):1540-1542 (1998).

Verduyn et al., "A theoretical evaluation of growth yields of yeasts," *Antonie Van Leeuwenhoek* 59(1):49-63 (1991).

Verduyn et al., "Energetics of *Saccharomyces cerevisiae* in anaerobic glucose-limited chemostat cultures," *J. Gen. Microbiol*. 136:405-412 (1990).

Verduyn, "Physiology of yeasts in relation to biomass yields," *Antonie Van Leeuwenhoek* 60(3-4):325-353 (1991).

Vissing et al., "Paradoxically Enhanced Glucose Production During Exercise in Humans with Blocked Glycolysis Caused by Muscle Phosphofructokinase Deficiency," *Neurology* 47(3):766-771 (1996).

Vo et al., "Reconstruction and functional characterization of the human mitochondrial metabolic network abased on proteomic and biochemical dataz," *J. Biol. Chem*. 279(38):39532-39540 (2004).

Wang et al., "Computer-aided baker's yeast fermentations," *Biotechnol. Bioeng*. 19(1):69-86 (1977).

Wang et al., Computer Control of Bakers' Yeast Production, *Biotechnol. Bioeng*. 21:975-995 (1979).

Waterston and Sulston, "The Human Genome Project: reaching the finish line," *Science* 282(5386):53-54 (1998).

Wen et al., "Large-scale temporal gene expression mapping of central nervous system development," *Proc. Natl. Acad. Sci. USA* 95(1):334-339 (1998).

Wiback and Palsson, "Extreme pathway analysis of human red blood cell metabolism," *Biophys. J*. 83:808-818 (2002).

Wieczorke et al., "Concurrent knock-out of at least 20 transporter genes is required to block uptake of hexoses in *Saccharomyces cerevisiae*," *FEBS Lett*. 464(3):123-128 (1999).

Wills and Melham, "Pyruvate carboxylase deficiency in yeast: a mutant affecting the interaction between the glyoxylate and Krebs cycles.," *Arch. Biochem. Biophys*. 236(2):782-791 (1985).

Wingender et al., "The TRANSFAC system on gene expression regulation," *Nucleic Acids Res*. 29(1):281-283 (2001).

Winzeler et al., "Functional characterization of the *S. cerevisiae* genome by gene deletion and parallel analysis," *Science* 285(5429):901-906 (1999).

Wong et al., "Mathematical Model of the Lac Operon: Inducer Exclusion, Catabolite Repression, and Diauxic Growth on Glucose and Lactose," *Biotechnol. Prog*.13(2):132-143 (1997).

Xie and Wang, "Energy Metabolism and ATP Balance in Animal Cell Cultivation Using a Stoichiometrically Based Reaction Network," *Biotech. Bioeng*, 52:591-601 (1996).

Xie and Wang, "Material Balance Studies on Animal Cell Metabolism Using a Stoichiometrically Based Reaction Network," *Biotech. Bioeng*, 52:579-590 (1996).

Xie and Wang, "Integrated Approaches to the Design of Media and Feeding Strategies for Fed-Batch Cultures of Animal Cells," *Trends Biotechnol*. 15(3):109-113 (1997).

Yamada et al., "Effects of common polymorphisms on the properties of recombinant human methylenetetrahydrofolate reductase," *Proc. Natl. Acad. Sci USA* 98(26):14853-14858 (2001).

Yeung et al., "Model-based clustering and data transformations for gene expression data," *Bioinformatics* 17(10):977-987 (2001).

Yeung et al., "Reverse engineering gene networks using singular value decomposition and robust regression," *Proc. Natl. Acad. Sci. USA* 99(9):6163-6168 (2002).

Yoshida et al., "Combined transcriptome and proteome analysis as a powerful approach to study genes under glucose repression in *Bacillus subtilis*," *Nucleic Acids Res*. 29(3):683-692 (2001).

Zeng et al., "Use of respiratory quotient as a control parameter for optimum oxygen supply and scale-up of 2,3-butanediol production under microaerobic conditions," *Biotechnol. Bioeng*, 44(9):1107-1114 (1994).

Zhu and Zhang, "SCPD: a promoter database of the yeast *Saccharomyces cerevisiae*," *Bioinformatics* 15(7-8):607-611 (1999).

Zigova, "Effect of RQ and pre-seed conditions on biomass and galactosyl transferase production during fed-batch culture of *S. cerevisiae* BT150," *J. Biotechnol*. 80(1):55-62 (2000).

Zanella and Bianchi, "Red cell pyruvate kinase deficiency: from genetics to clinical manifestations," *Bailliere's Best Pract. Res. Clin. Haematol*. 13(1):57-81 (2000).

Zweytick et al., "Biochemical characterization and subcellular localization of the sterol C-24(28) reductase, erg4p, from the yeast *Saccharomyces cerevisiae*," *FEBS Lett*. 470(1):83-87 (2000).

URL affymetrix.com/index.affx (As printed on Sep. 18, 2009).

URL affymetrix.com/products_services/arrays/specific/ecoli_antisense.affx. (As printed on Sep. 18, 2009).

URL asap.ahabs.wisc.edu/annotation/php/logon.php, The ASAP website. (As printed on Sep. 17, 2009).

URL ca.expasy.org/sprot/ protein database SWISS—PROT. (As printed on Jun. 15, 2009).

Five pages from URL: web.archive.org/web/20050731094028/ http://www.chem.qmw.ac.uk/iubmb/enzyme/ EnzymeNomenclature database maintained by G. P. Moss of Queen Mary and Wesffield Colege in the United Kingdom; Date Obtained May 15, 2009.

URL dchip.org, dChip software. (As printed on Jun. 15, 2009).

URL Dictionary.com pp. 1-2 (2004), Matrix. (As printed on Nov. 12, 2004).

Three pages from URL: web.archive.org/web/19981206132808/ http://ecocyc.panbio.com/ecocyc/ecocyc.html; Ecocyc; obtained on Sep. 18, 2009.

URL enzobio.com/lifesci_index.htm, Enzo BioArray Terminal Labeling Kit protocol. (As printed on Sep. 18, 2009).

URL genetics.wisc.edu/, *E. coli* Genome Project at the University of Wisconsin. As printed on Sep. 18, 2009).

URL genome.ad.jp/kegg/, Kyoto Encyclopedia of Genes and Genomes database (KEGG). (As printed on Sep. 18, 2009).

URL Genome.jp Website, KEGG *Bacillus subtillis*, 1-7 2005. (As printed on Sep. 18, 2009).

URL genome.tugraz.at/Software/Genesis/Description.html, "Genesis" software. (As printed on Sep. 18, 2009).

Six pages from URL: web.archive.org/web/2005025215224/ genomewww.stanford.edu/~sherlock/cluster.html, "XCluster" software: obtained on Sep. 18, 2009.

Home page from URL: web.archive.org/web/20050201083239/ igweb.integratedgenomics.com/MPW/, Metabolic pathways database (MPW), obtained on Sep. 18, 2009.

URL integratedgenomics.com, ERGO from Integrated Genomics. (As printed on Sep. 18, 2009).

Three pages from URL: web.archive.org/web/2007001095540/ http://mips.gsf.de/proj/yeast/pathways on Jun. 6, 2008. MIPS, website: Comprehensive Yeast Genome Database—Pathways; Date Obtained Sep. 18, 2009.

URL ncbi.nlm.gov, Genbank genome database. (Jun. 15, 2009).

Two pages from URL: www.ncbi.nlm.nih.gov/sites/ entrz?db=genome obtained on Jun. 15, 2009.

URL ncbi.nlm.nih.gov/LocusLink/LocusLink database maintained by the NCBI. (As printed on Jun. 15, 2009).

URL ncbi.nlm.nih.gov/Taxonomy/taxonomyhome.html/. (As printed on Sep. 18, 2009).

URL nslij-genetics.org/search_omim.html, Online Mendelian Inheritance in Man database, Center for Medical Genetics, Johns Hopkins University (Baltimore, MD) and National Center for Biotechnology Information, National Library of Medicine (Bethesda, MD). (As printed on Sep. 18, 2009).

URL qiagen.com, Qiagen RNeasy Mini Kit. (As p rinted on Sep. 18, 2009).

URL rana.lbl.gov/EisenSoftware.htm, "Cluster" software. (As printed on Sep. 18, 2009).

Home page from URL: web.archive.org/web/20070228190312/ http://systemsbiology.ucsd.edu, obtained on Sep. 18, 2009.

Two pages from URL: web.archive.org/web/20060712190022/ http://www.tigr.org/. The Institute for Genome Research, J. Craig Venter Institute; obtained on Sep. 18, 2009.

Home page from URL: web.archive.org/web/20021126044821/ http://tula.cifn.unam.mx:885O/regulondb/regulon_intro.frameset; obtained on Sep. 18, 2009.

URL wit.mcs.anl.gov/WIT (As printed Sep. 18, 2009).

URL workbench.sdsc.edu/ Biology Workbench. (As printed on Sep. 18, 2009).

Home pages from URL: web.archive.org/web/20041125063300/ http://wit.acs.anl.org; What is There (WIT), Obtained Nov. 23, 2008.

Schaff et al., "The Virtual Cell" Proceedings of the Pacific Symposiurm on Biocomputing (1999) pp. 228-239, XP002942953.

* cited by examiner

| Mass Balances | Flux Constraints |
|---|---|
| $G: R_1 - R_2 - R_4 = 0$ | $0 \leq R_1 \leq \infty$ |
| $B: R_2 - R_3 = 0$ | $-\infty \leq R_2 \leq \infty$ |
| $C: R_4 - R_5 = 0$ | $0 \leq R_3 \leq \infty$ |
| $D: R_5 - V_{growth} = 0$ | $0 \leq R_4 \leq \infty$ |
| $E: R_5 - R_6 = 0$ | $0 \leq R_5 \leq \infty$ |
| $F: 2R_3 - V_{growth} = 0$ | $0 \leq R_6 \leq \infty$ |
| $A_{external} : -A_{xt} - R_1 = 0$ | $0 \leq V_{growth} \leq \infty$ |
| $E_{external} : R_6 - E_{xt} = 0$ | $Y_1 \leq A_{xt} \leq Y_1$ |
|  | $-\infty \leq E_{xt} \leq 0$ |
| Objective Function $Z = V_{growth}$ ||

FIGURE 2

$$\begin{bmatrix} 0 \\ 0 \\ 0 \\ 0 \\ 0 \\ 0 \\ 0 \\ 0 \end{bmatrix} = \begin{bmatrix} R_1 \\ R_2 \\ R_3 \\ R_4 \\ R_5 \\ R_6 \\ V_{growth} \\ A_{xt} \\ E_{xt} \end{bmatrix}$$

|  | $R_1$ | $R_2$ | $R_3$ | $R_4$ | $R_5$ | $R_6$ | $V_{growth}$ | $A_{xt}$ | $E_{xt}$ |
|---|---|---|---|---|---|---|---|---|---|
| B | 0 | 1 | -1 | 0 | 0 | 0 | 0 | 0 | 0 |
| C | 0 | 0 | 0 | 1 | -1 | 0 | 0 | 0 | 0 |
| D | 0 | 0 | 0 | 0 | 1 | 0 | -1 | 0 | 0 |
| E | 0 | 0 | 0 | 0 | 1 | 1 | 0 | 0 | 0 |
| F | 0 | 0 | 2 | 0 | 0 | 0 | -1 | 0 | 0 |
| G | 1 | -1 | 0 | -1 | 0 | 0 | 0 | 0 | 0 |
| $A_{external}$ | -1 | 0 | 0 | 0 | 0 | 1 | 0 | -1 | 0 |
| $E_{external}$ | 0 | 0 | 0 | 0 | 0 | 0 | 0 | 0 | -1 |

FIGURE 3

HUMAN METABOLIC MODELS AND METHODS

This application claims benefit of the filing date of U.S. Provisional Application No. 60/368,588, filed Mar. 29, 2002, and which is incorporated herein by reference.

BACKGROUND OF THE INVENTION

This invention relates generally to analysis of the activity of chemical reaction networks and, more specifically, to computational methods for simulating and predicting the activity of *Homo sapiens* reaction networks.

Therapeutic agents, including drugs and gene-based agents, are being rapidly developed by the pharmaceutical industry with the goal of preventing or treating human disease. Dietary supplements, including herbal products, vitamins and amino acids, are also being developed and marketed by the nutraceutical industry. Because of the complexity of the biochemical reaction networks in and between human cells, even relatively minor perturbations caused by a therapeutic agent or a dietary component in the abundance or activity of a particular target, such as a metabolite, gene or protein, can affect hundreds of biochemical reactions. These perturbations can lead to desirable therapeutic effects, such as cell stasis or cell death in the case of cancer cells or other pathologically hyperproliferative cells. However, these perturbations can also lead to undesirable side effects, such as production of toxic byproducts, if the systemic effects of the perturbations are not taken into account.

Current approaches to drug and nutraceutical development do not take into account the effect of a perturbation in a molecular target on systemic cellular behavior. In order to design effective methods of repairing, engineering or disabling cellular activities, it is essential to understand human cellular behavior from an integrated perspective.

Cellular metabolism, which is an example of a process involving a highly integrated network of biochemical reactions, is fundamental to all normal cellular or physiological processes, including homeostatis, proliferation, differentiation, programmed cell death (apoptosis) and motility. Alterations in cellular metabolism characterize a vast number of human diseases. For example, tissue injury is often characterized by increased catabolism of glucose, fatty acids and amino acids, which, if persistent, can lead to organ dysfunction. Conditions of low oxygen supply (hypoxia) and nutrient supply, such as occur in solid tumors, result in a myriad of adaptive metabolic changes including activation of glycolysis and neovascularization. Metabolic dysfunctions also contribute to neurodegenerative diseases, cardiovascular disease, neuromuscular diseases, obesity and diabetes. Currently, despite the importance of cellular metabolism to normal and pathological processes, a detailed systemic understanding of cellular metabolism in human cells is currently lacking.

Thus, there exists a need for models that describe *Homo sapiens* reaction networks, including core metabolic reaction networks and metabolic reaction networks in specialized cell types, which can be used to simulate different aspects of human cellular behavior under physiological, pathological and therapeutic conditions. The present invention satisfies this need, and provides related advantages as well.

SUMMARY OF THE INVENTION

The invention provides a computer readable medium or media, including: (a) a data structure relating a plurality of *Homo sapiens* reactants to a plurality of *Homo sapiens* reactions, wherein each of the *Homo sapiens* reactions includes a reactant identified as a substrate of the reaction, a reactant identified as a product of the reaction and a stoichiometric coefficient relating the substrate and the product, (b) a constraint set for the plurality of *Homo sapiens* reactions, and (c) commands for determining at least one flux distribution that minimizes or maximizes an objective function when the constraint set is applied to the data representation, wherein the at least one flux distribution is predictive of a *Homo sapiens* physiological function. In one embodiment, at least one of the *Homo sapiens* reactions in the data structure is annotated to indicate an associated gene and the computer readable medium or media further includes a gene database including information characterizing the associated gene. In another embodiment, at least one of the *Homo sapiens* reactions is a regulated reaction and the computer readable medium or media further includes a constraint set for the plurality of *Homo sapiens* reactions, wherein the constraint set includes a variable constraint for the regulated reaction.

The invention provides a method for predicting a *Homo sapiens* physiological function, including: (a) providing a data structure relating a plurality of *Homo sapiens* reactants to a plurality of *Homo sapiens* reactions, wherein each of the *Homo sapiens* reactions includes a reactant identified as a substrate of the reaction, a reactant identified as a product of the reaction and a stoichiometric coefficient relating the substrate and the product; (b) providing a constraint set for the plurality of *Homo sapiens* reactions; (c) providing an objective function, and (d) determining at least one flux distribution that minimizes or maximizes the objective function when the constraint set is applied to the data structure, thereby predicting a *Homo sapiens* physiological function. In one embodiment, at least one of the *Homo sapiens* reactions in the data structure is annotated to indicate an associated gene and the method predicts a *Homo sapiens* physiological function related to the gene.

The invention provides a method for predicting a *Homo sapiens* physiological function, including: (a) providing a data structure relating a plurality of *Homo sapiens* reactants to a plurality of *Homo sapiens* reactions, wherein each of the *Homo sapiens* reactions includes a reactant identified as a substrate of the reaction, a reactant identified as a product of the reaction and a stoichiometric coefficient relating the substrate and the product, wherein at least one of the *Homo sapiens* reactions is a regulated reaction; (b) providing a constraint set for the plurality of *Homo sapiens* reactions, wherein the constraint set includes a variable constraint for the regulated reaction; (c) providing a condition-dependent value to the variable constraint; (d) providing an objective function, and (e) determining at least one flux distribution that minimizes or maximizes the objective function when the constraint set is applied to the data structure, thereby predicting a *Homo sapiens* physiological function.

Also provided by the invention is a method for making a data structure relating a plurality of *Homo sapiens* reactants to a plurality of *Homo sapiens* reactions in a computer readable medium or media, including: (a) identifying a plurality of *Homo sapiens* reactions and a plurality of *Homo sapiens* reactants that are substrates and products of the *Homo sapiens* reactions; (b) relating the plurality of *Homo sapiens* reactants to the plurality of *Homo sapiens* reactions in a data structure, wherein each of the *Homo sapiens* reactions includes a reactant identified as a substrate of the reaction, a reactant identified as a product of the reaction and a stoichiometric coefficient relating the substrate and the product; (c) determining a constraint set for the plurality of *Homo sapiens* reactions; (d) providing an objective function; (e) determining at least one flux distribution that minimizes or maximizes the objective function when the constraint set is applied to the data structure, and (f) if the at least one flux distribution is not predictive of a *Homo sapiens* physiological function, then adding a reaction to or deleting a reaction from the data structure and repeating step (e), if the at least one flux distribution is predictive of a *Homo sapiens* physiological function, then storing the data structure in a computer readable medium or media. The invention further provides a data structure relating a plurality of *Homo sapiens* reactants to a plurality of *Homo sapiens* reactions, wherein the data structure is produced by the method.

BRIEF DESCRIPTION OF THE DRAWINGS

FIG. 2 shows mass balance constraints and flux constraints (reversibility constraints) that can be placed on the hypothetical metabolic network shown in FIG. 1.

FIG. 3 shows the stoichiometric matrix (S) for the hypothetical metabolic network shown in FIG. 1.

DETAILED DESCRIPTION OF THE INVENTION

Figure 1:
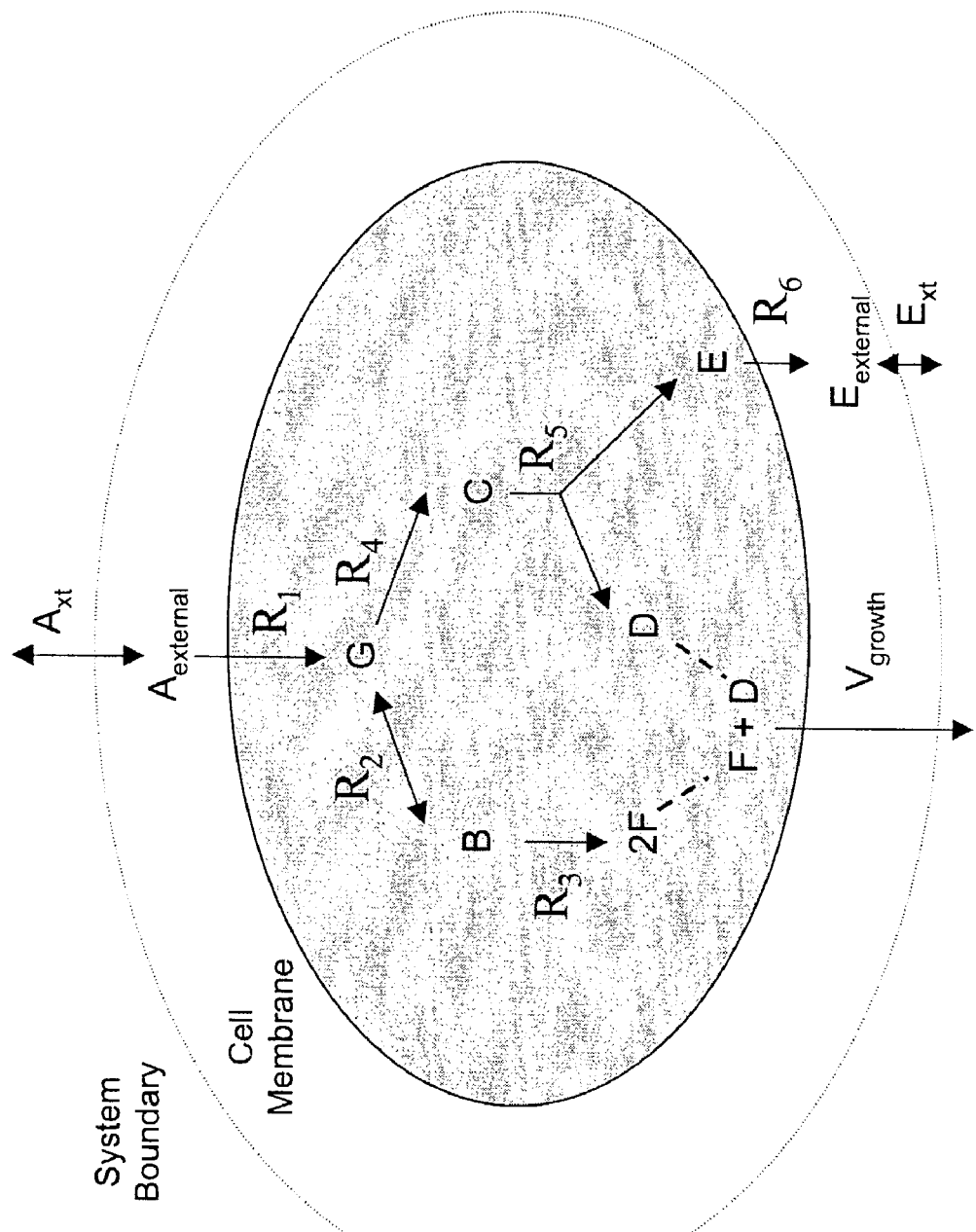
FIG. 1 shows a schematic representation of a hypothetical metabolic network.

The present invention provides in silico models that describe the interconnections between genes in the *Homo sapiens* genome and their associated reactions and reactants. The models can be used to simulate different aspects of the cellular behavior of human cells under different normal, pathological and therapeutic conditions, thereby providing valuable information for therapeutic, diagnostic and research applications. An advantage of the models of the invention is that they provide a holistic approach to simulating and predicting the activity of *Homo sapiens* cells. The models and methods can also be extended to simulate the activity of multiple interacting cells, including organs, physiological systems and whole body metabolism.

As an example, the *Homo sapiens* metabolic models of the invention can be used to determine the effects of changes from aerobic to anaerobic conditions, such as occurs in skeletal muscles during exercise or in tumors, or to determine the effect of various dietary changes. The *Homo sapiens* metabolic models can also be used to determine the consequences of genetic defects, such as deficiencies in metabolic enzymes such as phosphofructokinase, phosphoglycerate kinase, phosphoglycerate mutase, lactate dehydrogenase and adenosine deaminase.

The *Homo sapiens* metabolic models can also be used to choose appropriate targets for drug design. Such targets include genes, proteins or reactants, which when modulated positively or negatively in a simulation produce a desired therapeutic result. The models and methods of the invention can also be used to predict the effects of a therapeutic agent or dietary supplement on a cellular function of interest. Likewise, the models and methods can be used to predict both desirable and undesirable side effects of the therapeutic agent on an interrelated cellular function in the target cell, as well as the desirable and undesirable effects that may occur in other cell types. Thus, the models and methods of the invention can make the drug development process more rapid and cost effective than is currently possible.

The *Homo sapiens* metabolic models can also be used to predict or validate the assignment of particular biochemical reactions to the enzyme-encoding genes found in the genome, and to identify the presence of reactions or pathways not indicated by current genomic data. Thus, the models can be used to guide the research and discovery process, potentially leading to the identification of new enzymes, medicines or metabolites of clinical importance.

The models of the invention are based on a data structure relating a plurality of *Homo sapiens* reactants to a plurality of *Homo sapiens* reactions, wherein each of the *Homo sapiens* reactions includes a reactant identified as a substrate of the reaction, a reactant identified as a product of the reaction and a stoichiometric coefficient relating the substrate and the product. The reactions included in the data structure can be those that are common to all or most *Homo sapiens* cells, such as core metabolic reactions, or reactions specific for one or more given cell type.

As used herein, the term "*Homo sapiens* reaction" is intended to mean a conversion that consumes a substrate or forms a product that occurs in or by a *Homo sapiens* cell. The term can include a conversion that occurs due to the activity of one or more enzymes that are genetically encoded by a *Homo sapiens* genome. The term can also include a conversion that occurs spontaneously in a *Homo sapiens* cell. Conversions included in the term include, for example, changes in chemical composition such as those due to nucleophilic or electrophilic addition, nucleophilic or electrophilic substitution, elimination, isomerization, deamination, phosphorylation, methylation, reduction, oxidation or changes in location such as those that occur due to a transport reaction that moves a reactant from one cellular compartment to another. In the case of a transport reaction, the substrate and product of the reaction can be chemically the same and the substrate and product can be differentiated according to location in a particular cellular compartment. Thus, a reaction that transports a chemically unchanged reactant from a first compartment to a second compartment has as its substrate the reactant in the first compartment and as its product the reactant in the second compartment. It will be understood that when used in reference to an in silico model or data structure, a reaction is intended to be a representation of a chemical conversion that consumes a substrate or produces a product.

As used herein, the term "*Homo sapiens* reactant" is intended to mean a chemical that is a substrate or a product of a reaction that occurs in or by a *Homo sapiens* cell. The term can include substrates or products of reactions performed by one or more enzymes encoded by a *Homo sapiens* genome, reactions occurring in *Homo sapiens* that are performed by one or more non-genetically encoded macromolecule, protein or enzyme, or reactions that occur spontaneously in a *Homo sapiens* cell. Metabolites are understood to be reactants within the meaning of the term. It will be understood that when used in reference to an in silico model or data structure, a reactant is intended to be a representation of a chemical that is a substrate or a product of a reaction that occurs in or by a *Homo sapiens* cell.

As used herein the term "substrate" is intended to mean a reactant that can be converted to one or more products by a reaction. The term can include, for example, a reactant that is to be chemically changed due to nucleophilic or electrophilic addition, nucleophilic or electrophilic substitution, elimination, isomerization, deamination, phosphorylation, methylation, reduction, oxidation or that is to change location such as by being transported across a membrane or to a different compartment.

As used herein, the term "product" is intended to mean a reactant that results from a reaction with one, or more substrates. The term can include, for example, a reactant that has been chemically changed due to nucleophilic or electrophilic addition, nucleophilic or electrophilic substitution, elimination, isomerization, deamination, phosphorylation, methylation, reduction or oxidation or that has changed location such as by being transported across a membrane or to a different compartment.

As used herein, the term "stoichiometric coefficient" is intended to mean a numerical constant correlating the number of one or more reactants and the number of one or more products in a chemical reaction. Typically, the numbers are integers as they denote the number of molecules of each reactant in an elementally balanced chemical equation that describes the corresponding conversion. However, in some cases the numbers can take on non-integer values, for example, when used in a lumped reaction or to reflect empirical data.

As used herein, the term "plurality," when used in reference to *Homo sapiens* reactions or reactants, is intended to mean at least 2 reactions or reactants. The term can include any number of *Homo sapiens* reactions or reactants in the range from 2 to the number of naturally occurring reactants or reactions for a particular of *Homo sapiens* cell. Thus, the term can include, for example, at least 10, 20, 30, 50, 100, 150, 200, 300, 400, 500, 600 or more reactions or reactants. The number of reactions or reactants can be expressed as a portion of the total number of naturally occurring reactions for a particular *Homo sapiens* cell, such as at least 20%, 30%, 50%, 60%, 75%, 90%, 95% or 98% of the total number of naturally occurring reactions that occur in a particular *Homo sapiens* cell.

As used herein, the term "data structure" is intended to mean a physical or logical relationship among data elements, designed to support specific data manipulation functions. The term can include, for example, a list of data elements that can be added combined or otherwise manipulated such as a list of representations for reactions from which reactants can be related in a matrix or network. The term can also include a matrix that correlates data elements from two or more lists of information such as a matrix that correlates reactants to reactions. Information included in the term can represent, for example, a substrate or product of a chemical reaction, a chemical reaction relating one or more substrates to one or more products, a constraint placed on a reaction, or a stoichiometric coefficient.

As used herein, the term "constraint" is intended to mean an upper or lower boundary for a reaction. A boundary can specify a minimum or maximum flow of mass, electrons or energy through a reaction. A boundary can further specify directionality of a reaction. A boundary can be a constant value such as zero, infinity, or a numerical value such as an integer. Alternatively, a boundary can be a variable boundary value as set forth below.

As used herein, the term "variable," when used in reference to a constraint is intended to mean capable of assuming any of a set of values in response to being acted upon by a constraint function. The term "function," when used in the context of a constraint, is intended to be consistent with the meaning of the term as it is understood in the computer and mathematical arts. A function can be binary such that changes correspond to a reaction being off or on. Alternatively, continuous functions can be used such that changes in boundary values correspond to increases or decreases in activity. Such increases or decreases can also be binned or effectively digitized by a function capable of converting sets of values to discreet integer values. A function included in the term can correlate a boundary value with the presence, absence or amount of a biochemical reaction network participant such as a reactant, reaction, enzyme or gene. A function included in the term can correlate a boundary value with an outcome of at least one reaction in a reaction network that includes the reaction that is constrained by the boundary limit. A function included in the term can also correlate a boundary value with an environmental condition such as time, pH, temperature or redox potential.

As used herein, the term "activity," when used in reference to a reaction, is intended to mean the amount of product produced by the reaction, the amount of substrate consumed by the reaction or the rate at which a product is produced or a substrate is consumed. The amount of product produced by the reaction, the amount of substrate consumed by the reaction or the rate at which a product is produced or a substrate is consumed can also be referred to as the flux for the reaction.

As used herein, the term "activity," when used in reference to a *Homo sapiens* cell, is intended to mean the magnitude or rate of a change from an initial state to a final state. The term can include, for example, the amount of a chemical consumed or produced by a cell, the rate at which a chemical is consumed or produced by a cell, the amount or rate of growth of a cell or the amount of or rate at which energy, mass or electrons flow through a particular subset of reactions.

The invention provides a computer readable medium, having a data structure relating a plurality of *Homo sapiens* reactants to a plurality of *Homo sapiens* reactions, wherein each of the *Homo sapiens* reactions includes a reactant identified as a substrate of the reaction, a reactant identified as a product of the reaction and a stoichiometric coefficient relating the substrate and the product.

Depending on the application, the plurality of *Homo sapiens* reactions can include reactions selected from core metabolic reactions or peripheral metabolic reactions. As used herein, the term "core," when used in reference to a metabolic pathway, is intended to mean a metabolic pathway selected from glycolysis/gluconeogenesis, the pentose phosphate pathway (PPP), the tricarboxylic acid (TCA) cycle, glycogen storage, electron transfer system (ETS), the malate/aspartate shuttle, the glycerol phosphate shuttle, and plasma and mitochondrial membrane transporters. As used herein, the term "peripheral," when used in reference to a metabolic pathway, is intended to mean a metabolic pathway that includes one or more reactions that are not a part of a core metabolic pathway.

A plurality of *Homo sapiens* reactants can be related to a plurality of *Homo sapiens* reactions in any data structure that represents, for each reactant, the reactions by which it is consumed or produced. Thus, the data structure, which is referred to herein as a "reaction network data structure," serves as a representation of a biological reaction network or system. An example of a reaction network that can be represented in a reaction network data structure of the invention is the collection of reactions that constitute the core metabolic reactions of *Homo sapiens*, or the metabolic reactions of a skeletal muscle cell, as shown in the Examples.

The choice of reactions to include in a particular reaction network data structure, from among all the possible reactions that can occur in human cells, depends on the cell type or types and the physiological, pathological or therapeutic condition being modeled, and can be determined experimentally or from the literature, as described further below.

The reactions to be included in a particular network data structure of *Homo sapiens* can be determined experimentally using, for example, gene or protein expression profiles, where the molecular characteristics of the cell can be correlated to the expression levels. The expression or lack of expression of genes or proteins in a cell type can be used in determining whether a reaction is included in the model by association to the expressed gene(s) and or protein(s). Thus, it is possible to use experimental technologies to determine which genes and/or proteins are expressed in a specific cell type, and to further use this information to determine which reactions are present in the cell type of interest. In this way a subset of reactions from all of those reactions that can occur in human cells are selected to comprise the set of reactions that represent a specific cell type. cDNA expression profiles have been demonstrated to be useful, for example, for classification of breast cancer cells (Sorlie et al., *Proc. Natl. Acad. Sci. U.S.A.* 98(19): 10869-10874 (2001)).

The methods and models of the invention can be applied to any *Homo sapiens* cell type at any stage of differentiation, including, for example, embryonic stem cells, hematopoietic stem cells, differentiated hematopoietic cells, skeletal muscle cells, cardiac muscle cells, smooth muscle cells, skin cells, nerve cells, kidney cells, pulmonary cells, liver cells, adipocytes and endocrine cells (e.g. beta islet cells of the pancreas, mammary gland cells, adrenal cells, and other specialized hormone secreting cells).

The methods and models of the invention can be applied to normal cells or pathological cells. Normal cells that exhibit a variety of physiological activities of interest, including homeostasis, proliferation, differentiation, apoptosis, contraction and motility, can be modeled. Pathological cells can also be modeled, including cells that reflect genetic or developmental abnormalities, nutritional deficiencies, environmental assaults, infection (such as by bacteria, viral, protozoan or fungal agents), neoplasia, aging, altered immune or endocrine function, tissue damage, or any combination of these factors. The pathological cells can be representative of any type of human pathology, including, for example, various metabolic disorders of carbohydrate, lipid or protein metabolism, obesity, diabetes, cardiovascular disease, fibrosis, various cancers, kidney failure, immune pathologies, neurodegenerative diseases, and various monogenetic metabolic diseases described in the Online Mendelian Inheritance in Man database (Center for Medical Genetics, Johns Hopkins University (Baltimore, Md.) and National Center for Biotechnology Information, National Library of Medicine (Bethesda, Md.)).

The methods and models of the invention can also be applied to cells undergoing therapeutic perturbations, such as cells treated with drugs that target participants in a reaction network, cells treated with gene-based therapeutics that increase or decrease expression of an encoded protein, and cells treated with radiation. As used herein, the term "drug" refers to a compound of any molecular nature with a known or proposed therapeutic function, including, for example, small molecule compounds, peptides and other macromolecules, peptidomimetics and antibodies, any of which can optionally be tagged with cytostatic, targeting or detectable moieties. The term "gene-based therapeutic" refers to nucleic acid therapeutics, including, for example, expressible genes with normal or altered protein activity, antisense compounds, ribozymes, DNAzymes, RNA interference compounds (RNAi) and the like. The therapeutics can target any reaction network participant, in any cellular location, including participants in extracellular, cell surface, cytoplasmic, mitochondrial and nuclear locations. Experimental data that are gathered on the response of cells to therapeutic treatment, such as alterations in gene or protein expression profiles, can be used to tailor a network for a pathological state of a particular cell type.

The methods and models of the invention can be applied to *Homo sapiens* cells as they exist in any form, such as in primary cell isolates or in established cell lines, or in the whole body, in intact organs or in tissue explants. Accordingly, the methods and models can take into account intercellular communications and/or inter-organ communications, the effect of adhesion to a substrate or neighboring cells (such as a stem cell interacting with mesenchymal cells or a cancer cell interacting with its tissue microenvironment, or beta-islet cells without normal stroma), and other interactions relevant to multicellular systems.

The reactants to be used in a reaction network data structure of the invention can be obtained from or stored in a compound database. As used herein, the term "compound database" is intended to mean a computer readable medium or media containing a plurality of molecules that includes substrates and products of biological reactions. The plurality of molecules can include molecules found in multiple organisms, thereby constituting a universal compound database. Alternatively, the plurality of molecules can be limited to those that occur in a particular organism, thereby constituting an organism-specific compound database. Each reactant in a compound database can be identified according to the chemical species and the cellular compartment in which it is present. Thus, for example, a distinction can be made between glucose in the extracellular compartment versus glucose in the cytosol. Additionally each of the reactants can be specified as a metabolite of a primary or secondary metabolic pathway. Although identification of a reactant as a metabolite of a primary or secondary metabolic pathway does not indicate any chemical distinction between the reactants in a reaction, such a designation can assist in visual representations of large networks of reactions.

As used herein, the term "compartment" is intended to mean a subdivided region containing at least one reactant, such that the reactant is separated from at least one other reactant in a second region. A subdivided region included in the term can be correlated with a subdivided region of a cell. Thus, a subdivided region included in the term can be, for example, the intracellular space of a cell; the extracellular space around a cell; the periplasmic space, the interior space of an organelle such as a mitochondrium, endoplasmic reticulum, Golgi apparatus, vacuole or nucleus; or any subcellular space that is separated from another by a membrane or other physical barrier. Subdivided regions can also be made in order to create virtual boundaries in a reaction network that are not correlated with physical barriers. Virtual boundaries can be made for the purpose of segmenting the reactions in a network into different compartments or substructures.

As used herein, the term "substructure" is intended to mean a portion of the information in a data structure that is separated from other information in the data structure such that the portion of information can be separately manipulated or analyzed. The term can include portions subdivided according to a biological function including, for example, information relevant to a particular metabolic pathway such as an internal flux pathway, exchange flux pathway, central metabolic pathway, peripheral metabolic pathway, or secondary metabolic pathway. The term can include portions subdivided according to computational or mathematical principles that allow for a particular type of analysis or manipulation of the data structure.

The reactions included in a reaction network data structure can be obtained from a metabolic reaction database that includes the substrates, products, and stoichiometry of a plurality of metabolic reactions of *Homo sapiens*. The reactants in a reaction network data structure can be designated as either substrates or products of a particular reaction, each with a stoichiometric coefficient assigned to it to describe the chemical conversion taking place in the reaction. Each reaction is also described as occurring in either a reversible or irreversible direction. Reversible reactions can either be represented as one reaction that operates in both the forward and reverse direction or be decomposed into two irreversible reactions, one corresponding to the forward reaction and the other corresponding to the backward reaction.

Reactions included in a reaction network data structure can include intra-system or exchange reactions. Intra-system reactions are the chemically and electrically balanced interconversions of chemical species and transport processes, which serve to replenish or drain the relative amounts of certain metabolites. These intra-system reactions can be classified as either being transformations or translocations. A transformation is a reaction that contains distinct sets of compounds as substrates and products, while a translocation contains reactants located in different compartments. Thus a reaction that simply transports a metabolite from the extracellular environment to the cytosol, without changing its chemical composition is solely classified as a translocation, while a reaction that takes an extracellular substrate and converts it into a cytosolic product is both a translocation and a transformation.

Exchange reactions are those which constitute sources and sinks, allowing the passage of metabolites into and out of a compartment or across a hypothetical system boundary. These reactions are included in a model for simulation purposes and represent the metabolic demands placed on *Homo sapiens*. While they may be chemically balanced in certain cases, they are typically not balanced and can often have only a single substrate or product. As a matter of convention the exchange reactions are further classified into demand exchange and input/output exchange reactions.

The metabolic demands placed on the *Homo sapiens* metabolic reaction network can be readily determined from the dry weight composition of the cell which is available in the published literature or which can be determined experimentally. The uptake rates and maintenance requirements for *Homo sapiens* cells can also be obtained from the published literature or determined experimentally.

Input/output exchange reactions are used to allow extracellular reactants to enter or exit the reaction network represented by a model of the invention. For each of the extracellular metabolites a corresponding input/output exchange reaction can be created. These reactions are always reversible with the metabolite indicated as a substrate with a stoichiometric coefficient of one and no products produced by the reaction. This particular convention is adopted to allow the reaction to take on a positive flux value (activity level) when the metabolite is being produced or removed from the reaction network and a negative flux value when the metabolite is being consumed or introduced into the reaction network. These reactions will be further constrained during the course of a simulation to specify exactly which metabolites are available to the cell and which can be excreted by the cell.

A demand exchange reaction is always specified as an irreversible reaction containing at least one substrate. These reactions are typically formulated to represent the production of an intracellular metabolite by the metabolic network or the aggregate production of many reactants in balanced ratios such as in the representation of a reaction that leads to biomass formation, also referred to as growth.

A demand exchange reactions can be introduced for any metabolite in a model of the invention. Most commonly these reactions are introduced for metabolites that are required to be produced by the cell for the purposes of creating a new cell such as amino acids, nucleotides, phospholipids, and other biomass constituents, or metabolites that are to be produced for alternative purposes. Once these metabolites are identified, a demand exchange reaction that is irreversible and specifies the metabolite as a substrate with a stoichiometric coefficient of unity can be created. With these specifications, if the reaction is active it leads to the net production of the metabolite by the system meeting potential production demands. Examples of processes that can be represented as a demand exchange reaction in a reaction network data structure and analyzed by the methods of the invention include, for example, production or secretion of an individual protein; production or secretion of an individual metabolite such as an amino acid, vitamin, nucleoside, antibiotic or surfactant; production of ATP for extraneous energy requiring processes such as locomotion; or formation of biomass constituents.

In addition to these demand exchange reactions that are placed on individual metabolites, demand exchange reactions that utilize multiple metabolites in defined stoichiometric ratios can be introduced. These reactions are referred to as aggregate demand exchange reactions. An example of an aggregate demand reaction is a reaction used to simulate the concurrent growth demands or production requirements associated with cell growth that are placed on a cell, for example, by simulating the formation of multiple biomass constituents simultaneously at a particular cellular growth rate.

A hypothetical reaction network is provided in FIG. 1 to exemplify the above-described reactions and their interactions. The reactions can be represented in the exemplary data structure shown in FIG. 3 as set forth below. The reaction network, shown in FIG. 1, includes intrasystem reactions that occur entirely within the compartment indicated by the shaded oval such as reversible reaction $R_2$ which acts on reactants B and G and reaction $R_3$ which converts one equivalent of B to 2 equivalents of F. The reaction network shown in FIG. 1 also contains exchange reactions such as input/output exchange reactions $A_{xt}$ and $E_{xt}$, and the demand exchange reaction, $V_{growth}$, which represents growth in response to the one equivalent of D and one equivalent of F. Other intrasystem reactions include $R_1$ which is a translocation and transformation reaction that translocates reactant A into the compartment and transforms it to reactant G and reaction $R_6$ which is a transport reaction that translocates reactant E out of the compartment.

A reaction network can be represented as a set of linear algebraic equations which can be presented as a stoichiometric matrix S, with S being an m x n matrix where m corresponds to the number of reactants or metabolites and n corresponds to the number of reactions taking place in the network. An example of a stoichiometric matrix representing the reaction network of FIG. 1 is shown in FIG. 3. As shown in FIG. 3, each column in the matrix corresponds to a particular reaction n, each row corresponds to a particular reactant m, and each $S_{mn}$ element corresponds to the stoichiometric coefficient of the reactant m in the reaction denoted n. The stoichiometric matrix includes intra-system reactions such as $R_2$ and $R_3$ which are related to reactants that participate in the respective reactions according to a stoichiometric coefficient having a sign indicative of whether the reactant is a substrate or product of the reaction and a value correlated with the number of equivalents of the reactant consumed or produced by the reaction. Exchange reactions such as $-E_{xt}$ and $-A_{xt}$ are similarly correlated with a stoichiometric coefficient. As exemplified by reactant E, the same compound can be treated separately as an internal reactant (E) and an external reactant ($E_{external}$) such that an exchange reaction ($R_6$) exporting the compound is correlated by stoichiometric coefficients of −1 and 1, respectively. However, because the compound is treated as a separate reactant by virtue of its compartmental location, a reaction, such as $R_5$, which produces the internal reactant (E) but does not act on the external reactant ($E_{external}$) is correlated by stoichiometric coefficients of 1 and 0, respectively. Demand reactions such as $V_{growth}$ can also be included in the stoichiometric matrix being correlated with substrates by an appropriate stoichiometric coefficient.

As set forth in further detail below, a stoichiometric matrix provides a convenient format for representing and analyzing a reaction network because it can be readily manipulated and used to compute network properties, for example, by using linear programming or general convex analysis. A reaction network data structure can take on a variety of formats so long as it is capable of relating reactants and reactions in the manner exemplified above for a stoichiometric matrix and in a manner that can be manipulated to determine an activity of one or more reactions using methods such as those exemplified below. Other examples of reaction network data structures that are useful in the invention include a connected graph, list of chemical reactions or a table of reaction equations.

A reaction network data structure can be constructed to include all reactions that are involved in *Homo sapiens* metabolism or any portion thereof. A portion of *Homo sapiens* metabolic reactions that can be included in a reaction network data structure of the invention includes, for example, a central metabolic pathway such as glycolysis, the TCA cycle, the PPP or ETS; or a peripheral metabolic pathway such as amino acid biosynthesis, amino acid degradation, purine biosynthesis, pyrimidine biosynthesis, lipid biosynthesis, fatty acid metabolism, vitamin or cofactor biosynthesis, transport processes and alternative carbon source catabolism. Examples of individual pathways within the peripheral pathways are set forth in Table 1.

Depending upon a particular application, a reaction network data structure can include a plurality of *Homo sapiens* reactions including any or all of the reactions listed in Table 1.

For some applications, it can be advantageous to use a reaction network data structure that includes a minimal number of reactions to achieve a particular *Homo sapiens* activity under a particular set of environmental conditions. A reaction network data structure having a minimal number of reactions can be identified by performing the simulation methods described below in an iterative fashion where different reactions or sets of reactions are systematically removed and the effects observed. Accordingly, the invention provides a computer readable medium, containing a data structure relating a plurality of *Homo sapiens* reactants to a plurality of *Homo sapiens* reactions, wherein the plurality of *Homo sapiens* reactions contains at least 65 reactions. For example, the core metabolic reaction database shown in Tables 2 and 3 contains 65 reactions, and is sufficient to simulate aerobic and anaerobic metabolism on a number of carbon sources, including glucose.

Depending upon the particular cell type or types, the physiological, pathological or therapeutic conditions being tested and the desired activity, a reaction network data structure can contain smaller numbers of reactions such as at least 200, 150, 100 or 50 reactions. A reaction network data structure having relatively few reactions can provide the advantage of reducing computation time and resources required to perform a simulation. When desired, a reaction network data structure having a particular subset of reactions can be made or used in which reactions that are not relevant to the particular simulation are omitted. Alternatively, larger numbers of reactions can be included in order to increase the accuracy or molecular detail of the methods of the invention or to suit a particular application. Thus, a reaction network data structure can contain at least 300, 350, 400, 450, 500, 550, 600 or more reactions up to the number of reactions that occur in or by *Homo sapiens* or that are desired to simulate the activity of the full set of reactions occurring in *Homo sapiens*. A reaction network data structure that is substantially complete with respect to the metabolic reactions of *Homo sapiens* provides the advantage of being relevant to a wide range of conditions to be simulated, whereas those with smaller numbers of metabolic reactions are limited to a particular subset of conditions to be simulated.

A *Homo sapiens* reaction network data structure can include one or more reactions that occur in or by *Homo sapiens* and that do not occur, either naturally or following manipulation, in or by another organism, such as *Saccharomiyces cerevisiae*. It is understood that a *Homo sapiens* reaction network data structure of a particular cell type can also include one or more reactions that occur in another cell type. Addition of such heterologous reactions to a reaction network data structure of the invention can be used in methods to predict the consequences of heterologous gene transfer and protein expression, for example, when designing in vivo and ex vivo gene therapy approaches.

The reactions included in a reaction network data structure of the invention can be metabolic reactions. A reaction network data structure can also be constructed to include other types of reactions such as regulatory reactions, signal transduction reactions, cell cycle reactions, reactions controlling developmental processes, reactions involved in apoptosis, reactions involved in responses to hypoxia, reactions involved in responses to cell-cell or cell-substrate interactions, reactions involved in protein synthesis and regulation thereof, reactions involved in gene transcription and translation, and regulation thereof, and reactions involved in assembly of a cell and its subcellular components.

A reaction network data structure or index of reactions used in the data structure such as that available in a metabolic reaction database, as described above, can be annotated to include information about a particular reaction. A reaction can be annotated to indicate, for example, assignment of the reaction to a protein, macromolecule or enzyme that performs the reaction, assignment of a gene(s) that codes for the protein, macromolecule or enzyme, the Enzyme Commission (EC) number of the particular metabolic reaction, a subset of reactions to which the reaction belongs, citations to references from which information was obtained, or a level of confidence with which a reaction is believed to occur in *Homo sapiens*. A computer readable medium or media of the invention can include a gene database containing annotated reactions. Such information can be obtained during the course of building a metabolic reaction database or model of the invention as described below.

As used herein, the term "gene database" is intended to mean a computer readable medium or media that contains at least one reaction that is annotated to assign a reaction to one or more macromolecules that perform the reaction or to assign one or more nucleic acid that encodes the one or more macromolecules that perform the reaction. A gene database can contain a plurality of reactions, some or all of which are annotated. An annotation can include, for example, a name for a macromolecule; assignment of a function to a macromolecule; assignment of an organism that contains the macromolecule or produces the macromolecule; assignment of a subcellular location for the macromolecule; assignment of conditions under which a macromolecule is regulated with respect to performing a reaction, being expressed or being degraded; assignment of a cellular component that regulates a macromolecule; an amino acid or nucleotide sequence for the macromolecule; or any other annotation found for a macromolecule in a genome database such as those that can be found in Genbank, a site maintained by the NCBI (ncbi.nlm.gov), the Kyoto Encyclopedia of Genes and Genomes (KEGG) (www.genome.ad.jp/kegg/), the protein database SWISS-PROT (ca.expasy.org/sprot/), the LocusLink database maintained by the NCBI (www.ncbi.nlm.nih.gov/LocusLink/), the Enzyme Nomenclature database maintained by G. P. Moss of Queen Mary and Westfield College in the United Kingdom (www.chem.qmw.ac.uk/iubmb/enzyme/).

A gene database of the invention can include a substantially complete collection of genes or open reading frames in *Homo sapiens* or a substantially complete collection of the macromolecules encoded by the *Homo sapiens* genome. Alternatively, a gene database can include a portion of genes or open reading frames in *Homo sapiens* or a portion of the macromolecules encoded by the *Homo sapiens* genome, such as the portion that includes substantially all metabolic genes or macromolecules. The portion can be at least 10%, 15%, 20%, 25%, 50%, 75%, 90% or 95% of the genes or open reading frames encoded by the *Homo sapiens* genome, or the macromolecules encoded therein. A gene database can also include macromolecules encoded by at least a portion of the nucleotide sequence for the *Homo sapiens* genome such as at least 10%, 15%, 20%, 25%, 50%, 75%, 90% or 95% of the *Homo sapiens* genome. Accordingly, a computer readable medium or media of the invention can include at least one reaction for each macromolecule encoded by a portion of the *Homo sapiens* genome.

An in silico *Homo sapiens* model of the invention can be built by an iterative process which includes gathering information regarding particular reactions to be added to a model, representing the reactions in a reaction network data structure, and performing preliminary simulations wherein a set of constraints is placed on the reaction network and the output evaluated to identify errors in the network. Errors in the network such as gaps that lead to non-natural accumulation or consumption of a particular metabolite can be identified as described below and simulations repeated until a desired performance of the model is attained. An exemplary method for iterative model construction is provided in Example I.

Thus, the invention provides a method for making a data structure relating a plurality of *Homo sapiens* reactants to a plurality of *Homo sapiens* reactions in a computer readable medium or media. The method includes the steps of: (a) identifying a plurality of *Homo sapiens* reactions and a plurality of *Homo sapiens* reactants that are substrates and products of the *Homo sapiens* reactions; (by relating the plurality of *Homo sapiens* reactants to the plurality of *Homo sapiens* reactions in a data structure, wherein each of the *Homo sapiens* reactions includes a reactant identified as a substrate of the reaction, a reactant identified as a product of the reaction and a stoichiometric coefficient relating the substrate and the product; (c) making a constraint set for the plurality of *Homo sapiens* reactions; (d) providing an objective function; (e) determining at least one flux distribution that minimizes or maximizes the objective function when the constraint set is applied to the data structure, and (f) if the at least one flux distribution is not predictive of *Homo sapiens* physiology, then adding a reaction to or deleting a reaction from the data structure and repeating step (e), if the at least one flux distribution is predictive of *Homo sapiens* physiology, then storing the data structure in a computer readable medium or media.

Information to be included in a data structure of the invention can be gathered from a variety of sources including, for example, annotated genome sequence information and biochemical literature.

Sources of annotated human genome sequence information include, for example, KEGG, SWISS-PROT, LocusLink, the Enzyme Nomenclature database, the International Human Genome Sequencing Consortium and commercial databases. KEGG contains a broad range of information, including a substantial amount of metabolic reconstruction. The genomes of 63 organisms can be accessed here, with gene products grouped by coordinated functions, often represented by a map (e.g., the enzymes involved in glycolysis would be grouped together). The maps are biochemical pathway templates which show enzymes connecting metabolites for various parts of metabolism. These general pathway templates are customized for a given organism by highlighting enzymes on a given template which have been identified in the genome of the organism. Enzymes and metabolites are active and yield useful information about stoichiometry, structure, alternative names and the like, when accessed.

SWISS-PROT contains detailed information about protein function. Accessible information includes alternate gene and gene product names, function, structure and sequence information, relevant literature references, and the like.

LocusLink contains general information about the locus where the gene is located and, of relevance, tissue specificity, cellular location, and implication of the gene product in various disease states.

The Enzyme Nomenclature database can be used to compare the gene products of two organisms. Often the gene names for genes with similar functions in two or more organisms are unrelated. When this is the case, the E. C. (Enzyme Commission) numbers can be used as unambiguous indicators of gene product function. The information in the Enzyme Nomenclature database is also published in Enzyme Nomenclature (Academic Press, San Diego, Calif., 1992) with 5 supplements to date, all found in the European Journal of Biochemistry (Blackwell Science, Malden, Mass.).

Sources of biochemical information include, for example, general resources relating to metabolism, resources relating specifically to human metabolism, and resources relating to the biochemistry, physiology and pathology of specific human cell types.

Sources of general information relating to metabolism, which were used to generate the human reaction databases and models described herein, were J. G. Salway, *Metabolism at a Glance*, $2^{nd}$ ed., Blackwell Science, Malden, Mass. (1999) and T. M. Devlin, ed., *Textbook of Biochemistry with Clinical Correlations*, $4^{th}$ ed., John Wiley and Sons, New York, NY (1997). Human metabolism-specific resources included J. R. Bronk, *Human Metabolism: Functional Diversity and Integration*, Addison Wesley Longman, Essex, England (1999).

The literature used in conjunction with the skeletal muscle metabolic models and simulations described herein included R. Maughan et al., *Biochemistry of Exercise and Training*, Oxford University Press, Oxford, England (1997), as well as references on muscle pathology such as S. Carpenter et al., *Pathology of Skeletal Muscle*, $2^{nd}$ ed., Oxford University Press, Oxford, England (2001), and more specific articles on muscle metabolism as may be found in the Journal of Physiology (Cambridge University Press, Cambridge, England).

In the course of developing an in silico model of *Homo sapiens* metabolism, the types of data that can be considered include, for example, biochemical information which is information related to the experimental characterization of a chemical reaction, often directly indicating a protein(s) associated with a reaction and the stoichiometry of the reaction or indirectly demonstrating the existence of a reaction occurring within a cellular extract; genetic information, which is information related to the experimental identification and genetic characterization of a gene(s) shown to code for a particular protein(s) implicated in carrying out a biochemical event; genomic information, which is information related to the identification of an open reading frame and functional assignment, through computational sequence analysis, that is then linked to a protein performing a biochemical event; physiological information, which is information related to overall cellular physiology, fitness characteristics, substrate utilization, and phenotyping results, which provide evidence of the assimilation or dissimilation of a compound used to infer the presence of specific biochemical event (in particular translocations); and modeling information, which is information generated through the course of simulating activity of *Homo sapiens* cells using methods such as those described herein which lead to predictions regarding the status of a reaction such as whether or not the reaction is required to fulfill certain demands placed on a metabolic network. Additional information relevant to multicellular organisms that can be considered includes cell type-specific or condition-specific gene expression information, which can be determined experimentally, such as by gene array analysis or from expressed sequence tag (EST) analysis, or obtained from the biochemical and physiological literature.

The majority of the reactions occurring in *Homo sapiens* reaction networks are catalyzed by enzymes/proteins, which are created through the transcription and translation of the genes found within the chromosome in the cell. The remaining reactions occur either spontaneously or through non-enzymatic processes. Furthermore, a reaction network data structure can contain reactions that add or delete steps to or from a particular reaction pathway. For example, reactions can be added to optimize or improve performance of a *Homo sapiens* model in view of empirically observed activity. Alternatively, reactions can be deleted to remove intermediate steps in a pathway when the intermediate steps are not necessary to model flux through the pathway. For example, if a pathway contains 3 nonbranched steps, the reactions can be combined or added together to give a net reaction, thereby reducing memory required to store the reaction network data structure and the computational resources required for manipulation of the data structure.

The reactions that occur due to the activity of gene-encoded enzymes can be obtained from a genome database which lists genes identified from genome sequencing and subsequent genome annotation. Genome annotation consists of the locations of open reading frames and assignment of function from homology to other known genes or empirically determined activity. Such a genome database can be acquired through public or private databases containing annotated *Homo sapiens* nucleic acid or protein sequences. If desired, a model developer can perform a network reconstruction and establish the model content associations between the genes, proteins, and reactions as described, for example, in Covert et al. *Trends in Biochemical Sciences* 26:179-186 (2001) and Palsson, WO 00/46405.

As reactions are added to a reaction network data structure or metabolic reaction database, those having known or putative associations to the proteins/enzymes which enable/catalyze the reaction and the associated genes that code for these proteins can be identified by annotation. Accordingly, the appropriate associations for all of the reactions to their related proteins or genes or both can be assigned. These associations can be used to capture the non-linear relationship between the genes and proteins as well as between proteins and reactions. In some cases one gene codes for one protein which then perform one reaction. However, often there are multiple genes which are required to create an active enzyme complex and often there are multiple reactions that can be carried out by one protein or multiple proteins that can carry out the same reaction. These associations capture the logic (i.e. AND or OR relationships) within the associations. Annotating a metabolic reaction database with these associations can allow the methods to be used to determine the effects of adding or eliminating a particular reaction not only at the reaction level, but at the genetic or protein level in the context of running a simulation or predicting *Homo sapiens* activity.

A reaction network data structure of the invention can be used to determine the activity of one or more reactions in a plurality of *Homo sapiens* reactions independent of any knowledge or annotation of the identity of the protein that performs the reaction or the gene encoding the protein. A model that is annotated with gene or protein identities can include reactions for which a protein or encoding gene is not assigned. While a large portion of the reactions in a cellular metabolic network are associated with genes in the organism's genome, there are also a substantial number of reactions included in a model for which there are no known genetic associations. Such reactions can be added to a reaction database based upon other information that is not necessarily related to genetics such as biochemical or cell based measurements or theoretical considerations based on observed biochemical or cellular activity. For example, there are many reactions that can either occur spontaneously or are not protein-enabled reactions. Furthermore, the occurrence of a particular reaction in a cell for which no associated proteins or genetics have been currently identified can be indicated during the course of model building by the iterative model building methods of the invention.

The reactions in a reaction network data structure or reaction database can be assigned to subsystems by annotation, if desired. The reactions can be subdivided according to biological criteria, such as according to traditionally identified metabolic pathways (glycolysis, amino acid metabolism and the like) or according to mathematical or computational criteria that facilitate manipulation of a model that incorporates or manipulates the reactions. Methods and criteria for subdividing a reaction database are described in further detail in Schilling et al., *J. Theor. Biol.* 203:249-283 (2000), and in Schuster et al., *Bioinformatics* 18:351-361 (2002). The use of subsystems can be advantageous for a number of analysis methods, such as extreme pathway analysis, and can make the management of model content easier. Although assigning reactions to subsystems can be achieved without affecting the use of the entire model for simulation, assigning reactions to subsystems can allow a user to search for reactions in a particular subsystem which may be useful in performing various types of analyses. Therefore, a reaction network data structure can include any number of desired subsystems including, for example, 2 or more subsystems, 5 or more subsystems, 10 or more subsystems, 25 or more subsystems or 50 or more subsystems.

The reactions in a reaction network data structure or metabolic reaction database can be annotated with a value indicating the confidence with which the reaction is believed to occur in the *Homo sapiens* cell. The level of confidence can be, for example, a function of the amount and form of supporting data that is available. This data can come in various forms including published literature, documented experimental results, or results of computational analyses. Furthermore, the data can provide direct or indirect evidence for the existence of a chemical reaction in a cell based on genetic, biochemical, and/or physiological data.

The invention further provides a computer readable medium, containing (a) a data structure relating a plurality of Homo sapiens reactants to a plurality of Homo sapiens reactions, wherein each of the Homo sapiens reactions includes a reactant identified as a substrate of the reaction, a reactant identified as a product of the reaction and a stoichiometric coefficient relating the substrate and the product, and (b) a constraint set for the plurality of Homo sapiens reactions.

Constraints can be placed on the value of any of the fluxes in the metabolic network using a constraint set. These constraints can be representative of a minimum or maximum allowable flux through a given reaction, possibly resulting from a limited amount of an enzyme present. Additionally, the constraints can determine the direction or reversibility of any of the reactions or transport fluxes in the reaction network data structure. Based on the in vivo environment where Homo sapiens lives the metabolic resources available to the cell for biosynthesis of essential molecules for can be determined. Allowing the corresponding transport fluxes to be active provides the in silico Homo sapiens with inputs and outputs for substrates and by-products produced by the metabolic network.

Returning to the hypothetical reaction network shown in FIG. 1, constraints can-be placed on each reaction in the exemplary format shown in FIG. 2, as follows. The constraints are provided in a format that can be used to constrain the reactions of the stoichiometric matrix shown in FIG. 3. The format for the constraints used for a matrix or in linear programming can be conveniently represented as a linear inequality such as $$b_j \leq v_j \leq a_j; j=1 \ldots n \quad \text{(Eq. 1)}$$

where $v_j$ is the metabolic flux vector, $b_j$ is the minimum flux value and $a_j$ is the maximum flux value. Thus, $a_j$ can take on a finite value representing a maximum allowable flux through a given reaction or $b_j$ can take on a finite value representing minimum allowable flux through a given reaction. Additionally, if one chooses to leave certain reversible reactions or transport fluxes to operate in a forward and reverse manner the flux may remain unconstrained by setting $b_j$ to negative infinity and $a_j$ to positive infinity as shown for reaction $R_2$ in FIG. 2. If reactions proceed only in the forward reaction $b_j$ is set to zero while $a_j$ is set to positive infinity as shown for reactions $R_1$, $R_3$, $R_4$, $R_5$, and $R_6$ in FIG. 2. As an example, to simulate the event of a genetic deletion or non-expression of a particular protein, the flux through all of the corresponding metabolic reactions related to the gene or protein in question are reduced to zero by setting $a_j$ and $b_j$ to be zero. Furthermore, if one wishes to simulate the absence of a particular growth substrate one can simply constrain the corresponding transport fluxes that allow the metabolite to enter the cell to be zero by setting $a_j$ and $b_j$ to be zero. On the other hand if a substrate is only allowed to enter or exit the cell via transport mechanisms, the corresponding fluxes can be properly constrained to reflect this scenario.

The ability of a reaction to be actively occurring is dependent on a large number of additional factors beyond just the availability of substrates. These factors, which can be represented as variable constraints in the models and methods of the invention include, for example, the presence of cofactors necessary to stabilize the protein/enzyme, the presence or absence of enzymatic inhibition and activation factors, the active formation of the protein/enzyme through translation of the corresponding mRNA transcript, the transcription of the associated gene(s) or the presence of chemical signals and/or proteins that assist in controlling these processes that ultimately determine whether a chemical reaction is capable of being carried out within an organism. Of particular importance in the regulation of human cell types is the implementation of paracrine and endocrine signaling pathways to control cellular activities. In these cases a cell secretes signaling molecules that may be carried far afield to act on distant targets (endocrine signaling), or act as local mediators (paracrine signaling). Examples of endocrine signaling molecules include hormones such as insulin, while examples of paracrine signaling molecules include neurotransmitters such as acetylcholine. These molecules induce cellular responses through signaling cascades that affect the activity of biochemical reactions in the cell.

Regulation can be represented in an in silico Homo sapiens model by providing a variable constraint as set forth below.

Thus, the invention provides a computer readable medium or media, including (a) a data structure relating a plurality of Homo sapiens reactants to a plurality of Homo sapiens reactions, wherein each of the reactions includes a reactant identified as a substrate of the reaction, a reactant identified as a product of the reaction and a stoichiometric coefficient relating the substrate and the product, and wherein at least one of the reactions is a regulated reaction; and (b) a constraint set for the plurality of reactions, wherein the constraint set includes a variable constraint for the regulated reaction.

As used herein, the term "regulated," when used in reference to a reaction in a data structure, is intended to mean a reaction that experiences an altered flux due to a change in the value of a constraint or a reaction that has a variable constraint.

As used herein, the term "regulatory reaction" is intended to mean a chemical conversion or interaction that alters the activity of a protein, macromolecule or enzyme. A chemical conversion or interaction can directly alter the activity of a protein, macromolecule or enzyme such as occurs when the protein, macromolecule or enzyme is post-translationally modified or can indirectly alter the activity of a protein, macromolecule or enzyme such as occurs when a chemical conversion or binding event leads to altered expression of the protein, macromolecule or enzyme. Thus, transcriptional or translational regulatory pathways can indirectly alter a protein, macromolecule or enzyme or an associated reaction. Similarly, indirect regulatory reactions can include reactions that occur due to downstream components or participants in a regulatory reaction network. When used in reference to a data structure or in silico Homo sapiens model, the term is intended to mean a first reaction that is related to a second reaction by a function that alters the flux through the second reaction by changing the value of a constraint on the second reaction.

As used herein, the term "regulatory data structure" is intended to mean a representation of an event, reaction or network of reactions that activate or inhibit a reaction, the representation being in a format that can be manipulated or analyzed. An event that activates a reaction can be an event that initiates the reaction or an event that increases the rate or level of activity for the reaction. An event that inhibits a reaction can be an event that stops the reaction or an event that decreases the rate or level of activity for the reaction. Reactions that can be represented in a regulatory data structure include, for example, reactions that control expression of a macromolecule that in turn, performs a reaction such as transcription and translation reactions, reactions that lead to post translational modification of a protein or enzyme such as phophorylation, dephosphorylation, prenylation, methylation, oxidation or covalent modification, reactions that process a protein or enzyme such as removal of a pre- or pro-sequence, reactions that degrade a protein or enzyme or reactions that lead to assembly of a protein or enzyme.

As used herein, the term "regulatory event" is intended to mean a modifier of the flux through a reaction that is independent of the amount of reactants available to the reaction. A modification included in the term can be a change in the presence, absence, or amount of an enzyme that performs a reaction. A modifier included in the term can be a regulatory reaction such as a signal transduction reaction or an environmental condition such as a change in pH, temperature, redox potential or time. It will be understood that when used in reference to an in silico *Homo sapiens* model or data structure a regulatory event is intended to be a representation of a modifier of the flux through a *Homo sapiens* reaction that is independent of the amount of reactants available to the reaction.

Figure 4:
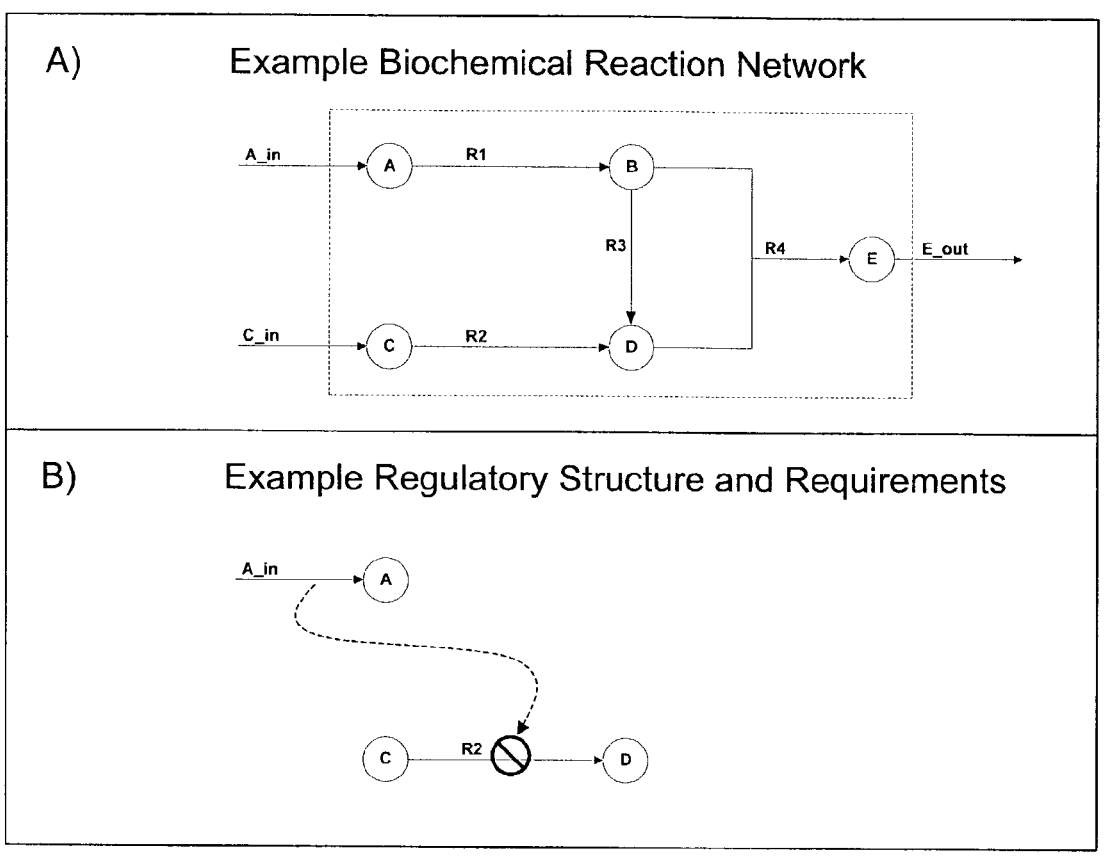
FIG. 4 shows, in Panel A, an exemplary biochemical reaction network and in Panel B, an exemplary regulatory control structure for the reaction network in panel A.

The effects of regulation on one or more reactions that occur in *Homo sapiens* can be predicted using an in silica *Homo sapiens* model of the invention. Regulation can be taken into consideration in the context of a particular condition being examined by providing a variable constraint for the reaction in an in silico *Homo sapiens* model. Such constraints constitute condition-dependent constraints. A data structure can represent regulatory reactions as Boolean logic statements (Reg-reaction). The variable takes on a value of 1 when the reaction is available for use in the reaction network and will take on a value of 0 if the reaction is restrained due to some regulatory feature. A series of Boolean statements can then be introduced to mathematically represent the regulatory network as described for example in Covert et al. *J. Theor. Biol.* 213:73-88 (2001). For example, in the case of a transport reaction (A_in) that imports metabolite A, where metabolite A inhibits reaction R2 as shown in FIG. 4, a Boolean rule can state that:

$$\text{Reg-}R2 = \text{IF NOT}(A\_in) \tag{Eq. 2}$$

This statement indicates that reaction R2 can occur if reaction A_in is not occurring (i.e. if metabolite A is not present). Similarly, it is possible to assign the regulation to a variable A which would indicate an amount of A above or below a threshold that leads to the inhibition of reaction R2. Any function that provides values for variables corresponding to each of the reactions in the biochemical reaction network can be used to represent a regulatory reaction or set of regulatory reactions in a regulatory data structure. Such functions can include, for example, fuzzy logic, heuristic rule-based descriptions, differential equations or kinetic equations detailing system dynamics.

A reaction constraint placed on a reaction can be incorporated into an in silico *Homo sapiens* model using the following general equation:

$$(\text{Reg-Reaction}) * b_j \leq v_j \leq a_j * (\text{Reg-Reaction}) \tag{Eq. 3}$$

j=1 ... n

For the example of reaction R2 this equation is written as follows:

$$(0) * \text{Reg-}R2 \leq R2 \leq (\infty) \cdot \text{Reg-}R2 \tag{Eq. 4}$$

Thus, during the course of a simulation, depending upon the presence or absence of metabolite A in the interior of the cell where reaction R2 occurs, the value for the upper boundary of flux for reaction R2 will change from 0 to infinity, respectively.

With the effects of a regulatory event or network taken into consideration by a constraint function and the condition-dependent constraints set to an initial relevant value, the behavior of the *Homo sapiens* reaction network can be simulated for the conditions considered as set forth below.

Although regulation has been exemplified above for the case where a variable constraint is dependent upon the outcome of a reaction in the data structure, a plurality of variable constraints can be included in an in silico *Homo sapiens* model to represent regulation of a plurality of reactions. Furthermore, in the exemplary case set forth above, the regulatory structure includes a general control stating that a reaction is inhibited by a particular environmental condition. Using a general control of this type, it is possible to incorporate molecular mechanisms and additional detail into the regulatory structure that is responsible for determining the active nature of a particular chemical reaction within an organism.

Regulation can also be simulated by a model of the invention and used to predict a *Homo sapiens* physiological function without knowledge of the precise molecular mechanisms involved in the reaction network being modeled. Thus, the model can be used to predict, in silico, overall regulatory events or causal relationships that are not apparent from in vivo observation of any one reaction in a network or whose in vivo effects on a particular reaction are not known. Such overall regulatory effects can include those that result from overall environmental conditions such as changes in pH, temperature, redox potential, or the passage of time.

The in silico *Homo sapiens* model and methods described herein can be implemented on any conventional host computer system, such as those based on Intel.RTM. microprocessors and running Microsoft Windows operating systems. Other systems, such as those using the UNIX or LINUX operating system and based on IBM.RTM., DEC.RTM. or Motorola.RTM. microprocessors are also contemplated. The systems and methods described herein can also be implemented to run on client-server systems and wide-area networks, such as the Internet.

Software to implement a method or model of the invention can be written in any well-known computer language, such as Java, C, C++, Visual Basic, FORTRAN or COBOL and compiled using any well-known compatible compiler. The software of the invention normally runs from instructions stored in a memory on a host computer system. A memory or computer readable medium can be a hard disk, floppy disc, compact disc, magneto-optical disc, Random Access Memory, Read Only Memory or Flash Memory. The memory or computer readable medium used in the invention can be contained within a single computer or distributed in a network. A network can be any of a number of conventional network systems known in the art such as a local area network (LAN) or a wide area network (WAN). Client-server environments, database servers and networks that can be used in the invention are well known in the art. For example, the database server can run on an operating system such as UNIX, running a relational database management system, a World Wide Web application and a World Wide Web server. Other types of memories and computer readable media are also contemplated to function within the scope of the invention.

A database or data structure of the invention can be represented in a markup language format including, for example, Standard Generalized Markup Language (SGML), Hypertext markup language (HTML) or Extensible Markup language (XML). Markup languages can be used to tag the information stored in a database or data structure of the invention, thereby providing convenient annotation and transfer of data between databases and data structures. In particular, an XML format can be useful for structuring the data representation of reactions, reactants and their annotations; for exchanging database contents, for example, over a network or internet; for updating individual elements using the document object model; or for providing differential access to multiple users for different information content of a data base or data structure of the invention. XML programming methods and editors for writing XML code are known in the art as described, for example, in Ray, "Learning XML" O'Reilly and Associates, Sebastopol, Calif. (2001).

A set of constraints can be applied to a reaction network data structure to simulate the flux of mass through the reaction network under a particular set of environmental conditions specified by a constraints set. Because the time constants characterizing metabolic transients and/or metabolic reactions are typically very rapid, on the order of milli-seconds to seconds, compared to the time constants of cell growth on the order of hours to days, the transient mass balances can be simplified to only consider the steady state behavior. Referring now to an example where the reaction network data structure is a stoichiometric matrix, the steady state mass balances can be applied using the following system of linear equations $$S \cdot v = 0 \quad \text{(Eq. 5)}$$

where S is the stoichiometric matrix as defined above and v is the flux vector. This equation defines the mass, energy, and redox potential constraints placed on the metabolic network as a result of stoichiometry. Together Equations 1 and 5 representing the reaction constraints and mass balances, respectively, effectively define the capabilities and constraints of the metabolic genotype and the organism's metabolic potential. All vectors, v, that satisfy Equation 5 are said to occur in the mathematical nullspace of S. Thus, the null space defines steady-state metabolic flux distributions that do not violate the mass, energy, or redox balance constraints. Typically, the number of fluxes is greater than the number of mass balance constraints, thus a plurality of flux distributions satisfy the mass balance constraints and occupy the null space. The null space, which defines the feasible set of metabolic flux distributions, is further reduced in size by applying the reaction constraints set forth in Equation 1 leading to a defined solution space. A point in this space represents a flux distribution and hence a metabolic phenotype for the network. An optimal solution within the set of all solutions can be determined using mathematical optimization methods when provided with a stated objective and a constraint set. The calculation of any solution constitutes a simulation of the model.

Objectives for activity of a human cell can be chosen. While the overall objective of a multi-cellular organism may be growth or reproduction, individual human cell types generally have much more complex objectives, even to the seemingly extreme objective of apoptosis (programmed cell death), which may benefit the organism but certainly not the individual cell. For example, certain cell types may have the objective of maximizing energy production, while others have the objective of maximizing the production of a particular hormone, extracellular matrix component, or a mechanical property such as contractile force. In cases where cell reproduction is slow, such as human skeletal muscle, growth and its effects need not be taken into account. In other cases, biomass composition and growth rate could be incorporated into a "maintenance" type of flux, where rather than optimizing for growth, production of precursors is set at a level consistent with experimental knowledge and a different objective is optimized.

Certain cell types, including cancer cells, can be viewed as having an objective of maximizing cell growth. Growth can be defined in terms of biosynthetic requirements based on literature values of biomass composition or experimentally determined values such as those obtained as described above. Thus, biomass generation can be defined as an exchange reaction that removes intermediate metabolites in the appropriate ratios and represented as an objective function. In addition to draining intermediate metabolites this reaction flux can be formed to utilize energy molecules such as ATP, NADH and NADPH so as to incorporate any maintenance requirement that must be met. This new reaction flux then becomes another constraint/balance equation that the system must satisfy as the objective function. Using the stoichiometric matrix of FIG. 3 as an example, adding such a constraint is analogous to adding the additional column $V_{growth}$ to the stoichiometric matrix to represent fluxes to describe the production demands placed on the metabolic system. Setting this new flux as the objective function and asking the system to maximize the value of this flux for a given set of constraints on all the other fluxes is then a method to simulate the growth of the organism.

Continuing with the example of the stoichiometric matrix applying a constraint set to a reaction network data structure can be illustrated as follows. The solution to equation 5 can be formulated as an optimization problem, in which the flux distribution that minimizes a particular objective is found. Mathematically, this optimization problem can be stated as:

$$\text{Minimize } Z \quad \text{(Eq. 6)}$$

$$\text{where } z = \Sigma c_i \cdot v_i \quad \text{(Eq. 7)}$$

where Z is the objective which is represented as a linear combination of metabolic fluxes $v_i$ using the weights $c_i$ in this linear combination. The optimization problem can also be stated as the equivalent maximization problem; i.e. by changing the sign on Z. Any commands for solving the optimazation problem can be used including, for example, linear programming commands.

A computer system of the invention can further include a user interface capable of receiving a representation of one or more reactions. A user interface of the invention can also be capable of sending at least one command for modifying the data structure, the constraint set or the commands for applying the constraint set to the data representation, or a combination thereof. The interface can be a graphic user interface having graphical means for making selections such as menus or dialog boxes. The interface can be arranged with layered screens accessible by making selections from a main screen. The user interface can provide access to other databases useful in the invention such as a metabolic reaction database or links to other databases having information relevant to the reactions or reactants in the reaction network data structure or to *Homo sapiens* physiology. Also, the user interface can display a graphical representation of a reaction network or the results of a simulation using a model of the invention.

Once an initial reaction network data structure and set of constraints has been created, this model can be tested by preliminary simulation. During preliminary simulation, gaps in the network or "dead-ends" in which a metabolite can be produced but not consumed or where a metabolite can be consumed but not produced can be identified. Based on the results of preliminary simulations areas of the metabolic reconstruction that require an additional reaction can be identified. The determination of these gaps can be readily calculated through appropriate queries of the reaction network data structure and need not require the use of simulation strategies, however, simulation would be an alternative approach to locating such gaps.

In the preliminary simulation testing and model content refinement stage the existing model is subjected to a series of functional tests to determine if it can perform basic requirements such as the ability to produce the required biomass constituents and generate predictions concerning the basic physiological characteristics of the particular cell type being modeled. The more preliminary testing that is conducted the higher the quality of the model that will be generated. Typically, the majority of the simulations used in this stage of development will be single optimizations. A single optimization can be used to calculate a single flux distribution demonstrating how metabolic resources are routed determined from the solution to one optimization problem. An optimization problem can be solved using linear programming as demonstrated in the Examples below. The result can be viewed as a display of a flux distribution on a reaction map. Temporary reactions can be added to the network to determine if they should be included into the model based on modeling/simulation requirements.

Once a model of the invention is sufficiently complete with respect to the content of the reaction network data structure according to the criteria set forth above, the model can be used to simulate activity of one or more reactions in a reaction network. The results of a simulation can be displayed in a variety of formats including, for example, a table, graph, reaction network, flux distribution map or a phenotypic phase plane graph.

Thus, the invention provides a method for predicting a *Homo sapiens* physiological function. The method includes the steps of (a) providing a data structure relating a plurality of *Homo sapiens* reactants to a plurality of *Homo sapiens* reactions, wherein each of the *Homo sapiens* reactions includes a reactant identified as a substrate of the reaction, a reactant identified as a product of the reaction and a stoichiometric coefficient relating said substrate and said product; (b) providing a constraint set for the plurality of *Homo sapiens* reactions; (c) providing an objective function, and (d) determining at least one flux distribution that minimizes or maximizes the objective function when the constraint set is applied to the data structure, thereby predicting a *Homo sapiens* physiological function.

A method for predicting a *Homo sapiens* physiological function can include the steps of (a) providing a data structure relating a plurality of *Homo sapiens* reactants to a plurality of *Homo sapiens* reactions, wherein each of the *Homo sapiens* reactions includes a reactant identified as a substrate of the reaction, a reactant identified as a product of the reaction and a stoichiometric coefficient relating the substrate and the product, and wherein at least one of the reactions is a regulated reaction; (b) providing a constraint set for the plurality of reactions, wherein the constraint set includes a variable constraint for the regulated reaction; (c) providing a condition-dependent value to the variable constraint; (d) providing an objective function, and (e) determining at least one flux distribution that minimizes or maximizes the objective function when the constraint set is applied to the data structure, thereby predicting a *Homo sapiens* physiological function.

As used herein, the term "physiological function," when used in reference to *Homo sapiens*, is intended to mean an activity of a *Homo sapiens* cell as a whole. An activity included in the term can be the magnitude or rate of a change from an initial state of a *Homo sapiens* cell to a final state of the *Homo sapiens* cell. An activity included in the term can be, for example, growth, energy production, redox equivalent production, biomass production, development, or consumption of carbon nitrogen, sulfur, phosphate, hydrogen or oxygen. An activity can also be an output of a particular reaction that is determined or predicted in the context of substantially all of the reactions that affect the particular reaction in a *Homo sapiens* cell or substantially all of the reactions that occur in a *Homo sapiens* cell (e.g. muscle contraction). Examples of a particular reaction included in the term are production of biomass precursors, production of a protein, production of an amino acid, production of a purine, production of a pyrimidine, production of a lipid, production of a fatty acid, production of a cofactor or transport of a metabolite. A physiological function can include an emergent property which emerges from the whole but not from the sum of parts where the parts are observed in isolation (see for example, Palsson, *Nat. Biotech* 18:1147-1150 (2000)).

A physiological function of *Homo sapiens* reactions can be determined using phase plane analysis of flux distributions. Phase planes are representations of the feasible set which can be presented in two or three dimensions. As an example, two parameters that describe the growth conditions such as substrate and oxygen uptake rates can be defined as two axes of a two-dimensional space. The optimal flux distribution can be calculated from a reaction network data structure and a set of constraints as set forth above for all points in this plane by repeatedly solving the linear programming problem while adjusting the exchange fluxes defining the two-dimensional space. A finite number of qualitatively different metabolic pathway utilization patterns can be identified in such a plane, and lines can be drawn to demarcate these regions. The demarcations defining the regions can be determined using shadow prices of linear optimization as described, for example in Chvatal, *Linear Programming* New York, W. H. Freeman and Co. (1983). The regions are referred to as regions of constant shadow price structure. The shadow prices define the intrinsic value of each reactant toward the objective function as a number that is either negative, zero, or positive and are graphed according to the uptake rates represented by the x and y axes. When the shadow prices become zero as the value of the uptake rates are changed there is a qualitative shift in the optimal reaction network.

One demarcation line in the phenotype phase plane is defined as the line of optimality (LO). This line represents the optimal relation between respective metabolic fluxes. The LO can be identified by varying the x-axis flux and calculating the optimal y-axis flux with the objective function defined as the growth flux From the phenotype phase plane analysis the conditions under which a desired activity is optimal can be determined. The maximal uptake rates lead to the definition of a finite area of the plot that is the predicted outcome of a reaction network within the environmental conditions represented by the constraint set. Similar analyses can be performed in multiple dimensions where each dimension on the plot corresponds to a different uptake rate. These and other methods for using phase plane analysis, such as those described in Edwards et al., *Biotech Bioeng.* 77:27-36(2002), can be used to analyze the results of a simulation using an in silico *Homo sapiens* model of the invention.

A physiological function of *Homo sapiens* can also be determined using a reaction map to display a flux distribution. A reaction map of *Homo sapiens* can be used to view reaction networks at a variety of levels. In the case of a cellular metabolic reaction network a reaction map can contain the entire reaction complement representing a global perspective. Alternatively, a reaction map can focus on a particular region of metabolism such as a region corresponding to a reaction subsystem described above or even on an individual pathway or reaction.

Thus, the invention provides an apparatus that produces a representation of a *Homo sapiens* physiological function, wherein the representation is produced by a process including the steps of: (a) providing a data structure relating a plurality of *Homo sapiens* reactants to a plurality of *Homo sapiens* reactions, wherein each of the *Homo sapiens* reactions includes a reactant identified as a substrate of the reaction, a reactant identified as a product of the reaction and a stoichiometric coefficient relating said substrate and said product; (b) providing a constraint set for the plurality of *Homo sapiens* reactions; (c) providing an objective function; (d) determining at least one flux distribution that minimizes or maximizes the objective function when the constraint set is applied to the data structure, thereby predicting a *Homo sapiens* physiological function, and (e) producing a representation of the activity of the one or more *Homo sapiens* reactions.

The methods of the invention can be used to determine the activity of a plurality of *Homo sapiens* reactions including, for example, biosynthesis of an amino acid, degradation of an amino acid, biosynthesis of a purine, biosynthesis of a pyrimidine, biosynthesis of a lipid, metabolism of a fatty acid, biosynthesis of a cofactor, transport of a metabolite and metabolism of an alternative carbon source. In addition, the methods can be used to determine the activity of one or more of the reactions described above or listed in Table 1.

The methods of the invention can be used to determine a phenotype of a *Homo sapiens* mutant. The activity of one or more *Homo sapiens* reactions can be determined using the methods described above, wherein the reaction network data structure lacks one or more gene-associated reactions that occur in *Homo sapiens*. Alternatively, the methods can be used to determine the activity of one or more *Homo sapiens* reactions when a reaction that does not naturally occur in *Homo sapiens* is added to the reaction network data structure. Deletion of a gene can also be represented in a model of the invention by constraining the flux through the reaction to zero, thereby allowing the reaction to remain within the data structure. Thus, simulations can be made to predict the effects of adding or removing genes to or from *Homo sapiens*. The methods can be particularly useful for determining the effects of adding or deleting a gene that encodes for a gene product that performs a reaction in a peripheral metabolic pathway.

A drug target or target for any other agent that affects *Homo sapiens* function can be predicted using the methods of the invention. Such predictions can be made by removing a reaction to simulate total inhibition or prevention by a drug or agent. Alternatively, partial inhibition or reduction in the activity a particular reaction can be predicted by performing the methods with altered constraints. For example, reduced activity can be introduced into a model of the invention by altering the $a_j$ or $b_j$ values for the metabolic flux vector of a target reaction to reflect a finite maximum or minimum flux value corresponding to the level of inhibition. Similarly, the effects of activating a reaction, by initiating or increasing the activity of the reaction, can be predicted by performing the methods with a reaction network data structure lacking a particular reaction or by altering the $a_j$ or $b_j$ values for the metabolic flux vector of a target reaction to reflect a maximum or minimum flux value corresponding to the level of activation. The methods can be particularly useful for identifying a target in a peripheral metabolic pathway.

Once a reaction has been identified for which activation or inhibition produces a desired effect on *Homo sapiens* function, an enzyme or macromolecule that performs the reaction in *Homo sapiens* or a gene that expresses the enzyme or macromolecule can be identified as a target for a drug or other agent. A candidate compound for a target identified by the methods of the invention can be isolated or synthesized using known methods. Such methods for isolating or synthesizing compounds can include, for example, rational design based on known properties of the target (see, for example, DeCamp et al., *Protein Engineering Principles and Practice*, Ed. Cleland and Craik, Wiley-Liss, New York, pp. 467-506 (1996)), screening the target against combinatorial libraries of compounds (see for example, Houghten et al., *Nature*, 354, 84-86 (1991); Dooley et al., *Science*, 266, 2019-2022 (1994), which describe an iterative approach, or R. Houghten et al. PCT/US91/08694 and U.S. Pat. No. 5,556,762 which describe the positional-scanning approach), or a combination of both to obtain focused libraries. Those skilled in the art will know or will be able to routinely determine assay conditions to be used in a screen based on properties of the target or activity assays known in the art.

A candidate drug or agent, whether identified by the methods described above or by other methods known in the art, can be validated using an in silico *Homo sapiens* model or method of the invention. The effect of a candidate drug or agent on *Homo sapiens* physiological function can be predicted based on the activity for a target in the presence of the candidate drug or agent measured in vitro or in vivo. This activity can be represented in an in silico *Homo sapiens* model by adding a reaction to the model, removing a reaction from the model or adjusting a constraint for a reaction in the model to reflect the measured effect of the candidate drug or agent on the activity of the reaction. By running a simulation under these conditions the holistic effect of the candidate drug or agent on *Homo sapiens* physiological function can be predicted.

The methods of the invention can be used to determine the effects of one or more environmental components or conditions on an activity of a *Homo sapiens* cell. As set forth above an exchange reaction can be added to a reaction network data structure corresponding to uptake of an environmental component, release of a component to the environment, or other environmental demand. The effect of the environmental component or condition can be further investigated by running simulations with adjusted $a_j$ or $b_j$ values for the metabolic flux vector of the exchange reaction target reaction to reflect a finite maximum or minimum flux value corresponding to the effect of the environmental component or condition. The environmental component can be, for example an alternative carbon source or a metabolite that when added to the environment of a *Homo sapiens* cell can be taken up and metabolized. The environmental component can also be a combination of components present for example in a minimal medium composition. Thus, the methods can be used to determine an optimal or minimal medium composition that is capable of supporting a particular activity of *Homo sapiens*.

The invention further provides a method for determining a set of environmental components to achieve a desired activity for *Homo sapiens*. The method includes the steps of (a) providing a data structure relating a plurality of *Homo sapiens* reactants to a plurality of *Homo sapiens* reactions, wherein each of the *Homo sapiens* reactions includes a reactant identified as a substrate of the reaction, a reactant identified as a product of the reaction and a stoichiometric coefficient relating the substrate and the product; (b) providing a constraint set for the plurality of *Homo sapiens* reactions; (c) applying the constraint set to the data representation, thereby determining the activity of one or more *Homo sapiens* reactions (d) determining the activity of one or more *Homo sapiens* reactions according to steps (a) through (c), wherein the constraint set includes an upper or lower bound on the amount of an environmental component and (e) repeating steps (a) through (c) with a changed constraint set, wherein the activity determined in step (e) is improved compared to the activity determined in step (d).

The following examples are intended to illustrate but not limit the present invention.

EXAMPLE I

This example shows the construction of a universal *Homo sapiens* metabolic reaction database, a *Homo sapiens* core metabolic reaction database and a *Homo sapiens* muscle cell metabolic reaction database. This example also shows the iterative model building process used to generate a *Homo sapiens* core metabolic model and a *Homo sapiens* muscle cell metabolic model.

A universal *Homo sapiens* reaction database was prepared from the genome databases and biochemical literature. The reaction database shown in Table 1 contains the following information:

Locus ID—the locus number of the gene found in the LocusLink website.

Gene Ab.—various abbreviations which are used for the gene.

Reaction Stoichiometry—includes all metabolites and direction of the reaction, as well as reversibility.

E.C.—The Enzyme Commission number.

Additional information included in the universal reaction database, although not shown in Table 1, included the chapter of Salway, supra (1999), where relevant reactions were found; the cellular location, if the reaction primarily occurs in a given compartment; the SWISS PROT identifier, which can be used to locate the gene record in SWISS PROT; the full name of the gene at the given locus; the chromosomal location of the gene; the Mendelian Inheritance in Man (MIM) data associated with the gene; and the tissue type, if the gene is primarily expressed in a certain tissue. Overall, 1130 metabolic enzyme- or transporter-encoding genes were included in the universal reaction database.

Fifty-nine reactions in the universal reaction database were identified and included based on biological data as found in Salway supra (1999), currently without genome annotation. Ten additional reactions, not described in the biochemical literature or genome annotation, were subsequently included in the reaction database following preliminary simulation testing and model content refinement. These 69 reactions are shown at the end of Table 1.

From the universal *Homo sapiens* reaction database shown in Table 1, a core metabolic reaction database was established, which included core metabolic reactions as well as some amino acid and fatty acid metabolic reactions, as described in Chapters 1, 3, 4, 7, 9, 10, 13, 17, 18 and 44 of J. G. Salway, *Metabolism at a Glance*, $2^{nd}$ ed., Blackwell Science, Malden, Mass. (1999). The core metabolic reaction database included 211 unique reactions, accounting for 737 genes in the *Homo sapiens* genome. The core metabolic reaction database was used, although not in its entirety, to create the core metabolic model described in Example II.

To allow for the modeling of muscle cells, the core reaction database was expanded to include 446 unique reactions, accounting for 889 genes in the *Homo sapiens* genome. This skeletal muscle metabolic reaction database was used to create the skeletal muscle metabolic model described in Example II.

Once the core and muscle cell metabolic reaction databases were compiled, the reactions were represented as a metabolic network data structure, or "stoichiometric input file." For example, the core metabolic network data structure shown in Table 2 contains 33 reversible reactions, 31 non-reversible reactions, 97 matrix columns and 52 unique enzymes. Each reaction in Table 2 is represented so as to indicate the substrate or substrates (a negative number) and the product or products (a positive number); the stoichiometry; the name of each reaction (the term following the zero); and whether the reaction is reversible (an R following the reaction name). A metabolite that appears in the mitochondria is indicated by an "m," and a metabolite that appears in the extracellular space is indicated by an "ex."

To perform a preliminary simulation or to simulate a physiological condition, a set of inputs and outputs has to be defined and the network objective function specified. To calculate the maximum ATP production of the *Homo sapiens* core metabolic network using glucose as a carbon source, a non-zero uptake value for glucose was assigned and ATP production was maximized as the objective function, using the representation shown in Table 2. The network's performance was examined by optimizing for the given objective function and the set of constraints defined in the input file, using flux balance analysis methods. The model was refined in an iterative manner by examining the results of the simulation and implementing the appropriate changes.

Using this iterative procedure, two metabolic reaction networks were generated, representing human core metabolism and human skeletal muscle cell metabolism.

EXAMPLE II

This example shows how human metabolism can be accurately simulated using a *Homo sapiens* core metabolic model.

The human core metabolic reaction database shown in Table 3 was used in simulations of human core metabolism. This reaction database contains a total of 65 reactions, covering the classic biochemical pathways of glycolysis, the pentose phosphate pathway, the tricitric acid cycle, oxidative phosphorylation, glycogen storage, the malate/aspartate shuttle, the glycerol phosphate shuttle, and plasma and mitochondrial membrane transporters. The reaction network was divided into three compartments: the cytosol, mitochondria, and the extracellular space. The total number of metabolites in the network is 50, of which 35 also appear in the mitochondria. This core metabolic network accounts for 250 human genes.

To perform simulations using the core metabolic network, network properties such as the P/O ratio were specified using Salway, supra (1999) as a reference. Oxidation of NADH through the Electron Transport System (ETS) was set to generate 2.5 ATP molecules (i.e. a P/O ratio of 2.5 for NADH), and that of $FADH_2$ was set to 1.5 ATP molecules (i.e. a P/O ratio of 1.5 for $FADH_2$).

Using the core metabolic network, aerobic and anaerobic metabolisms were simulated in silico. Secretion-of metabolic by-products was in agreement with the known physiological parameters. Maximum yield of all 12 precursor-metabolites (glucose-6-phosphate, fructose-6-phosphate, ribose-5-phosphate, erythrose-4-phosphate, triose phosphate, 3-phosphoglycerate, phosphoenolpyruvate, pyruvate, acetyl CoA, α-ketoglutarate, succinyl CoA, and oxaloacetate) was examined and none found to exceed the values of its theoretical yield.

Maximum ATP yield was also examined in the cytosol and mitochondria. Salway, supra (1999) reports that in the absence of membrane proton-coupled transport systems, the energy yield is 38 ATP molecules per molecule of glucose and otherwise 31 ATP molecules per molecule of glucose. The core metabolic model demonstrated the same values as described by Salway supra (1999). Energy yield in the mitochondria was determined to be 38 molecules of ATP per glucose molecule. This is equivalent to production of energy in the absence of proton-couple transporters across mitochondrial membrane since all the protons were utilized only in oxidative phosphorylation. In the cytosol, energy yield was calculated to be 30.5 molecules of ATP per glucose molecule. This value reflects the cost of metabolite exchange across the mitochondrial membrane as described by Salway, supra (1999).

EXAMPLE III

This example shows how human muscle cell metabolism can be accurately simulated under various physiological and pathological conditions using a *Homo sapiens* muscle cell metabolic model.

As described in Example I, the core metabolic model was extended to also include all the major reactions occurring in the skeletal muscle cell, adding new functions to the classical metabolic pathways found in the core model, such as fatty acid synthesis and β-oxidation, triacylglycerol and phospholipid formation, and amino acid metabolism. Simulations were performed using the muscle cell reaction database shown in Table 4. The biochemical reactions were again compartmentalized into cytosolic and mitochondrial compartments.

To simulate physiological behavior of human skeletal muscle cells, an objective function had to be defined. Growth of muscle cells occurs in time scales of several hours to days. The time scale of interest in the simulation, however, was in the order of several to tens of minutes, reflecting the time period of metabolic changes during exercise. Thus, contraction (defined as, and related to energy production) was chosen to be the objective function, and no additional constraints were imposed to represent growth demands in the cell.

To study and test the behavior of the network, twelve physiological cases (Table 5) and five disease cases (Table 6) were examined. The input and output of metabolites were specified as indicated in Table 5, and maximum energy production and metabolite secretions were calculated and taken into account.

TABLE 5

| Metabolite Exchange | 1 | 2 | 3 | 4 | 5 | 6 | 7 | 8 | 9 | 10 | 11 | 12 |
|---|---|---|---|---|---|---|---|---|---|---|---|---|
| Glucose | I | I | — | — | I | I | — | — | — | — | — | — |
| O2 | I | — | I | — | I | — | I | — | I | — | I | — |
| Palmitate | I | I | — | — | — | — | — | — | I | I | — | — |
| Glycogen | I | I | I | I | — | — | — | — | — | — | — | — |
| Phosphocreatine | I | I | — | — | — | — | — | — | — | — | I | I |
| Triacylglycerol | I | I | — | — | — | I | I | — | — | — | — | — |
| Isoleucine | I | I | — | — | — | — | — | — | — | — | — | — |
| Valine | I | I | — | — | — | — | — | — | — | — | — | — |
| Hydroxybutyrate | — | — | — | — | — | — | — | — | — | — | — | — |
| Pyruvate | O | O | O | O | O | O | O | O | O | O | O | O |
| Lactate | O | O | O | O | O | O | O | O | O | O | O | O |

TABLE 5-continued

| Metabolite Exchange | 1 | 2 | 3 | 4 | 5 | 6 | 7 | 8 | 9 | 10 | 11 | 12 |
|---|---|---|---|---|---|---|---|---|---|---|---|---|
| Albumin | O | O | O | O | O | O | O | O | O | O | O | O |

TABLE 6

| Disease | Enzyme Deficiency | Reaction Constrained |
|---|---|---|
| McArdle's disease | phosphorylase | GBE1 |
| Tarui's disease | phosphofructokianse | PFKL |
| Phosphoglycerate kinase deficiency | phosphoglycerate kinase | PGK1R |
| Phosphoglycerate mutase deficiency | phosphoglycerate mutase | PGAM3R |
| Lactate dehydrogenase deficiency | Lactate dehyrogenase | LDHAR |

The skeletal muscle model was tested for utilization of various carbon sources available during various stages of exercise and food starvation (Table 5). The by-product secretion of the network in an aerobic to anaerobic shift was qualitatively compared to physiological outcome of exercise and found to exhibit the same general features such as secretion of fermentative by-products and lowered energy yield.

The network behavior was also examined for five disease cases (Table 6). The test cases were chosen based on their physiological relevance to the model's predictive capabilities. In brief, McArdle's disease is marked by the impairment of glycogen breakdown. Tarui's disease is characterized by a deficiency in phosphofructokinase. The remaining diseases examined are marked by a deficiency of metabolic enzymes phosphoglycerate kinase, phosphoglycerate mutase, and lactate dehydrogenase. In each case, the changes in flux and by-product secretion of metabolites were examined for an aerobic to anaerobic metabolic shift with glycogen and phosphocreatine as the sole carbon sources to the network and pyruvate, lactate, and albumin as the only metabolic by-products allowed to leave the system. To simulate the disease cases, the corresponding deficient enzyme was constrained to zero. In all cases, a severe reduction in energy production was demonstrated during exercise, representing the state of the disease as seen in clinical cases.

Throughout this application various publications have been referenced. The disclosures of these publications in their entireties are hereby incorporated by reference in this application in order to more fully describe the state of the art to which this invention pertains.

Although the invention has been described with reference to the examples provided above, it should be understood that various modifications can be made without departing from the spirit of the invention. Accordingly, the invention is limited only by the claims.

TABLE 1

| Locus ID | Gene Ab. | Reaction Stoichiometry | E.C. |
|---|---|---|---|

1. Carbohydrate Metabolism
1.1 Glycolysis/Gluconeogenesis [PATH: hsa00010]

| | | | |
|---|---|---|---|
| 3098 | HK1 | GLC + ATP -> G6P + ADP | 2.7.1.1 |
| 3099 | HK2 | GLC + ATP -> G6P + ADP | 2.7.1.1 |
| 3101 | HK3 | GLC + ATP -> G6P + ADP | 2.7.1.1 |
| 2645 | GCK, HK4, MODY2, NIDDM | GLC + ATP -> G6P + ADP | 2.7.1.2 |
| 2538 | G6PC, G6PT | G6P + H2O -> GLC + PI | 3.1.3.9 |

TABLE 1-continued

| Locus ID | Gene Ab. | Reaction Stoichiometry | E.C. |
|---|---|---|---|
| 2821 | GPI | G6P <-> F6P | 5.3.1.9 |
| 5211 | PFKL | F6P + ATP -> FDP + ADP | 2.7.1.11 |
| 5213 | PFKM | F6P + ATP -> FDP + ADP | 2.7.1.11 |
| 5214 | PFKP, PFK-C | F6P + ATP -> FDP + ADP | 2.7.1.11 |
| 5215 | PFKX | F6P + ATP -> FDP + ADP | 2.7.1.11 |
| 2203 | FBP1, FBP | FDP + H2O -> F6P + PI | 3.1.3.11 |
| 8789 | FBP2 | FDP + H2O -> F6P + PI | 3.1.3.11 |
| 226 | ALDOA | FDP <-> T3P2 + T3P1 | 4.1.2.13 |
| 229 | ALDOB | FDP <-> T3P2 + T3P1 | 4.1.2.13 |
| 230 | ALDOC | FDP <-> T3P2 + T3P1 | 4.1.2.13 |
| 7167 | TPI1 | T3P2 <-> T3P1 | 5.3.1.1 |
| 2597 | GAPD, GAPDH | T3P1 + PI + NAD <-> NADH + 13PDG | 1.2.1.12 |
| 26300 | GAPDS, GAPDH-2 | T3P1 + PI + NAD <-> NADH + 13PDG | 1.2.1.12 |
| 5230 | PGK1, PGKA | 13PDG + ADP <-> 3PG + ATP | 2.7.2.3 |
| 5233 | PGK2 | 13PDG + ADP <-> 3PG + ATP | 2.7.2.3 |
| 5223 | PGAM1, PGAMA | 13PDG -> 23PDG | 5.4.2.4 |
|  |  | 23PDG + H2O -> 3PG + PI | 3.1.3.13 |
|  |  | 3PG <-> 2PG | 5.4.2.1 |
| 5224 | PGAM2, PGAMM | 13PDG <-> 23PDG | 5.4.2.4 |
|  |  | 23PDG + H2O -> 3PG + PI | 3.1.3.13 |
|  |  | 3PG <-> 2PG | 5.4.2.1 |
| 669 | BPGM | 13PDG <-> 23PDG | 5.4.2.4 |
|  |  | 23PDG + H2O <-> 3PG + PI | 3.1.3.1.3 |
|  |  | 3PG <-> 2PG | 5.4.2.1 |
| 2023 | ENO1, PPH, ENO1L1 | 2PG <-> PEP + H2O | 4.2.1.11 |
| 2026 | ENO2 | 2PG <-> PEP + H2O | 4.2.1.11 |
| 2027 | ENO3 | 2PG <-> PEP + H2O | 4.2.1.11 |
| 26237 | ENO1B | 2PG <-> PEP + H2O | 4.2.1.11 |
| 5313 | PKLR, PK1 | PEP + ADP -> PYR + ATP | 2.7.1.40 |
| 5315 | PKM2, PK3, THBP1, OIP3 | PEP + ADP -> PYR + ATP | 2.7.1.40 |
| 5160 | PDHA1, PHE1A, PDHA | PYRm + COAm + NADm -> + NADHm + CO2m + ACCOAm | 1.2.4.1 |
| 5161 | PDHA2, PDHAL | PYRm + COAm + NADm -> + NADHm + CO2m + ACCOAm | 1.2.4.1 |
| 5162 | PDHB | PYRm + COAm + NADm -> + NADHm + CO2m + ACCOAm | 1.2.4.1 |
| 1737 | DLAT, DLTA, PDC-E2 | PYRm + COAm + NADm -> + NADHm + CO2m + ACCOAm | 2.3.1.12 |
| 8050 | PDX1, E3BP | PYRm + COAm + NADm -> + NADHm + CO2m + ACCOAm | 2.3.1.12 |
| 3939 | LDHA, LDH1 | NAD + LAC <-> PYR + NADH | 1.1.1.27 |
| 3945 | LDHB | NAD + LAC <-> PYR + NADH | 1.1.1.27 |
| 3948 | LDHC, LDH3 | NAD + LAC <-> PYR + NADH | 1.1.1.27 |
| 5236 | PGM1 | G1P <-> G6P | 5.4.2.2 |
| 5237 | PGM2 | G1P <-> G6P | 5.4.2.2 |
| 5238 | PGM3 | G1P <-> G6P | 5.4.2.2 |
| 1738 | DLD, LAD, PHE3, DLDH, E3 | DLIPOm + FADm <-> LIPOm + FADH2m | 1.8.1.4 |
| 124 | ADH1 | ETH + NAD <-> ACAL + NADH | 1.1.1.1 |
| 125 | ADH2 | ETH + NAD <-> ACAL + NADH | 1.1.1.1 |
| 126 | ADH3 | ETH + NAD <-> ACAL + NADH | 1.1.1.1 |
| 127 | ADH4 | ETH + NAD <-> ACAL + NADH | 1.1.1.1 |
| 128 | ADH5 | FALD + RGT + NAD <-> FGT + NADH | 1.2.1.1 |
|  |  | ETH + NAD <-> ACAL + NADH | 1.1.1.1 |
| 130 | ADH6 | ETH + NAD <-> ACAL + NADH | 1.1.1.1 |
| 131 | ADH7 | ETH + NAD <-> ACAL + NADH | 1.1.1.1 |
| 10327 | AKR1A1, ALR, ALDR1 |  | 1.1.1.2 |
| 97 | ACYP1 |  | 3.6.1.7 |
| 98 | ACYP2 |  | 3.6.1.7 |

1.2 Citrate cycle (TCA cycle) PATH: hsa00020

| Locus ID | Gene Ab. | Reaction Stoichiometry | E.C. |
|---|---|---|---|
| 1431 | CS | ACCOAm + OAm + H2Om -> COAm + CITm | 4.1.3.7 |
| 48 | ACO1, IREB1, IRP1 | CIT <-> ICIT | 4.2.1.3 |
| 50 | ACO2 | CITm <-> ICITm | 4.2.1.3 |
| 3417 | IDH1 | ICIT + NADP -> NADPH + CO2 + AKG | 1.1.1.42 |
| 3418 | IDH2 | ICITm + NADPm -> NADPHm + CO2m + AKGm | 1.1.1.42 |
| 3419 | IDH3A | ICITm + NADm -> CO2m + NADHm + AKGm | 1.1.1.41 |
| 3420 | IDH3B | ICITm + NADm -> CO2m + NADHm + AKGm | 1.1.1.41 |
| 3421 | IDH3G | ICITm + NADm -> CO2m + NADHm + AKGm | 1.1.1.41 |
| 4967 | OGDH | AKGm + NADm + COAm -> CO2m + NADHm + SUCCOAm | 1.2.4.2 |
| 1743 | DLST, DLTS | AKGm + NADm + COAm -> CO2m + NADHm + SUCCOAm | 2.3.1.61 |
| 8802 | SUCLG1, SUCLA1 | GTPm + SUCCm + COAm <-> GDPm + PIm + SUCCOAm | 6.2.1.4 |
| 8803 | SUCLA2 | ATPm + SUCCm + COAm <-> ADPm + PIm + SUCCOAm | 6.2.1.4 |
| 2271 | FH | FUMm + H2Om <-> MALm | 4.2.1.2 |
| 4190 | MDH1 | MAL + NAD <-> NADH + OA | 1.1.1.37 |
| 4191 | MDH2 | MALm + NADm <-> NADHm + OAm | 1.1.1.37 |
| 5091 | PC, PCB | PYRm + ATPm + CO2m -> ADPm + OAm + PIm | 6.4.1.1 |
| 47 | ACLY, ATPCL, CLATP | ATP + CIT + COA + H2O -> ADP + PI + ACCOA + OA | 4.1.3.8 |
| 3657 |  |  |  |
| 5105 | PCK1 | OA + GTP -> PEP + GDP + CO2 | 4.1.1.32 |
| 5106 | PCK2, PEPCK | OAm + GTPm -> PEPm + GDPm + CO2m | 4.1.1.32 |

1.3 Pentose phosphate cycle PATH: hsa00030

TABLE 1-continued

| Locus ID | Gene Ab. | Reaction Stoichiometry | E.C. |
|---|---|---|---|
| 2539 | G6PD, G6PD1 | G6P + NADP <-> D6PGL + NADPH | 1.1.1.49 |
| 9563 | H6PD | | 1.1.1.47 |
| | | D6PGL + H2O -> D6PGC | 3.1.1.31 |
| 25796 | PGLS, 6PGL | D6PGL + H2O -> D6PGC | 3.1.1.31 |
| 5226 | PGD | D6PGC + NADP -> NADPH + CO2 + RL5P | 1.1.1.44 |
| 6120 | RPE | RL5P <-> X5P | 5.1.3.1 |
| 7086 | TKT | R5P + X5P <-> T3P1 + S7P | 2.2.1.1 |
| | | X5P + E4P <-> F6P + T3P1 | |
| 8277 | TKTL1, TKR, TKT2 | R5P + X5P <-> T3P1 + S7P | 2.2.1.1 |
| | | X5P + E4P <-> F6P + T3P1 | |
| 6888 | TALDO1 | T3P1 + S7P <-> E4P + F6P | 2.2.1.2 |
| 5631 | PRPS1, PRS I, PRS, I | R5P + ATP <-> PRPP + AMP | 2.7.6.1 |
| 5634 | PRPS2, PRS II, PRS, II | R5P + ATP <-> PRPP + AMP | 2.7.6.1 |
| 2663 | GDH | | 1.1.1.47 |

1.4 Pentose and glucuronate interconversions PATH: hsa00040

| Locus ID | Gene Ab. | Reaction Stoichiometry | E.C. |
|---|---|---|---|
| 231 | AKR1B1, AR, ALDR1, ADR | | 1.1.1.21 |
| 7359 | UGP1 | G1P + UTP -> UDPG + PPI | 2.7.7.9 |
| 7360 | UGP2, UGPP2 | G1P + UTP -> UDPG + PPI | 2.7.7.9 |
| 7358 | UGDH, UDPGDH | | 1.1.1.22 |
| 10720 | UGT2B11 | | 2.4.1.17 |
| 54658 | UGT1A1, UGT1A, GNT1, UGT1 | | 2.4.1.17 |
| 7361 | UGT1A, UGT1, UGT1A | | 2.4.1.17 |
| 7362 | UGT2B, UGT2, UGT2B | | 2.4.1.17 |
| 7363 | UGT2B4, UGT2B11 | | 2.4.1.17 |
| 7364 | UGT2B7, UGT2B9 | | 2.4.1.17 |
| 7365 | UGT2B10 | | 2.4.1.17 |
| 7366 | UGT2B15, UGT2B8 | | 2.4.1.17 |
| 7367 | UGT2B17 | | 2.4.1.17 |
| 13 | AADAC, DAC | | 3.1.1.— |
| 3991 | LIPE, LHS, HSL | | 3.1.1.— |

1.5 Fructose and mannose metabolism PATH: hsa00051

| Locus ID | Gene Ab. | Reaction Stoichiometry | E.C. |
|---|---|---|---|
| 4351 | MPI, PMI1 | MAN6P <-> F6P | 5.3.1.8 |
| 5372 | PMM1 | MAN6P <-> MAN1P | 5.4.2.8 |
| 5373 | PMM2, CDG1, CDGS | MAN6P <-> MAN1P | 5.4.2.8 |
| 2762 | GMDS | | 4.2.1.47 |
| 8790 | FPGT, GFPP | | 2.7.7.30 |
| 5207 | PFKFB1, PFRX | ATP + F6P -> ADP + F26P | 2.7.1.105 |
| | | F26P -> F6P + PI | 3.1.3.46 |
| 5208 | PFKFB2 | ATP + F6P -> ADP + F26P | 2.7.1.105 |
| | | F26P -> F6P + PI | 3.1.3.46 |
| 5209 | PFKFB3 | ATP + F6P -> ADP + F26P | 2.7.1.105 |
| | | F26P -> F6P + PI | 3.1.3.46 |
| 5210 | PFKFB4 | ATP + F6P -> ADP + F26P | 2.7.1.105 |
| | | F26P -> F6P + PI | 3.1.3.46 |
| 3795 | KHK | | 2.7.1.3 |
| 6652 | SORD | DSOT + NAD -> FRU + NADH | 1.1.1.14 |
| 2526 | FUT4, FCT3A, FUC-TIV | | 2.4.1.— |
| 2529 | FUT7 | | 2.4.1.— |
| 3036 | HAS1, HAS | | 2.4.1.— |
| 3037 | HAS2 | | 2.4.1.— |
| 8473 | OGT, O-GLCNAC | | 2.4.1.— |
| 51144 | LOC51144 | | 1.1.1.— |

1.6 Galactose metabolism PATH: hsa00052

| Locus ID | Gene Ab. | Reaction Stoichiometry | E.C. |
|---|---|---|---|
| 2584 | GALK1, GALK | GLAC + ATP -> GAL1P + ADP | 2.7.1.6 |
| 2585 | GALK2, GK2 | GLAC + ATP -> GAL1P + ADP | 2.7.1.6 |
| 2592 | GALT | UTP + GAL1P <-> PPI + UDPGAL | 2.7.7.10 |
| 2582 | GALE | UDPGAL <-> UDPG | 5.1.3.2 |
| 2720 | GLB1 | | 3.2.1.23 |
| 3938 | LCT, LAC | | 3.2.1.62 |
| | | | 3.2.1.108 |
| 2683 | B4GALT1, GGTB2, BETA4GAL-T1, GT1, GTB | | 2.4.1.90 |
| | | | 2.4.1.38 |
| | | | 2.4.1.22 |
| 3906 | LALBA | | 2.4.1.22 |
| 2717 | GLA, GALA | MELI -> GLC + GLAC | 3.2.1.22 |
| 2548 | GAA | MLT -> 2 GLC | 3.2.1.20 |
| | | 6DGLC -> GLAC + GLC | |
| 2594 | GANAB | MLT -> 2 GLC | 3.2.1.20 |
| | | 6DGLC -> GLAC + GLC | |
| 2595 | GANC | MLT -> 2 GLC | 3.2.1.20 |
| | | 6DGLC -> GLAC + GLC | |
| 8972 | MGAM, MG, MGA | MLT -> 2 GLC | 3.2.1.20 |
| | | 6DGLC -> GLAC + GLC | 3.2.1.3 |

1.7 Ascorbate and aldarate metabolism PATH: hsa00053

TABLE 1-continued

| Locus ID | Gene Ab. | Reaction Stoichiometry | E.C. |
|---|---|---|---|
| 216 | ALDH1, PUMB1 | ACAL + NAD -> NADH + AC | 1.2.1.3 |
| 217 | ALDH2 | ACALm + NADm -> NADHm + ACm | 1.2.1.3 |
| 219 | ALDH5, ALDHX | | 1.2.1.3 |
| 223 | ALDH9, E3 | | 1.2.1.3 |
| | | | 1.2.1.19 |
| 224 | ALDH10, FALDH, SLS | | 1.2.1.3 |
| 8854 | RALDH2 | | 1.2.1.3 |
| 1591 | CYP24 | | 1.14.—.— |
| 1592 | CYP26A1, P450RAI | | 1.14.—.— |
| 1593 | CYP27A1, CTX, CYP27 | | 1.14.—.— |
| 1594 | CYP27B1, PDDR, VDD1, VDR, CYP1, VDDR, I, P450C1 | | 1.14.—.— |

1.8 Pyruvate metabolism PATH: hsa00620

| Locus ID | Gene Ab. | Reaction Stoichiometry | E.C. |
|---|---|---|---|
| 54988 | FLJ20581 | ATP + AC + COA -> AMP + PPI + ACCOA | 6.2.1.1 |
| 31 | ACACA, ACAC, ACC | ACCOA + ATP + CO2 <-> MALCOA + ADP + PI + H | 6.4.1.2 |
| | | | 6.3.4.14 |
| 32 | ACACB, ACCB, HACC275, ACC2 | ACCOA + ATP + CO2 <-> MALCOA + ADP + PI + H | 6.4.1.2 |
| | | | 6.3.4.14 |
| 2739 | GLO1, GLYI | RGT + MTHGXL <-> LGT | 4.4.1.5 |
| 3029 | HAGH, GLO2 | LGT -> RGT + LAC | 3.1.2.6 |
| 2223 | FDH | FALD + RGT + NAD <-> FGT + NADH | 1.2.1.1 |
| 9380 | GRHPR, GLXR | | 1.1.1.79 |
| 4200 | ME2 | MALm + NADm -> CO2m + NADHm + PYRm | 1.1.1.38 |
| 10873 | ME3 | MALm + NADPm -> CO2m + NADPHm + PYRm | 1.1.1.40 |
| 29897 | HUMNDME | MAL + NADP -> CO2 + NADPH + PYR | 1.1.1.40 |
| 4199 | ME1 | MAL + NADP -> CO2 + NADPH + PYR | 1.1.1.40 |
| 38 | ACAT1, ACAT, T2, THIL, MAT | 2 ACCOAm <-> COAm + AACCOAm | 2.3.1.9 |
| 39 | ACAT2 | 2 ACCOAm <-> COAm + AACCOAm | 2.3.1.9 |

1.9 Glyoxylate and dicarboxylate metabolism PATH: hsa00630

| Locus ID | Gene Ab. | Reaction Stoichiometry | E.C. |
|---|---|---|---|
| 5240 | PGP | 3HPm + NADHm -> NADm + GLYAm | 3.1.3.18 |
| 2758 | GLYD | | 1.1.1.29 |
| 10797 | MTHFD2, NMDMC | METHF <-> FTHF | 3.5.4.9 |
| | | METTHF + NAD -> METHF + NADH | 1.5.1.15 |
| 4522 | MTHFD1 | METTHF + NADP <-> METHF + NADPH | 1.5.1.15 |
| | | METHF <-> FTHF | 3.5.4.9 |
| | | THF + FOR + ATP -> ADP + PI + FTHF | 6.3.4.3 |

1.10 Propanoate metabolism PATH: hsa00640

| Locus ID | Gene Ab. | Reaction Stoichiometry | E.C. |
|---|---|---|---|
| 34 | ACADM, MCAD | MBCOAm + FADm -> MCCOAm + FADH2m | 1.3.99.3 |
| | | IBCOAm + FADm -> MACOAm + FADH2m | |
| | | IVCOAm + FADm -> MCRCOAm + FADH2m | |
| 36 | ACADSB | MBCOAm + FADm -> MCCOAm + FADH2m | 1.3.99.3 |
| | | IBCOAm + FADm -> MACOAm + FADH2m | |
| | | IVCOAm + FADm -> MCRCOAm + FADH2m | |
| 1892 | ECHS1, SCEH | MACOAm + H2Om -> HIBCOAm | 4.2.1.17 |
| | | MCCOAm + H2Om -> MHVCOAm | |
| 1962 | EHHADH | MHVCOAm + NADm -> MAACOAm + NADHm | 1.1.1.35 |
| | | HIBm + NADm -> MMAm + NADHm | |
| | | MACOAm + H2Om -> HIBCOAm | 4.2.1.17 |
| | | MCCOAm + H2Om -> MHVCOAm | |
| 3030 | HADHA, MTPA, GBP | MHVCOAm + NADm -> MAACOAm + NADHm | 1.1.1.35 |
| | | HIBm + NADm -> MMAm + NADHm | |
| | | MACOAm + H2Om -> HIBCOAm | 4.2.1.17 |
| | | MCCOAm + H2Om -> MHVCOAm | |
| | | C16CARm + COAm + FADm + NADm -> FADH2m + NADHm + C140COAm + ACCOAm | 1.1.1.35 |
| | | | 4.2.1.17 |
| 23417 | MLYCD, MCD | | 4.1.1.9 |
| 18 | ABAT, GABAT | GABA + AKG -> SUCCSAL + GLU | 2.6.1.19 |
| 5095 | PCCA | PROPCOAm + CO2m + ATPm -> ADPm + PIm + DMMCOAm | 6.4.1.3 |
| 5096 | PCCB | PROPCOAm + CO2m + ATPm -> ADPm + PIm + DMMCOAm | 6.4.1.3 |
| 4594 | MUT, MCM | LMMCOAm -> SUCCOAm | 5.4.99.2 |
| 4329 | MMSDH | MMAm + COAm + NADm -> NADHm + CO2m + PROPCOAm | 1.2.1.27 |
| 8523 | FACVL1, VLCS, VLACS | | 6.2.1.— |

1.11 Butanoate metabolism PATH: hsa00650

| Locus ID | Gene Ab. | Reaction Stoichiometry | E.C. |
|---|---|---|---|
| 3028 | HADH2, ERAB | C140COAm + 7 COAm + 7 FADm + 7 NADm -> 7 FADH2m + 7 NADHm + 7 ACCOAm | 1.1.1.35 |
| 3033 | HADHSC, SCHAD | | 1.1.1.35 |
| 35 | ACADS, SCAD | MBCOAm + FADm -> MCCOAm + FADH2m | 1.3.99.2 |
| | | IBCOAm + FADm -> MACOAm + FADH2m | |
| 7915 | ALDH5A1, SSADH, SSDH | | 1.2.1.24 |
| 2571 | GAD1, GAD, GAD67, GAD25 | GLU -> GABA + CO2 | 4.1.1.15 |
| 2572 | GAD2 | GLU -> GABA + CO2 | 4.1.1.15 |
| 2573 | GAD3 | GLU -> GABA + CO2 | 4.1.1.15 |

TABLE 1-continued

| Locus ID | Gene Ab. | Reaction Stoichiometry | E.C. |
|---|---|---|---|
| 3157 | HMGCS1, HMGCS | H3MCOA + COA <-> ACCOA + AACCOA | 4.1.3.5 |
| 3158 | HMGCS2 | H3MCOA + COA <-> ACCOA + AACCOA | 4.1.3.5 |
| 3155 | HMGCL, HL | H3MCOAm -> ACCOAm + ACTACm | 4.1.3.4 |
| 5019 | OXCT | | 2.8.3.5 |
| 622 | BDH | 3HBm + NADm -> NADHm + Hm + ACTACm | 1.1.1.30 |
| 1629 | DBT, BCATE2 | OMVALm + COAm + NADm -> MBCOAm + NADHm + CO2m<br>OIVALm + COAm + NADm -> IBCOAm + NADHm + CO2m<br>OICAPm + COAm + NADHm -> IVCOAm + NADHm + CO2m | 2.3.1.— |

1.13 Inositol metabolism PATH: hsa00031
2. Energy Metabolism
2.1 Oxidative phosphorylation PATH: hsa00190

| Locus ID | Gene Ab. | Reaction Stoichiometry | E.C. |
|---|---|---|---|
| 4535 | MTND1 | NADHm + Qm + 4 Hm -> QH2m + NADm + 4 H | 1.6.5.3 |
| 4536 | MTND2 | NADHm + Qm + 4 Hm -> QH2m + NADm + 4 H | 1.6.5.3 |
| 4537 | MTND3 | NADHm + Qm + 4 Hm -> QH2m + NADm + 4 H | 1.6.5.3 |
| 4538 | MTND4 | NADHm + Qm + 4 Hm -> QH2m + NADm + 4 H | 1.6.5.3 |
| 4539 | MTND4L | NADHm + Qm + 4 Hm -> QH2m + NADm + 4 H | 1.6.5.3 |
| 4540 | MTND5 | NADHm + Qm + 4 Hm -> QH2m + NADm + 4 H | 1.6.5.3 |
| 4541 | MTND6 | NADHm + Qm + 4 Hm -> QH2m + NADm + 4 H | 1.6.5.3 |
| 4694 | NDUFA1, MWFE | NADHm + Qm + 4 Hm -> QH2m + NADm + 4 H | 1.6.5.3 |
| 4695 | NDUFA2, B8 | NADHm + Qm + 4 Hm -> QH2m + NADm + 4 H<br>NADHm + Qm + 4 Hm -> QH2m + NADm + 4 H | 1.6.5.3<br>1.6.99.3 |
| 4696 | NDUFA3, B9 | NADHm + Qm + 4 Hm -> QH2m + NADm + 4 H<br>NADHm + Qm + 4 Hm -> QH2m + NADm + 4 H | 1.6.5.3<br>1.6.99.3 |
| 4697 | NDUFA4, MLRQ | NADHm + Qm + 4 Hm -> QH2m + NADm + 4 H<br>NADHm + Qm + 4 Hm -> QH2m + NADm + 4 H | 1.6.5.3<br>1.6.99.3 |
| 4698 | NDUFA5, UQOR13, B13 | NADHm + Qm + 4 Hm -> QH2m + NADm + 4 H<br>NADHm + Qm + 4 Hm -> QH2m + NADm + 4 H | 1.6.5.3<br>1.6.99.3 |
| 4700 | NDUFA6, B14 | NADHm + Qm + 4 Hm -> QH2m + NADm + 4 H<br>NADHm + Qm + 4 Hm -> QH2m + NADm + 4 H | 1.6.5.3<br>1.6.99.3 |
| 4701 | NDUFA7, B14.5a, B14.5A | NADHm + Qm + 4 Hm -> QH2m + NADm + 4 H<br>NADHm + Qm + 4 Hm -> QH2m + NADm + 4 H | 1.6.5.3<br>1.6.99.3 |
| 4702 | NDUFA8, PGIV | NADHm + Qm + 4 Hm -> QH2m + NADm + 4 H<br>NADHm + Qm + 4 Hm -> QH2m + NADm + 4 H | 1.6.5.3<br>1.6.99.3 |
| 4704 | NDUFA9, NDUFS2L | NADHm + Qm + 4 Hm -> QH2m + NADm + 4 H<br>NADHm + Qm + 4 Hm -> QH2m + NADm + 4 H | 1.6.5.3<br>1.6.99.3 |
| 4705 | NDUFA10 | NADHm + Qm + 4 Hm -> QH2m + NADm + 4 H<br>NADHm + Qm + 4 Hm -> QH2m + NADm + 4 H | 1.6.5.3<br>1.6.99.3 |
| 4706 | NDUFAB1, SDAP | NADHm + Qm + 4 Hm -> QH2m + NADm + 4 H<br>NADHm + Qm + 4 Hm -> QH2m + NADm + 4 H | 1.6.5.3<br>1.6.99.3 |
| 4707 | NDUFB1, MNLL, CI-SGDH | NADHm + Qm + 4 Hm -> QH2m + NADm + 4 H<br>NADHm + Qm + 4 Hm -> QH2m + NADm + 4 H | 1.6.5.3<br>1.6.99.3 |
| 4708 | NDUFB2, AGGG | NADHm + Qm + 4 Hm -> QH2m + NADm + 4 H<br>NADHm + Qm + 4 Hm -> QH2m + NADm + 4 H | 1.6.5.3<br>1.6.99.3 |
| 4709 | NDUFB3, B12 | NADHm + Qm + 4 Hm -> QH2m + NADm + 4 H<br>NADHm + Qm + 4 Hm -> QH2m + NADm + 4 H | 1.6.5.3<br>1.6.99.3 |
| 4710 | NDUFB4, B15 | NADHm + Qm + 4 Hm -> QH2m + NADm + 4 H<br>NADHm + Qm + 4 Hm -> QH2m + NADm + 4 H | 1.6.5.3<br>1.6.99.3 |
| 4711 | NDUFB5, SGDH | NADHm + Qm + 4 Hm -> QH2m + NADm + 4 H<br>NADHm + Qm + 4 Hm -> QH2m + NADm + 4 H | 1.6.5.3<br>1.6.99.3 |
| 4712 | NDUFB6, B17 | NADHm + Qm + 4 Hm -> QH2m + NADm + 4 H<br>NADHm + Qm + 4 Hm -> QH2m + NADm + 4 H | 1.6.5.3<br>1.6.99.3 |
| 4713 | NDUFB7, B18 | NADHm + Qm + 4 Hm -> QH2m + NADm + 4 H<br>NADHm + Qm + 4 Hm -> QH2m + NADm + 4 H | 1.6.5.3<br>1.6.99.3 |
| 4714 | NDUFB8, ASHI | NADHm + Qm + 4 Hm -> QH2m + NADm + 4 H<br>NADHm + Qm + 4 Hm -> QH2m + NADm + 4 H | 1.6.5.3<br>1.6.99.3 |
| 4715 | NDUFB9, UQOR22, B22 | NADHm + Qm + 4 Hm -> QH2m + NADm + 4 H<br>NADHm + Qm + 4 Hm -> QH2m + NADm + 4 H | 1.6.5.3<br>1.6.99.3 |
| 4716 | NDUFB10, PDSW | NADHm + Qm + 4 Hm -> QH2m + NADm + 4 H<br>NADHm + Qm + 4 Hm -> QH2m + NADm + 4 H | 1.6.5.3<br>1.6.99.3 |
| 4717 | NDUFC1, KFYI | NADHm + Qm + 4 Hm -> QH2m + NADm + 4 H<br>NADHm + Qm + 4 Hm -> QH2m + NADm + 4 H | 1.6.5.3<br>1.6.99.3 |
| 4718 | NDUFC2, B14.5b, B14.5B | NADHm + Qm + 4 Hm -> QH2m + NADm + 4 H<br>NADHm + Qm + 4 Hm -> QH2m + NADm + 4 H | 1.6.5.3<br>1.6.99.3 |
| 4724 | NDUFS4, AQDQ | NADHm + Qm + 4 Hm -> QH2m + NADm + 4 H<br>NADHm + Qm + 4 Hm -> QH2m + NADm + 4 H | 1.6.5.3<br>1.6.99.3 |
| 4725 | NDUFS5 | NADHm + Qm + 4 Hm -> QH2m + NADm + 4 H<br>NADHm + Qm + 4 Hm -> QH2m + NADm + 4 H | 1.6.5.3<br>1.6.99.3 |
| 4726 | NDUFS6 | NADHm + Qm + 4 Hm -> QH2m + NADm + 4 H<br>NADHm + Qm + 4 Hm -> QH2m + NADm + 4 H | 1.6.5.3<br>1.6.99.3 |
| 4731 | NDUFV3 | NADHm + Qm + 4 Hm -> QH2m + NADm + 4 H | 1.6.5.3 |
| 4727 | NDUFS7, PSST | NADHm + Qm + 4 Hm -> QH2m + NADm + 4 H<br>NADHm + Qm + 4 Hm -> QH2m + NADm + 4 H | 1.6.5.3<br>1.6.99.3 |
| 4722 | NDUFS3 | NADHm + Qm + 4 Hm -> QH2m + NADm + 4 H<br>NADHm + Qm + 4 Hm -> QH2m + NADm + 4 H | 1.6.5.3<br>1.6.99.3 |
| 4720 | NDUFS2 | NADHm + Qm + 4 Hm -> QH2m + NADm + 4 H | 1.6.5.3 |
| 4729 | NDUFV2 | NADHm + Qm + 4 Hm -> QH2m + NADm + 4 H | 1.6.5.3 |

TABLE 1-continued

| Locus ID | Gene Ab. | Reaction Stoichiometry | E.C. |
|---|---|---|---|
| | | NADHm + Qm + 4 Hm -> QH2m + NADm + 4 H | 1.6.99.3 |
| 4723 | NDUFV1, UQOR1 | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 4719 | NDUFS1, PRO1304 | NADHm + Qm + 4 Hm -> QH2m + NADm + 4 H | 1.6.5.3 |
| 4728 | NDUFS8 | NADHm + Qm + 4 Hm -> QH2m + NADm + 4 H | 1.6.5.3 |
| | | NADHm + Qm + 4 Hm -> QH2m + NADm + 4 H | 1.6.99.3 |
| 6391 | SDHC | SUCCm + FADm <-> FUMm + FADH2m | 1.3.5.1 |
| | | FADH2m + Qm <-> FADm + QH2m | |
| 6392 | SDHD, CBT1, PGL, PGL1 | SUCCm + FADm <-> FUMm + FADH2m | 1.3.5.1 |
| | | FADH2m + Qm <-> FADm + QH2m | |
| 6389 | SDHA, SDH2, SDHF, FP | SUCCm + FADm <-> FUMm + FADH2m | 1.3.5.1 |
| | | FADH2m + Qm <-> FADm + QH2m | |
| 6390 | SDHB, SDH1, IP, SDH | SUCCm + FADm <-> FUMm + FADH2m | 1.3.5.1 |
| | | FADH2m + Qm <-> FADm + QH2m | |
| 7386 | UQCRFS1, RIS1 | O2m + 4 FEROm + 4 Hm -> 4 FERIm + 2 H2Om + 4 H | 1.10.2.2 |
| 4519 | MTCYB | O2m + 4 FEROm + 4 Hm -> 4 FERIm + 2 H2Om + 4 H | 1.10.2.2 |
| 1537 | CYC1 | O2m + 4 FEROm + 4 Hm -> 4 FERIm + 2 H2Om + 4 H | 1.10.2.2 |
| 7384 | UQCRC1, D3S3191 | O2m + 4 FEROm + 4 Hm -> 4 FERIm + 2 H2Om + 4 H | 1.10.2.2 |
| 7385 | UQCRC2 | O2m + 4 FEROm + 4 Hm -> 4 FERIm + 2 H2Om + 4 H | 1.10.2.2 |
| 7388 | UQCRH | O2m + 4 FEROm + 4 Hm -> 4 FERIm + 2 H2Om + 4 H | 1.10.2.2 |
| 7381 | UQCRB, QPC, UQBP, QP-C | O2m + 4 FEROm + 4 Hm -> 4 FERIm + 2 H2Om + 4 H | 1.10.2.2 |
| 27089 | QP-C | O2m + 4 FEROm + 4 Hm -> 4 FERIm + 2 H2Om + 4 H | 1.10.2.2 |
| 10975 | UQCR | O2m + 4 FEROm + 4 Hm -> 4 FERIm + 2 H2Om + 4 H | 1.10.2.2 |
| 1333 | COX5BL4 | QH2m + 2 FERIm + 4 Hm -> Qm + 2 FEROm + 4 H | 1.9.3.1 |
| 4514 | MTCO3 | QH2m + 2 FERIm + 4 Hm -> Qm + 2 FEROm + 4 H | 1.9.3.1 |
| 4512 | MTCO1 | QH2m + 2 FERIm + 4 Hm -> Qm + 2 FEROm + 4 H | 1.9.3.1 |
| 4513 | MTCO2 | QH2m + 2 FERIm + 4 Hm -> Qm + 2 FEROm + 4 H | 1.9.3.1 |
| 1329 | COX5B | QH2m + 2 FERIm + 4 Hm -> Qm + 2 FEROm + 4 H | 1.9.3.1 |
| 1327 | COX4 | QH2m + 2 FERIm + 4 Hm -> Qm + 2 FEROm + 4 H | 1.9.3.1 |
| 1337 | COX6A1, COX6A | QH2m + 2 FERIm + 4 Hm -> Qm + 2 FEROm + 4 H | 1.9.3.1 |
| 1339 | COX6A2 | QH2m + 2 FERIm + 4 Hm -> Qm + 2 FEROm + 4 H | 1.9.3.1 |
| 1340 | COX6B | QH2m + 2 FERIm + 4 Hm -> Qm + 2 FEROm + 4 H | 1.9.3.1 |
| 1345 | COX6C | QH2m + 2 FERIm + 4 Hm -> Qm + 2 FEROm + 4 H | 1.9.3.1 |
| 9377 | COX5A, COX, VA, COX-VA | QH2m + 2 FERIm + 4 Hm -> Qm + 2 FEROm + 4 H | 1.9.3.1 |
| 1346 | COX7A1, COX7AM, COX7A | QH2m + 2 FERIm + 4 Hm -> Qm + 2 FEROm + 4 H | 1.9.3.1 |
| 1347 | COX7A2, COX VIIa-L | QH2m + 2 FERIm + 4 Hm -> Qm + 2 FEROm + 4 H | 1.9.3.1 |
| 1348 | COX7A3 | QH2m + 2 FERIm + 4 Hm -> Qm + 2 FEROm + 4 H | 1.9.3.1 |
| 1349 | COX7B | QH2m + 2 FERIm + 4 Hm -> Qm + 2 FEROm + 4 H | 1.9.3.1 |
| 9167 | COX7A2L, COX7RP, EB1 | QH2m + 2 FERIm + 4 Hm -> Qm + 2 FEROm + 4 H | 1.9.3.1 |
| 1350 | COX7C | QH2m + 2 FERIm + 4 Hm -> Qm + 2 FEROm + 4 H | 1.9.3.1 |
| 1351 | COX8, COX VIII | QH2m + 2 FERIm + 4 Hm -> Qm + 2 FEROm + 4 H | 1.9.3.1 |
| 4508 | MTATP6 | ADPm + Pim + 3 H -> ATPm + 3 Hm + H2Om | 3.6.1.34 |
| 4509 | MTATP8 | ADPm + Pim + 3 H -> ATPm + 3 Hm + H2Om | 3.6.1.34 |
| 499 | ATP5A2 | ADPm + Pim + 3 H -> ATPm + 3 Hm + H2Om | 3.6.1.34 |
| 507 | ATP5BL1, ATPSBL1 | ADPm + Pim + 3 H -> ATPm + 3 Hm + H2Om | 3.6.1.34 |
| 508 | ATP5BL2, ATPSBL2 | ADPm + Pim + 3 H -> ATPm + 3 Hm + H2Om | 3.6.1.34 |
| 519 | ATP5H | ADPm + Pim + 3 H -> ATPm + 3 Hm + H2Om | 3.6.1.34 |
| 537 | ATP6S1, ORF, VATPS1, XAP-3 | ADPm + Pim + 3 H -> ATPm + 3 Hm + H2Om | 3.6.1.34 |
| 514 | ATP5E | ADPm + Pim + 3 H -> ATPm + 3 Hm + H2Om | 3.6.1.34 |
| 513 | ATP5D | ADPm + Pim + 3 H -> ATPm + 3 Hm + H2Om | 3.6.1.34 |
| 506 | ATP5B, ATPSB | ADPm + Pim + 3 H -> ATPm + 3 Hm + H2Om | 3.6.1.34 |
| 509 | ATP5C1, ATP5C | ADPm + Pim + 3 H -> ATPm + 3 Hm + H2Om | 3.6.1.34 |
| 498 | ATP5A1, ATP5A, ATPM, OMR, HATP1 | ADPm + Pim + 3 H -> ATPm + 3 Hm + H2Om | 3.6.1.34 |
| 539 | ATP5O, ATPO, OSCP | ADPm + Pim + 3 H -> ATPm + 3 Hm + H2Om | 3.6.1.34 |
| 516 | ATP5G1, ATP5G | ADPm + Pim + 3 H -> ATPm + 3 Hm + H2Om | 3.6.1.34 |
| 517 | ATP5G2 | ADPm + Pim + 3 H -> ATPm + 3 Hm + H2Om | 3.6.1.34 |
| 518 | ATP5G3 | ADPm + Pim + 3 H -> ATPm + 3 Hm + H2Om | 3.6.1.34 |
| 515 | ATP5F1 | ADPm + Pim + 3 H -> ATPm + 3 Hm + H2Om | 3.6.1.34 |
| 521 | ATP5I | ADPm + Pim + 3 H -> ATPm + 3 Hm + H2Om | 3.6.1.34 |
| 522 | ATP5J, ATP5A, ATPM, ATP5 | ADPm + Pim + 3 H -> ATPm + 3 Hm + H2Om | 3.6.1.34 |
| 9551 | ATP5J2, ATP5JL, F1FO-ATPASE | ADPm + Pim + 3 H -> ATPm + 3 Hm + H2Om | 3.6.1.34 |
| 10476 | ATP5JD | ADPm + Pim + 3 H -> ATPm + 3 Hm + H2Om | 3.6.1.34 |
| 10632 | ATP5JG | ADPm + Pim + 3 H -> ATPm + 3 Hm + H2Om | 3.6.1.34 |
| 9296 | ATP6S14 | ADPm + Pim + 3 H -> ATPm + 3 Hm + H2Om | 3.6.1.34 |
| 528 | ATP6D | ADPm + Pim + 3 H -> ATPm + 3 Hm + H2Om | 3.6.1.34 |
| 523 | ATP6A1, VPP2 | ADPm + Pim + 3 H -> ATPm + 3 Hm + H2Om | 3.6.1.34 |
| 524 | ATP6A2, VPP2 | ADPm + Pim + 3 H -> ATPm + 3 Hm + H2Om | 3.6.1.34 |
| 525 | ATP6B1, VPP3, VATB | ADPm + Pim + 3 H -> ATPm + 3 Hm + H2Om | 3.6.1.34 |
| 526 | ATP6B2, VPP3 | ADPm + Pim + 3 H -> ATPm + 3 Hm + H2Om | 3.6.1.34 |
| 529 | ATP6E | ADPm + Pim + 3 H -> ATPm + 3 Hm + H2Om | 3.6.1.34 |
| 527 | ATP6C, ATPL | ADPm + Pim + 3 H -> ATPm + 3 Hm + H2Om | 3.6.1.34 |
| 533 | ATP6F | ADPm + Pim + 3 H -> ATPm + 3 Hm + H2Om | 3.6.1.34 |
| 10312 | TCIRG1, TIRC7, OC-116, OC-116kDa, OC-116KDA, ATP6N1C | ADPm + Pim + 3 H -> ATPm + 3 Hm + H2Om | 3.6.1.34 |
| 23545 | TJ6 | ADPm + Pim + 3 H -> ATPm + 3 Hm + H2Om | 3.6.1.34 |
| 50617 | ATP6N1B | ADPm + Pim + 3 H -> ATPm + 3 Hm + H2Om | 3.6.1.34 |

TABLE 1-continued

| Locus ID | Gene Ab. | Reaction Stoichiometry | E.C. |
|---|---|---|---|
| 535 | ATP6N1 | ADPm + Pim + 3 H -> ATPm + 3 Hm + H2Om | 3.6.1.34 |
| 51382 | VATD | ADPm + Pim + 3 H -> ATPm + 3 Hm + H2Om | 3.6.1.34 |
| 8992 | ATP6H | ADPm + Pim + 3 H -> ATPm + 3 Hm + H2Om | 3.6.1.34 |
| 9550 | ATP6J | ADPm + Pim + 3 H -> ATPm + 3 Hm + H2Om | 3.6.1.34 |
| 51606 | LOC51606 | ADPm + Pim + 3 H -> ATPm + 3 Hm + H2Om | 3.6.1.34 |
| 495 | ATP4A, ATP6A | ATP + H + Kxt + H2O <-> ADP + PI + Hext + K | 3.6.1.36 |
| 496 | ATP4B, ATP6B | ATP + H + Kxt + H2O <-> ADP + PI + Hext + K | 3.6.1.36 |
| 476 | ATP1A1 | ATP + 3 NA + 2 Kxt + H2O <-> ADP + 3 NAxt + 2 K + PI | 3.6.1.37 |
| 477 | ATP1A2 | ATP + 3 NA + 2 Kxt + H2O <-> ADP + 3 NAxt + 2 K + PI | 3.6.1.37 |
| 478 | ATP1A3 | ATP + 3 NA + 2 Kxt + H2O <-> ADP + 3 NAxt + 2 K + PI | 3.6.1.37 |
| 479 | ATP1AL1 | ATP + 3 NA + 2 Kxt + H2O <-> ADP + 3 NAxt + 2 K + PI | 3.6.1.37 |
| 23439 | ATP1B4 | ATP + 3 NA + 2 Kxt + H2O <-> ADP + 3 NAxt + 2 K + PI | 3.6.1.37 |
| 481 | ATP1B1, ATP1B | ATP + 3 NA + 2 Kxt + H2O <-> ADP + 3 NAxt + 2 K + PI | 3.6.1.37 |
| 482 | ATP1B2, AMOG | ATP + 3 NA + 2 Kxt + H2O <-> ADP + 3 NAxt + 2 K + PI | 3.6.1.37 |
| 483 | ATP1B3 | ATP + 3 NA + 2 Kxt + H2O <-> ADP + 3 NAxt + 2 K + PI | 3.6.1.37 |
| 27032 | ATP2C1, ATP2C1A, PMR1 | ATP + 2 CA + H2O <-> ADP + PI + 2 CAxt | 3.6.1.38 |
| 487 | ATP2A1, SERCA1, ATP2A | ATP + 2 CA + H2O <-> ADP + PI + 2 CAxt | 3.6.1.38 |
| 488 | ATP2A2, ATP2B, SERCA2, DAR, DD | ATP + 2 CA + H2O <-> ADP + PI + 2 CAxt | 3.6.1.38 |
| 489 | ATP2A3, SERCA3 | ATP + 2 CA + H2O <-> ADP + PI + 2 CAxt | 3.6.1.38 |
| 490 | ATP2B1, PMCA1 | ATP + 2 CA + H2O <-> ADP + PI + 2 CAxt | 3.6.1.38 |
| 491 | ATP2B2, PMCA2 | ATP + 2 CA + H2O <-> ADP + PI + 2 CAxt | 3.6.1.38 |
| 492 | ATP2B3, PMCA3 | ATP + 2 CA + H2O <-> ADP + PI + 2 CAxt | 3.6.1.38 |
| 493 | ATP2B4, ATP2B2, PMCA4 | ATP + 2 CA + H2O <-> ADP + PI + 2 CAxt | 3.6.1.38 |
| 538 | ATP7A, MK, MNK, OHS | ATP + H2O + Cu2 -> ADP + PI + Cu2xt | 3.6.3.4 |
| 540 | ATP7B, WND | ATP + H20 + Cu2 -> ADP + PI + Cu2xt | 3.6.3.4 |
| 5464 | PP, SID6-8061 | PPI -> 2 PI | 3.6.1.1 |

2.2 Photosynthesis PATH: hsa00195
2.3 Carbon fixation PATH: hsa00710

| | | | |
|---|---|---|---|
| 2805 | GOT1 | OAm + GLUm <-> ASPm + AKGm | 2.6.1.1 |
| 2806 | GOT2 | OA + GLU <-> ASP + AKG | 2.6.1.1 |
| 2875 | GPT | PYR + GLU <-> AKG + ALA | 2.6.1.2 |

2.4 Reductive carboxylate cycle (CO2 fixation) PATH: hsa00720
2.5 Methane metabolism PATH: hsa00680

| | | | |
|---|---|---|---|
| 847 | CAT | 2H2O2 -> O2 | 1.11.1.6 |
| 4025 | LPO, SPO | | 1.11.1.7 |
| 4353 | MPO | | 1.11.1.7 |
| 8288 | EPX, EPX-PEN, EPO, EPP | | 1.11.1.7 |
| 9588 | KIAA0106, AOP2 | | 1.11.1.7 |
| 6470 | SHMT1, CSHMT | THF + SER <-> GLY + METTHF | 2.1.2.1 |
| 6472 | SHMT2, GLYA, SHMT | THFm + SERm <-> GLYm + METTHFm | 2.1.2.1 |
| 51004 | LOC51004 | 2OPMPm + O2m -> 2OPMBm<br>2OPMMBm + O2m -> 2OMHMBm | 1.14.13.— |
| 9420 | CYP7B1 | 2OPMPm + O2m -> 2OPMBm<br>2OPMMBm + O2m -> 2OMHMBm | 1.14.13.— |

2.6 Nitrogen metabolism PATH: hsa00910

| | | | |
|---|---|---|---|
| 11238 | CA5B | | 4.2.1.1 |
| 23632 | CA14 | | 4.2.1.1 |
| 759 | CA1 | | 4.2.1.1 |
| 760 | CA2 | | 4.2.1.1 |
| 761 | CA3, CAIII | | 4.2.1.1 |
| 762 | CA4, CAIV | | 4.2.1.1 |
| 763 | CA5A, CA5, CAV, CAVA | | 4.2.1.1 |
| 765 | CA6 | | 4.2.1.1 |
| 766 | CA7 | | 4.2.1.1 |
| 767 | CA8, CALS, CARP | | 4.2.1.1 |
| 768 | CA9, MN | | 4.2.1.1 |
| 770 | CA11, CARP2 | | 4.2.1.1 |
| 771 | CA12 | | 4.2.1.1 |
| 1373 | CPS1 | GLUm + CO2m + 2 ATPm -> 2 ADPm + 2 PIm + CAPm | 6.3.4.16 |
| 275 | AMT | GLYm + THFm + NADm <-> METTHFm + NADHm + CO2m + NH3m | 2.1.2.10 |
| 3034 | HAL, HSTD, HIS | HIS -> NH3 + URO | 4.3.1.3 |
| 2746 | GLUD1, GLUD | AKGm + NADHm + NH3m <-> NADm + H2Om + GLUm<br>AKGm + NADPHm + NH3m <-> NADPm + H2Om + GLUm | 1.4.1.3 |
| 8307 | GLUD2 | AKGm + NADHm + NH3m <-> NADm + H2Om + GLUm<br>AKGm + NADPHm + NH3m <-> NADPm + H2Om + GLUm | 1.4.1.3 |
| 2752 | GLUL, GLNS | GLUm + NH3m + ATPm -> GLNm + ADPm + Pim | 6.3.1.2 |
| 22842 | KIAA0838 | GLN -> GLU + NH3 | 3.5.1.2 |
| 27165 | GA | GLN -> GLU + NH3 | 3.5.1.2 |
| 2744 | GLS | GLNm -> GLUm + NH3m | 3.5.1.2 |
| 440 | ASNS | ASPm + ATPm + GLNm -> GLUm + ASNm + AMPm + PPIm | 6.3.5.4 |
| 1491 | CTH | LLCT + H2O -> CYS + HSER<br>OBUT + NH3 <-> HSER | 4.4.1.1<br>4.4.1.1 |

2.7 Sulfur metabolism PATH: hsa00920

TABLE 1-continued

| Locus ID | Gene Ab. | Reaction Stoichiometry | E.C. |
|---|---|---|---|
| 9060 | PAPSS2, ATPSK2, SK2 | APS + ATP -> ADP + PAPS | 2.7.1.25 |
|  |  | SLF + ATP -> PPI + APS | 2.7.7.4 |
| 9061 | PAPSS1, ATPSK1, SK1 | APS + ATP -> ADP + PAPS | 2.7.1.25 |
|  |  | SLF + ATP -> PPI + APS | 2.7.7.4 |
| 10380 | BPNT1 | PAP -> AMP + PI | 3.1.3.7 |
| 6799 | SULT1A2 |  | 2.8.2.1 |
| 6817 | SULT1A1, STP1 |  | 2.8.2.1 |
| 6818 | SULT1A3, STM |  | 2.8.2.1. |
| 6822 | SULT2A1, STD |  | 2.8.2.2 |
| 6783 | STE, EST |  | 2.8.2.4 |
| 6821 | SUOX |  | 1.8.3.1 |

3. Lipid Metabolism
3.1 Fatty acid biosynthesis (path 1) PATH: hsa00061

| Locus ID | Gene Ab. | Reaction Stoichiometry | E.C. |
|---|---|---|---|
| 2194 | FASN |  | 2.3.1.85 |

3.2 Fatty acid biosynthesis (path 2) PATH: hsa00062

| Locus ID | Gene Ab. | Reaction Stoichiometry | E.C. |
|---|---|---|---|
| 10449 | ACAA2, DSAEC | MAACOAm -> ACCOAm + PROPCOAm | 2.3.1.16 |
| 30 | ACAA1, ACAA | MAACOA -> ACCOA + PROPCOA | 2.3.1.16 |
| 3032 | HADHB | MAACOA -> ACCOA + PROPCOA | 2.3.1.16 |

3.3 Fatty acid metabolism PATH: hsa00071

| Locus ID | Gene Ab. | Reaction Stoichiometry | E.C. |
|---|---|---|---|
| 51 | ACOX1, ACOX |  | 1.3.3.6 |
| 33 | ACADL, LCAD |  | 1.3.99.13 |
| 2639 | GCDH |  | 1.3.99.7 |
| 2179 | FACL1, LACS | ATP + LCCA + COA <-> AMP + PPI + ACOA | 6.2.1.3 |
| 2180 | FACL2, FACL1, LACS2 | ATP + LCCA + COA <-> AMP + PPI + ACOA | 6.2.1.3 |
| 2182 | FACL4, ACS4 | ATP + LCCA + COA <-> AMP + PPI + ACOA | 6.2.1.3 |
| 1374 | CPT1A, CPT1, CPT1-L |  | 2.3.1.21 |
| 1375 | CPT1B, CPT1-M |  | 2.3.1.21 |
| 1376 | CPT2, CPT1, CPTASE |  | 2.3.1.21 |
| 1632 | DCI |  | 5.3.3.8 |
| 11283 | CYP4F8 |  | 1.14.14.1 |
| 1543 | CYP1A1, CYP1 |  | 1.14.14.1 |
| 1544 | CYP1A2 |  | 1.14.14.1 |
| 1545 | CYP1B1, GLC3A |  | 1.14.14.1 |
| 1548 | CYP2A6, CYP2A3 |  | 1.14.14.1 |
| 1549 | CYP2A7 |  | 1.14.14.1 |
| 1551 | CYP3A7 |  | 1.14.14.1 |
| 1553 | CYP2A13 |  | 1.14.14.1 |
| 1554 | CYP2B |  | 1.14.14.1 |
| 1555 | CYP2B6 |  | 1.14.14.1 |
| 1557 | CYP2C19, CYP2C, P450IIC19 |  | 1.14.14.1 |
| 1558 | CYP2C8 |  | 1.14.14.1 |
| 1559 | CYP2C9, P450IIC9, CYP2C10 |  | 1.14.14.1 |
| 1562 | CYP2C18, P450IIC17, CYP2C17 |  | 1.14.14.1 |
| 1565 | CYP2D6 |  | 1.14.14.1 |
| 1571 | CYP2E, CYP2E1, P450C2E |  | 1.14.14.1 |
| 1572 | CYP2F1, CYP2F |  | 1.14.14.1 |
| 1573 | CYP2J2 |  | 1.14.14.1 |
| 1575 | CYP3A3 |  | 1.14.14.1 |
| 1576 | CYP3A4 |  | 1.14.14.1 |
| 1577 | CYP3A5, PCN3 |  | 1.14.14.1 |
| 1580 | CYP4B1 |  | 1.14.14.1 |
| 1588 | CYP19, ARO |  | 1.14.14.1 |
| 1595 | CYP51 |  | 1.14.14.1 |
| 194 | AHHR, AHH |  | 1.14.14.1 |

3.4 Synthesis and degradation of ketone bodies PATH: hsa00072
3.5 Sterol biosynthesis PATH: hsa00100

| Locus ID | Gene Ab. | Reaction Stoichiometry | E.C. |
|---|---|---|---|
| 3156 | HMGCR | MVL + COA + 2 NADP <-> H3MCOA + 2 NADPH | 1.1.1.34 |
| 4598 | MVK, MVLK | ATP + MVL -> ADP + PMVL | 2.7.1.36 |
|  |  | CTP + MVL -> CDP + PMVL |  |
|  |  | GTP + MVL -> GDP + PMVL |  |
|  |  | UTP + MVL -> UDP + PMVL |  |
| 10654 | PMVK, PMKASE, PMK, HUMPMKI | ATP + PMVL -> ADP + PPMVL | 2.7.4.2 |
| 4597 | MVD, MPD | ATP + PPMVL -> ADP + PI + IPPP + CO2 | 4.1.1.33 |
| 3422 | IDI1 | IPPP <-> DMPP | 5.3.3.2 |
| 2224 | FDPS | GPP + IPPP -> FPP + PPI | 2.5.1.10 |
|  |  | DMPP + IPPP-> GPP + PPI | 2.5.1.1 |
| 9453 | GGPS1, GGPPS | DMPP + IPPP -> GPP + PPI | 2.5.1.1 |
|  |  | GPP + IPPP -> FPP + PPI | 2.5.1.10 |
|  |  |  | 2.5.1.29 |
| 2222 | FDFT1; DGPT | 2 FPP + NADPH -> NADP + SQL | 2.5.1.21 |
| 6713 | SQLE | SQL + O2 + NADP -> S23E + NADPH | 1.14.99.7 |
| 4047 | LSS, OSC | S23E -> LNST | 5.4.99.7 |

TABLE 1-continued

| Locus ID | Gene Ab. | Reaction Stoichiometry | E.C. |
| --- | --- | --- | --- |
| 1728 | DIA4, NMOR1, NQO1, NMORI | | 1.6.99.2 |
| 4835 | NMOR2, NQO2 | | 1.6.99.2 |
| 37 | ACADVL, VLCAD, LCACD | | 1.3.99.— |

3.6 Bile acid biosynthesis PATH: hsa00120

| Locus ID | Gene Ab. | Reaction Stoichiometry | E.C. |
| --- | --- | --- | --- |
| 1056 | CEL, BSSL, BAL | | 3.1.1.3 |
| 3988 | LIPA, LAL | | 3.1.1.13 |
| 6646 | SOAT1, ACAT, STAT, SOAT, ACAT1, ACACT | | 3.1.1.13 |
| | | | 2.3.1.26 |
| 1581 | CYP7A1, CYP7 | | 1.14.13.17 |
| 6715 | SRD5A1 | | 1.3.99.5 |
| 6716 | SRD5A2 | | 1.3.99.5 |
| 6718 | AKR1D1, SRD5B1, 3o5bred | | 1.3.99.6 |
| 570 | BAAT, BAT | | 2.3.1.65 |

3.7 C21-Steroid hormone metabolism PATH: hsa00140

| Locus ID | Gene Ab. | Reaction Stoichiometry | E.C. |
| --- | --- | --- | --- |
| 1583 | CYP11A, P450SCC | | 1.14.15.6 |
| 3283 | HSD3B1, HSD3B, HSDB3 | IMZYMST -> IIMZYMST + CO2 | 5.3.3.1 |
| | | IMZYMST -> IIZYMST + CO2 | 1.1.1.145 |
| 3284 | HSD3B2 | IMZYMST -> IIMZYMST + CO2 | 5.3.3.1 |
| | | IMZYMST -> IIZYMST + CO2 | 1.1.1.145 |
| 1589 | CYP21A2, CYP21, P450221B, CA21H, CYP21B, P450c21B | | 1.14.99.10 |
| 1586 | CYP17, P450C17 | | 1.14.99.9 |
| 1584 | CYP11B1, P450C11, CYP11B | | 1.14.15.4 |
| 1585 | CYP11B2, CYP11B | | 1.14.15.4 |
| 3290 | HSD11B1, HSD11, HSD11L, HSD11B | | 1.1.1.146 |
| 3291 | HSD11B2, HSD11K | | 1.1.1.146 |

3.8 Androgen and estrogen metabolism PATH: hsa00150

| Locus ID | Gene Ab. | Reaction Stoichiometry | E.C. |
| --- | --- | --- | --- |
| 3292 | HSD17B1, EDH17B2, EDHB17, HSD17 | | 1.1.1.62 |
| 3293 | HSD17B3, EDH17B3 | | 1.1.1.62 |
| 3294 | HSD17B2, EDH17B2 | | 1.1.1.62 |
| 3295 | HSD17B4 | | 1.1.1.62 |
| 3296 | HSD17BP1, EDH17B1, EDHB17, HSD17 | | 1.1.1.62 |
| 51478 | HSD17B7, PRAP | | 1.1.1.62 |
| 412 | STS, ARSC, ARSC1, SSDD | | 3.1.6.2 |
| 414 | ARSD | | 3.1.6.1 |
| 415 | ARSE, CDPX1, CDPXR, CDPX | | 3.1.6.1 |
| 11185 | INMT | | 2.1.1.— |
| 24140 | JM23 | | 2.1.1.— |
| 29104 | N6AMT1, PRED28 | | 2.1.1.— |
| 29960 | FJH1 | | 2.1.1.— |
| 3276 | HRMT1L2, HCP1, PRMT1 | | 2.1.1.— |
| 51628 | LOC51628 | | 2.1.1.— |
| 54743 | HASJ4442 | | 2.1.1.— |
| 27292 | HSA9761 | | 2.1.1.— |

4. Nucleotide Metabolism
4.1 Purine metabolism PATH: hsa00230

| Locus ID | Gene Ab. | Reaction Stoichiometry | E.C. |
| --- | --- | --- | --- |
| 11164 | NUDT5, HYSAH1, YSA1H | | 3.6.1.13 |
| 5471 | PPAT, GPAT | PRPP + GLN -> PPI + GLU + PRAM | 2.4.2.14 |
| 2618 | GART, PGFT, PRGS | PRAM + ATP + GLY <-> ADP + PI + GAR | 6.3.4.13 |
| | | FGAM + ATP -> ADP + PI + AIR | 6.3.3.1 |
| | | GAR + FTHF -> THF + FGAR | 2.1.2.2 |
| 5198 | PFAS, FGARAT, KIAA0361, PURL | FGAR + ATP + GLN -> GLU + ADP + PI + FGAM | 6.3.5.3 |
| 10606 | ADE2H1 | CAIR + ATP + ASP <-> ADP + PI + SAICAR | 6.3.2.6 |
| | | CAIR <-> AIR + CO2 | 4.1.1.21 |
| 5059 | PAICS, AIRC, PAIS | CAIR + ATP + ASP <-> ADP + PI + SAICAR | 6.3.2.6 |
| 158 | ADSL | ASUC <-> FUM + AMP | 4.3.2.2 |
| 471 | ATIC, PURH | AICAR + FTHF <-> THF + PRFICA | 2.1.2.3 |
| | | PRFICA <-> IMP | 3.5.4.10 |
| 3251 | HPRT1, HPRT, HGPRT | HYXAN + PRPP -> PPI + IMP | 2.4.2.8 |
| | | GN + PRPP -> PPI + GMP | |
| 3614 | IMPDH1 | IMP + NAD -> NADH + XMP | 1.1.1.205 |
| 3615 | IMPDH2 | IMP + NAD -> NADH + XMP | 1.1.1.205 |
| 8833 | GMPS | | 6.3.5.2 |
| 114923 | | | |
| 2987 | GUK1 | GMP + ATP <-> GDP + ADP | 2.7.4.8 |
| | | DGMP + ATP <-> DGDP + ADP | |
| | | GMP + DATP <-> GDP + DADP | |
| 2988 | GUK2 | GMP + ATP <-> GDP + ADP | 2.7.4.8 |
| | | DGMP + ATP <-> DGDP + ADP | |
| | | GMP + DATP <-> GDP + DADP | |
| 10621 | RPC39 | | 2.7.7.6 |

TABLE 1-continued

| Locus ID | Gene Ab. | Reaction Stoichiometry | E.C. |
|---|---|---|---|
| 10622 | RPC32 | | 2.7.7.6 |
| 10623 | RPC62 | | 2.7.7.6 |
| 11128 | RPC155 | | 2.7.7.6 |
| 25885 | DKFZP586M0122 | | 2.7.7.6 |
| 30834 | ZNRD1 | | 2.7.7.6 |
| 51082 | LOC51082 | | 2.7.7.6 |
| 51728 | LOC51728 | | 2.7.7.6 |
| 5430 | POLR2A, RPOL2, POLR2, POLRA | | 2.7.7.6 |
| 5431 | POLR2B, POL2RB | | 2.7.7.6 |
| 5432 | POLR2C | | 2.7.7.6 |
| 5433 | POLR2D, HSRBP4, HSRPB4 | | 2.7.7.6 |
| 5434 | POLR2E, RPB5, XAP4 | | 2.7.7.6 |
| 5435 | POLR2F, RPB6, HRBP14.4 | | 2.7.7.6 |
| 5436 | POLR2G, RPB7 | | 2.7.7.6 |
| 5437 | POLR2H, RPB8, RPB17 | | 2.7.7.6 |
| 5438 | POLR2I | | 2.7.7.6 |
| 5439 | POLR2J | | 2.7.7.6 |
| 5440 | POLR2K, RPB7.0 | | 2.7.7.6 |
| 5441 | POLR2L, RPB7.6, RPB10 | | 2.7.7.6 |
| 5442 | POLRMT, APOLMT | | 2.7.7.6 |
| 54479 | FLJ10816, Rpo1-2 | | 2.7.7.6 |
| 55703 | FLJ10388 | | 2.7.7.6 |
| 661 | BN51T | | 2.7.7.6 |
| 9533 | RPA40, RPA39 | | 2.7.7.6 |
| 10721 | POLQ | | 2.7.7.7 |
| 11232 | POLG2, MTPOLB, HP55, POLB | | 2.7.7.7 |
| 23649 | POLA2 | | 2.7.7.7 |
| 5422 | POLA | | 2.7.7.7 |
| 5423 | POLB | | 2.7.7.7 |
| 5424 | POLD1, POLD | | 2.7.7.7 |
| 5425 | POLD2 | | 2.7.7.7 |
| 5426 | POLE | | 2.7.7.7 |
| 5427 | POLE2 | | 2.7.7.7 |
| 5428 | POLG | | 2.7.7.7 |
| 5980 | REV3L, POLZ, REV3 | | 2.7.7.7 |
| 7498 | XDH | | 1.1.3.22 |
| 9615 | GDA, KIAA1258, CYPIN, NEDASIN | | 1.1.1.204 |
| 2766 | GMPR | | 3.5.4.3 |
| 51292 | LOC51292 | | 1.6.6.8 |
| 7377 | UOX | | 1.6.6.8 |
| 6240 | RRM1 | ADP + RTHIO -> DADP + OTHIO<br>GDP + RTHIO -> DGDP + OTHIO<br>CDP + RTHIO -> DCDP + OTHIO<br>UDP + RTHIO -> DUDP + OTHIO | 1.7.3.3<br>1.17.4.1 |
| 6241 | RRM2 | ADP + RTHIO -> DADP + OTHIO<br>GDP + RTHIO -> DGDP + OTHIO<br>CDP + RTHIO -> DCDP + OTHIO<br>UDP + RTHIO -> DUDP + OTHIO | 1.17.4.1 |
| 4860 | NP, PNP | AND + PI <-> AD + R1P<br>GSN + PI <-> GN + R1P<br>DA + PI <-> AD + R1P<br>DG + PI <-> GN + R1P<br>DIN + PI <-> HYXAN + R1P<br>INS + PI <-> HYXAN + R1P<br>XTSINE + PI <-> XAN + R1P | 2.4.2.1 |
| 1890 | ECGF1, hPD-ECGF | DU + PI <-> URA + DR1P<br>DT + PI <-> THY + DR1P | 2.4.2.4 |
| 353 | APRT | AD + PRPP -> PPI + AMP | 2.4.2.7 |
| 132 | ADK | ADN + ATP -> AMP + ADP | 2.7.1.20 |
| 1633 | DCK | | 2.7.1.74 |
| 1716 | DGUOK | | 2.7.1.113 |
| 203 | AK1 | ATP + AMP <-> 2 ADP<br>GTP + AMP <-> ADP + GDP<br>ITP + AMP <-> ADP + IDP | 2.7.4.3 |
| 204 | AK2 | ATP + AMP <-> 2 ADP<br>GTP + AMP <-> ADP + GDP<br>ITP + AMP <-> ADP + IDP | 2.7.4.3 |
| 205 | AK3 | ATP + AMP <-> 2 ADP<br>GTP + AMP <-> ADP + GDP<br>ITP + AMP <-> ADP + IDP | 2.7.4.3 |
| 26289 | AK5 | ATP + AMP <-> 2 ADP<br>GTP + AMP <-> ADP + GDP<br>ITP + AMP <-> ADP + IDP | 2.7.4.3 |
| 4830 | NME1, NM23, NM23-H1 | UDP + ATP <-> UTP + ADP<br>CDP + ATP <-> CTP + ADP<br>GDP + ATP <-> GTP + ADP<br>IDP + ATP <-> ITP + IDP | 2.7.4.6 |

TABLE 1-continued

| Locus ID | Gene Ab. | Reaction Stoichiometry | E.C. |
|---|---|---|---|
| | | DGDP + ATP <-> DGTP + ADP | |
| | | DUDP + ATP <-> DUTP + ADP | |
| | | DCDP + ATP <-> DCTP + ADP | |
| | | DTDP + ATP <-> DTTP + ADP | |
| | | DADP + ATP <-> DATP + ADP | |
| 4831 | NME2, NM23-H2 | UDP + ATP <-> UTP + ADP | 2.7.4.6 |
| | | CDP + ATP <-> CTP + ADP | |
| | | GDP + ATP <-> GTP + ADP | |
| | | IDP + ATP <-> ITP + IDP | |
| | | DGDP + ATP <-> DGTP + ADP | |
| | | DUDP + ATP <-> DUTP + ADP | |
| | | DCDP + ATP <-> DCTP + ADP | |
| | | DTDP + ATP <-> DTTP + ADP | |
| | | DADP + ATP <-> DATP + ADP | |
| 4832 | NME3, DR-nm23, DR-NM23 | UDP + ATP <-> UTP + ADP | 2.7.4.6 |
| | | CDP + ATP <-> CTP + ADP | |
| | | GDP + ATP <-> GTP + ADP | |
| | | IDP + ATP <-> ITP + IDP | |
| | | DGDP + ATP <-> DGTP + ADP | |
| | | DUDP + ATP <-> DUTP + ADP | |
| | | DCDP + ATP <-> DCTP + ADP | |
| | | DTDP + ATP <-> DTTP + ADP | |
| | | DADP + ATP <-> DATP + ADP | |
| 4833 | NME4 | UDPm + ATPm <-> UTPm + ADPm | 2.7.4.6 |
| | | CDPm + ATPm <-> CTPm + ADPm | |
| | | GDPm + ATPm <-> GTPm + ADPm | |
| | | IDPm + ATPm <-> ITPm + IDPm | |
| | | DGDPm + ATPm <-> DGTPm + ADPm | |
| | | DUDPm + ATPm <-> DUTPm + ADPm | |
| | | DCDPm + ATPm <-> DCTPm + ADPm | |
| | | DTDPm + ATPm <-> DTTPm + ADPm | |
| | | DADPm + ATPm <-> DATPm + ADPm | |
| 22978 | NT5B, PNT5, NT5B-PENDING | AMP + H2O -> PI + ADN | 3.1.3.5 |
| | | GMP -> PI + GSN | |
| | | CMP -> CYTD + PI | |
| | | UMP -> PI + URI | |
| | | IMP -> PI + INS | |
| | | DUMP -> DU + PI | |
| | | DTMP -> DT + PI | |
| | | DAMP -> DA + PI | |
| | | DGMP -> DG + PI | |
| | | DCMP -> DC + PI | |
| | | XMP -> PI + XTSINE | |
| 4877 | NT3 | AMP -> PI + ADN | 3.1.3.5 |
| | | GMP -> PI + GSN | |
| | | CMP -> CYTD + PI | |
| | | UMP -> PI + URI | |
| | | IMP -> PI + INS | |
| | | DUMP -> DU + PI | |
| | | DTMP -> DT + PI | |
| | | DAMP -> DA + PI | |
| | | DGMP -> DG + PI | |
| | | DCMP -> DC + PI | |
| | | XMP -> PI + XTSINE | |
| 4907 | NT5, CD73 | AMP -> PI + ADN | 3.1.3.5 |
| | | GMP -> PI + GSN | |
| | | CMP -> CYTD + PI | |
| | | UMP -> PI + URI | |
| | | IMP -> PI + INS | |
| | | DUMP -> DU + PI | |
| | | DTMP -> DT + PI | |
| | | DAMP -> DA + PI | |
| | | DGMP -> DG + PI | |
| | | DCMP -> DC + PI | |
| | | XMP -> PI + XTSINE | |
| 7370 | UMPH2 | AMP -> PI + ADN | 3.1.3.5 |
| | | GMP -> PI + GSN | |
| | | CMP -> CYTD + PI | |
| | | UMP -> PI + URI | |
| | | IMP -> PI + INS | |
| | | DUMP -> DU + PI | |
| | | DTMP -> DT + PI | |
| | | DAMP -> DA + PI | |
| | | DGMP -> DG + PI | |
| | | DCMP -> DC + PI | |
| | | XMP -> PI + XTSINE | |
| 10846 | PDE10A | cAMP -> AMP | 3.1.4.17 |

TABLE 1-continued

| Locus ID | Gene Ab. | Reaction Stoichiometry | E.C. |
|---|---|---|---|
| | | cAMP -> AMP | |
| | | cdAMP -> dAMP | |
| | | cIMP -> IMP | |
| | | cGMP -> GMP | |
| | | cCMP -> CMP | |
| 27115 | PDE7B | cAMP -> AMP | 3.1.4.17 |
| | | cAMP -> AMP | |
| | | cdAMP -> dAMP | |
| | | cIMP -> IMP | |
| | | cGMP -> GMP | |
| | | cCMP -> CMP | |
| 5136 | PDE1A | cAMP -> AMP | 3.1.4.17 |
| | | cAMP -> AMP | |
| | | cdAMP -> dAMP | |
| | | cIMP -> IMP | |
| | | cGMP -> GMP | |
| | | cCMP -> CMP | |
| 5137 | PDE1C, HCAM3 | cAMP -> AMP | 3.1.4.17 |
| | | cAMP -> AMP | |
| | | cdAMP -> dAMP | |
| | | cIMP -> IMP | |
| | | cGMP -> GMP | |
| | | cCMP -> CMP | |
| 5138 | PDE2A | cAMP -> AMP | 3.1.4.17 |
| | | cAMP -> AMP | |
| | | cdAMP -> dAMP | |
| | | cIMP -> IMP | |
| | | cGMP -> GMP | |
| | | cCMP -> CMP | |
| 5139 | PDE3A, CGI-PDE | cAMP -> AMP | 3.1.4.17 |
| | | cAMP -> AMP | |
| | | cdAMP -> dAMP | |
| | | cIMP -> IMP | |
| | | cGMP -> GMP | |
| | | cCMP -> CMP | |
| 5140 | PDE3B | cAMP -> AMP | 3.1.4.17 |
| | | cAMP -> AMP | |
| | | cdAMP -> dAMP | |
| | | cIMP -> IMP | |
| | | cGMP -> GMP | |
| | | cCMP -> CMP | |
| 5141 | PDE4A, DPDE2 | cAMP -> AMP | 3.1.4.17 |
| 5142 | PDE4B, DPDE4, PDEIVB | cAMP -> AMP | 3.1.4.17 |
| 5143 | PDE4C, DPDE1 | cAMP -> AMP | 3.1.4.17 |
| 5144 | PDE4D, DPDE3 | cAMP -> AMP | 3.1.4.17 |
| 5145 | PDE6A, PDEA, CGPR-A | cGMP -> GMP | 3.1.4.17 |
| 5146 | PDE6C, PDEA2 | cGMP -> GMP | 3.1.4.17 |
| 5147 | PDE6D | cGMP -> GMP | 3.1.4.17 |
| 5148 | PDE6G, PDEG | cGMP -> GMP | 3.1.4.17 |
| 5149 | PDE6H | cGMP -> GMP | 3.1.4.17 |
| 5152 | PDE9A | cAMP -> AMP | 3.1.4.17 |
| | | cAMP -> AMP | |
| | | cdAMP -> dAMP | |
| | | cIMP -> IMP | |
| | | cGMP -> GMP | |
| | | cCMP -> CMP | |
| 5153 | PDES1B | cAMP -> AMP | 3.1.4.17 |
| | | cAMP -> AMP | |
| | | cdAMP -> dAMP | |
| | | cIMP -> IMP | |
| | | cGMP -> GMP | |
| | | cCMP -> CMP | |
| 5158 | PDE6B, CSNB3, PDEB | cGMP -> GMP | 3.1.4.17 |
| 8654 | PDE5A | cGMP -> GMP | 3.1.4.17 |
| 100 | ADA | ADN -> INS + NH3 | 3.5.4.4 |
| | | DA -> DIN + NH3 | |
| 270 | AMPD1, MADA | AMP -> IMP + NH3 | 3.5.4.6 |
| 271 | AMPD2 | AMP -> IMP + NH3 | 3.5.4.6 |
| 272 | AMPD3 | AMP -> IMP + NH3 | 3.5.4.6 |
| 953 | ENTPD1, CD39 | | 3.6.1.5 |
| 3704 | ITPA | | 3.6.1.19 |
| 107 | ADCY1 | ATP -> cAMP + PPI | 4.6.1.1 |
| 108 | ADCY2, HBAC2 | ATP -> cAMP + PPI | 4.6.1.1 |
| 109 | ADCY3, AC3, KIAA0511 | ATP -> cAMP + PPI | 4.6.1.1 |
| 110 | ADCY4 | ATP -> cAMP + PPI | 4.6.1.1 |
| 111 | ADCY5 | ATP -> cAMP + PPI | 4.6.1.1 |
| 112 | ADCY6 | ATP -> cAMP + PPI | 4.6.1.1 |

TABLE 1-continued

| Locus ID | Gene Ab. | Reaction Stoichiometry | E.C. |
|---|---|---|---|
| 113 | ADCY7, KIAA0037 | ATP -> cAMP + PPI | 4.6.1.1 |
| 114 | ADCY8, ADCY3, HBAC1 | ATP -> cAMP + PPI | 4.6.1.1 |
| 115 | ADCY9 | ATP -> cAMP + PPI | 4.6.1.1 |
| 2977 | GUCY1A2, GUC1A2, GC-SA2 | | 4.6.1.2 |
| 2982 | GUCY1A3, GUC1A3, GUCSA3, GC-SA3 | | 4.6.1.2 |
| 2983 | GUCY1B3, GUC1B3, GUCSB3, GC-SB3 | | 4.6.1.2 |
| 2984 | GUCY2C, GUC2C, STAR | | 4.6.1.2 |
| 2986 | GUCY2F, GUC2F, GC-F, GUC2DL, RETGC-2 | | 4.6.1.2 |
| 3000 | GUCY2D, CORD6, GUC2D, LCA1, GUC1A4, LCA, retGC | | 4.6.1.2 |
| 4881 | NPR1, ANPRA, GUC2A, NPRA | | 4.6.1.2 |
| 4882 | NPR2, ANPRB, GUC2B, NPRB, NPRBi | | 4.6.1.2 |
| 159 | ADSS | IMP + GTP + ASP -> GDP + PI + ASUC | 6.3.4.4 |
| 318 | NUDT2, APAH1 | | 3.6.1.17 |
| 5167 | ENPP1, M6S1, NPPS, PCA1, PC-1, PDNP1 | | 3.6.1.9 |
| 5168 | ENPP2, ATX, PD-IALPHA, PDNP2 | | 3.6.1.9 |
| 5169 | ENPP3, PD-IBETA, PDNP3 | | 3.6.1.9 |
| | | | 3.1.4.1 |
| 2272 | FHIT | | 3.6.1.29 |

4.2 Pyrimidine metabolism PATH: hsa00240

| Locus ID | Gene Ab. | Reaction Stoichiometry | E.C. |
|---|---|---|---|
| 790 | CAD | GLN + 2 ATP + CO2 -> GLU + CAP + 2 ADP + PI | 6.3.5.5 |
| | | CAP + ASP -> CAASP + PI | 2.1.3.2 |
| | | CAASP <-> DOROA | 3.5.2.3 |
| 1723 | DHODH | DOROA + O2 <-> H2O2 + OROA | 1.3.3.1 |
| 7372 | UMPS, OPRT | OMP -> CO2 + UMP | 4.1.1.23 |
| | | OROA + PRPP <-> PPI + OMP | 2.4.2.10 |
| 51727 | LOC51727 | ATP + UMP <-> ADP + UDP | 2.7.4.14 |
| | | CMP + ATP <-> ADP + CDP | |
| | | DCMP + ATP <-> ADP + DCDP | |
| 50808 | AKL3L | | 2.7.4.10 |
| 1503 | CTPS | UTP + GLN + ATP -> GLU + CTP + ADP + PI | 6.3.4.2 |
| | | ATP + UTP + NH3 -> ADP + PI + CTP | |
| 7371 | UMPK, TSA903 | URI + ATP -> ADP + UMP | 2.7.1.48 |
| | | URI + GTP -> UMP + GDP | |
| | | CYTD + GTP -> GDP + CMP | |
| 7378 | UP | URI + PI <-> URA + R1P | 2.4.2.3 |
| 1806 | DPYD, DPD | | 1.3.1.2 |
| 1807 | DPYS, DHPase, DHPASE, DHP | | 3.5.2.2 |
| 51733 | LOC51733 | | 3.5.1.6 |
| 7296 | TXNRD1, TXNR | OTHIO + NADPH -> NADP + RTHIO | 1.6.4.5 |
| 1854 | DUT | DUTP -> PPI + DUMP | 3.6.1.23 |
| 7298 | TYMS, TMS, TS | DUMP + METTHF -> DHF + DTMP | 2.1.1.45 |
| 978 | CDA, CDD | CYTD -> URI + NH3 | 3.5.4.5 |
| | | DC -> NH3 + DU | |
| 1635 | DCTD | DCMP <-> DUMP + NH3 | 3.5.4.12 |
| 7083 | TK1 | DU + ATP -> DUMP + ADP | 2.7.1.21 |
| | | DT + ATP -> ADP + DTMP | |
| 7084 | TK2 | DUm + ATPm -> DUMPm + ADPm | 2.7.1.21 |
| | | DTm + ATPm -> DTMPm + ADPm | |
| 1841 | DTYMK, TYMK, CDC8 | DTMP + ATP <-> ADP + DTDP | 2.7.4.9 |

4.3 Nucleotide sugars metabolism PATH: hsa00520

| Locus ID | Gene Ab. | Reaction Stoichiometry | E.C. |
|---|---|---|---|
| 23483 | TDPGD | | 4.2.1.46 |
| 1486 | CTBS, CTB | | 3.2.1.— |

5. Amino Acid Metabolism
5.1 Glutamate metabolism PATH: hsa00251

| Locus ID | Gene Ab. | Reaction Stoichiometry | E.C. |
|---|---|---|---|
| 8659 | ALDH4, P5CDH | P5C + NAD + H2O -> NADH + GLU | 1.5.1.12 |
| 2058 | EPRS, QARS, QPRS | GLU + ATP -> GTRNA + AMP + PPI | 6.1.1.17 |
| | | | 6.1.1.15 |
| 2673 | GFPT1, GFA, GFAT, GFPT | F6P + GLN -> GLU + GA6P | 2.6.1.16 |
| 9945 | GFPT2, GFAT2 | F6P + GLN -> GLU + GA6P | 2.6.1.16 |
| 5859 | QARS | | 6.1.1.18 |
| 2729 | GLCLC, GCS, GLCL | CYS + GLU + ATP -> GC + PI + ADP | 6.3.2.2 |
| 2730 | GLCLR | CYS + GLU + ATP -> GC + PI + ADP | 6.3.2.2 |
| 2937 | GSS, GSHS | GLY + GC + ATP -> RGT + PI + ADP | 6.3.2.3 |
| 2936 | GSR | NADPH + OGT -> NADP + RGT | 1.6.4.2 |
| 5188 | PET112L, PET112 | | 6.3.5.— |

5.2 Alanine and aspartate metabolism PATH: hsa00252

| Locus ID | Gene Ab. | Reaction Stoichiometry | E.C. |
|---|---|---|---|
| 4677 | NARS, ASNRS | ATP + ASP + TRNA -> AMP + PPI + ASPTRNA | 6.1.1.22 |

TABLE 1-continued

| Locus ID | Gene Ab. | Reaction Stoichiometry | E.C. |
|---|---|---|---|
| 435 | ASL | ARGSUCC -> FUM + ARG | 4.3.2.1 |
| 189 | AGXT, SPAT | SERm + PYRm <-> ALAm + 3HPm | 2.6.1.51 |
| | | ALA + GLX <-> PYR + GLY | 2.6.1.44 |
| 16 | AARS | | 6.1.1.7 |
| 1615 | DARS | | 6.1.1.12 |
| 445 | ASS, CTLN1, ASS1 | CITR + ASP + ATP <-> AMP + PPI + ARGSUCC | 6.3.4.5 |
| 443 | ASPA, ASP, ACY2 | | 3.5.1.15 |
| 1384 | CRAT, CAT1 | | 2.3.1.7 |
| | | ACCOA + CAR -> COA + ACAR | |
| 8528 | DDO | | 1.4.3.1 |

5.3 Glycine, serine and threonine metabolism PATH: hsa00260

| Locus ID | Gene Ab. | Reaction Stoichiometry | E.C. |
|---|---|---|---|
| 5723 | PSPH, PSP | 3PSER + H2O -> PI + SER | 3.1.3.3 |
| 29968 | PSA | PHP + GLU <-> AKG + 3PSER | 2.6.1.52 |
| | | OHB + GLU <-> PHT + AKG | |
| 26227 | PHGDH, SERA, PGDH, PGD, PGAD | 3PG + NAD <-> NADH + PHP | 1.1.1.95 |
| 23464 | GCAT, KBL | | 2.3.1.29 |
| 211 | ALAS1, ALAS | SUCCOA + GLY -> ALAV + COA + CO2 | 2.3.1.37 |
| 212 | ALAS2, ANH1, ASB | SUCCOA + GLY -> ALAV + COA + CO2 | 2.3.1.37 |
| 4128 | MAOA | AMA + H2O + FAD -> NH3 + FADH2 + MTHGXL | 1.4.3.4 |
| 4129 | MAOB | AMA + H2O + FAD -> NH3 + FADH2 + MTHGXL | 1.4.3.4 |
| 26 | ABP1, AOC1, DAO | | 1.4.3.6 |
| 314 | AOC2, DAO2, RAO | | 1.4.3.6 |
| 8639 | AOC3, VAP-1, VAP1, HPAO | | 1.4.3.6 |
| 2731 | GLDC | GLY + LIPO <-> SAP + CO2 | 1.4.4.2 |
| 1610 | DAO, DAMOX | | 1.4.3.3 |
| 2617 | GARS | | 6.1.1.14 |
| 2628 | GATM | | 2.1.4.1 |
| 2593 | GAMT | | 2.1.1.2 |
| 23761 | PISD, PSSC, DKFZP566G2246, DJ858B16 | PS -> PE + CO2 | 4.1.1.65 |
| 635 | BHMT | | 2.1.1.5 |
| 29958 | DMGDH | | 1.5.99.2 |
| 875 | CBS | SER + HCYS -> LLCT + H2O | 4.2.1.22 |
| 6301 | SARS, SERS | | 6.1.1.11 |
| 10993 | SDS, SDH | SER -> PYR + NH3 + H2O | 4.2.1.13 |
| 6897 | TARS | | 6.1.1.3 |

5.4 Methionine metabolism PATH: hsa00271

| Locus ID | Gene Ab. | Reaction Stoichiometry | E.C. |
|---|---|---|---|
| 4143 | MAT1A, MATA1, SAMS1, MAT, SAMS | MET + ATP + H2O -> PPI + PI + SAM | 2.5.1.6 |
| 4144 | MAT2A, MATA2, SAMS2, MATII | MET + ATP + H2O -> PPI + PI + SAM | 2.5.1.6 |
| 1786 | DNMT1, MCMT, DNMT | SAM + DNA-> SAH + DNA5MC | 2.1.1.37 |
| 10768 | AHCYL1, XPVKONA | SAH + H2O -> HCYS + ADN | 3.3.1.1 |
| 191 | AHCY, SAHH | SAH + H2O -> HCYS + ADN | 3.3.1.1 |
| 4141 | MARS, METRS, MTRNS | | 6.1.1.10 |
| 4548 | MTR | HCYS + MTHF -> THF + MET | 2.1.1.13 |

5.5 Cysteine metabolism PATH: hsa00272

| Locus ID | Gene Ab. | Reaction Stoichiometry | E.C. |
|---|---|---|---|
| 833 | CARS | | 6.1.1.16 |
| 1036 | CDO1 | CYS + O2 <-> CYSS | 1.13.11.20 |
| 8509 | NDST2, HSST2, NST2 | | 2.8.2.— |

5.6 Valine, leucine and isoleucine degradation PATH: hsa00280

| Locus ID | Gene Ab. | Reaction Stoichiometry | E.C. |
|---|---|---|---|
| 586 | BCAT1, BCT1, ECA39, MECA39 | AKG + ILE -> OMVAL + GLU | 2.6.1.42 |
| | | AKG + VAL -> OIVAL + GLU | |
| | | AKG + LEU -> OICAP + GLU | |
| 587 | BCAT2, BCT2 | OICAPm + GLUm <-> AKGm + LEUm | 2.6.1.42 |
| | | OMVALm + GLUm <-> AKGm + ILEm | |
| 5014 | OVD1A | | 1.2.4.4 |
| 593 | BCKDHA, MSUD1 | OMVALm + COAm + NADm -> MBCOAm + NADHm + CO2m | 1.2.4.4 |
| | | OIVALm + COAm + NADm -> IBCOAm + NADHm + CO2m | |
| | | OICAPm + COAm + NADm -> IVOCAm + NADHm + CO2m | |
| 594 | BCKDHB, E1B | OMVALm + COAm + NADm -> MBCOAm + NADHm + CO2m | 1.2.4.4 |
| | | OIVALm + COAm + NADm -> IBCOAm + NADHm + CO2m | |
| | | OICAPm + COAm + NADH -> IVCOAm + NADHm + CO2m | |
| 3712 | IVD | IVCOAm + FADm -> MCRCOAm + FADH2m | 1.3.99.10 |
| 316 | AOX1, AO | | 1.2.3.1 |
| 4164 | MCCC1 | MCRCOAm + ATPm + CO2m + H2Om -> MGCOAm + ADPm + Pim | 6.4.1.4 |
| 4165 | MCCC2 | MCRCOAm + ATPm + CO2m + H2Om -> MGCOAm + ADPm + Pim | 6.4.1.4 |

5.7 Valine, leucine and isoleucine biosynthesis PATH: hsa00290

| Locus ID | Gene Ab. | Reaction Stoichiometry | E.C. |
|---|---|---|---|
| 23395 | KIAA0028, LARS2 | | 6.4.1.4 |
| 3926 | LARS | | 6.4.1.4 |
| 3376 | IARS, ILRS | | 6.1.1.5 |
| 7406 | VARS1, VARS | | 6.1.1.9 |

TABLE 1-continued

| Locus ID | Gene Ab. | Reaction Stoichiometry | E.C. |
|---|---|---|---|
| 7407 | VARS2, G7A | | 6.1.1.9 |
| 5.8 Lysine biosynthesis PATH: hsa00300 | | | |
| 3735 | KARS, KIAA0070 | ATP + LYS + LTRNA -> AMP + PPI + LLTRNA | 6.1.1.6 |
| 5.9 Lysine degradation PATH: hsa00310 | | | |
| 8424 | BBOX, BBH, GAMMA-BBH, G-BBH | | 1.14.11.1 |
| 5351 | PLOD, LLH | | 1.14.11.4 |
| 5352 | PLOD2 | | 1.14.11.4 |
| 8985 | PLOD3, LH3 | | 1.14.11.4 |
| 10157 | LKR/SDH, AASS | LYS + NADPH + AKG -> NADP + H2O + SAC | 1.5.1.9 |
| | | SAC + H2O + NAD -> GLU + NADH + AASA | |
| 5.10 Arginine and proline metabolism PATH: hsa00330 | | | |
| 5009 | OTC | ORNm + CAPm -> CITRm + Pim + Hm | 2.1.3.3 |
| 383 | ARG1 | ARG -> ORN + UREA | 3.5.3.1 |
| 384 | ARG2 | ARG -> ORN + UREA | 3.5.3.1 |
| 4842 | NOS1, NOS | | 1.14.13.39 |
| 4843 | NOS2A, NOS2 | | 1.14.13.39 |
| 4846 | NOS3, ECNOS | | 1.14.13.39 |
| 4942 | OAT | ORN + AKG <-> GLUGSAL + GLU | 2.6.1.13 |
| 5831 | PYCR1, P5C, PYCR | P5C + NADPH -> PRO + NADP | 1.5.1.2 |
| | | P5C + NADH -> PRO + NAD | |
| | | PHC + NADPH -> HPRO + NADP | |
| | | PHC + NADH -> HPRO + NAD | |
| 5033 | P4HA1, P4HA | | 1.14.11.2 |
| 5917 | RARS | ATP + ARG + ATRNA -> AMP + PPI + ALTRNA | 6.1.1.19 |
| 1152 | CKB, CKBB | PCRE + ADP -> CRE + ATP | 2.7.3.2 |
| 1156 | CKBE | | 2.7.3.2 |
| 1158 | CKM, CKMM | | 2.7.3.2 |
| 1159 | CKMT1, CKMT, UMTCK | | 2.7.3.2 |
| 1160 | CKMT2, SMTCK | | 2.7.3.2 |
| 6723 | SRM, SPS1, SRML1 | PTRSC + SAM -> SPRMD + 5MTA | 2.5.1.16 |
| 262 | AMD1, ADOMETDC | SAM <-> DSAM + CO2 | 4.1.1.50 |
| 263 | AMDP1, AMD, AMD2 | SAM <-> DSAM + CO2 | 4.1.1.50 |
| 1725 | DHPS | SPRMD + Qm -> DAPRP + QH2m | 1.5.99.6 |
| 6611 | SMS | DSAM + SPRMD -> 5MTA + SPRM | 2.5.1.22 |
| 4953 | ODC1 | ORN -> PTRSC + CO2 | 4.1.1.17 |
| 6303 | SAT, SSAT | | 2.3.1.57 |
| 5.11 Histidine metabolism PATH: hsa00340 | | | |
| 10841 | FTCD | FIGLU + THF -> NFTHF + GLU | 2.1.2.5 |
| | | | 4.3.1.4 |
| 3067 | HDC | | 4.1.1.22 |
| 1644 | DDC, AADC | | 4.1.1.28 |
| 3176 | HNMT | | 2.1.1.8 |
| 218 | ALDH3 | ACAL + NAD -> NADH + AC | 1.2.1.5 |
| 220 | ALDH6 | ACAL + NAD -> NADH + AC | 1.2.1.5 |
| 221 | ALDH7, ALDH4 | ACAL + NAD -> NADH + AC | 1.2.1.5 |
| 222 | ALDH8 | ACAL + NAD -> NADH + AC | 1.2.1.5 |
| 3035 | HARS | ATP + HIS + HTRNA -> AMP + PPI + HHTRNA | 6.1.1.21 |
| 5.12 Tyrosine metabolism PATH: hsa00350 | | | |
| 6898 | TAT | AKG + TYR -> HPHPYR + GLU | 2.6.1.5 |
| 3242 | HPD, PPD | HPHPYR + O2 -> HGTS + CO2 | 1.13.11.27 |
| 3081 | HGD, AKU, HGO | HGTS + O2 -> MACA | 1.13.11.5 |
| 2954 | GSTZ1, MAAI | MACA -> FACA | 5.2.1.2 |
| | | | 2.5.1.18 |
| 2184 | FAH | FACA + H2O -> FUM + ACA | 3.7.1.2 |
| 7299 | TYR, OCAIA | | 1.14.18.1 |
| 7054 | TH, TYH | | 1.14.16.2 |
| 1621 | DBH | | 1.14.17.1 |
| 5409 | PNMT, PENT | | 2.1.1.28 |
| 1312 | COMT | | 2.1.1.6 |
| 7173 | TPO, TPX | | 1.11.1.8 |
| 5.13 Phenylalanine metabolism PATH: hsa00360 | | | |
| 501 | ATQ1 | | 1.2.1.— |
| 5.14 Tryptophan metabolism PATH: hsa00380 | | | |
| 6999 | TDO2, TPH2, TRPO, TDO | TRP + O2 -> FKYN | 1.13.11.11 |
| 8564 | KMO | KYN + NADPH + O2 -> HKYN + NADP + H2O | 1.14.13.9 |
| 8942 | KYNU | KYN -> ALA + AN | 3.7.1.3 |
| | | HKYN + H2O -> HAN + ALA | |
| 23498 | HAAO, HAO, 3-HAO | HAN + O2 -> CMUSA | 1.13.11.6 |
| 7166 | TPH, TPRH | | 1.14.16.4 |
| 438 | ASMT, HIOMT, ASMTY | | 2.1.1.4 |

TABLE 1-continued

| Locus ID | Gene Ab. | Reaction Stoichiometry | E.C. |
|---|---|---|---|
| 15 | AANAT, SNAT | | 2.3.1.87 |
| 3620 | INDO, IDO | | 1.13.11.42 |
| 10352 | WARS2 | ATPm + TRPm + TRNAm -> AMPm + PPIm + TRPTRNAm | 6.1.1.2 |
| 7453 | WARS, IFP53, IFI53, GAMMA-2 | ATP + TRP + TRNA -> AMP + PPI + TRPTRNA | 6.1.1.2 |
| 4734 | NEDD4, KIAA0093 | | 6.3.2.— |

5.15 Phenylalanine, tyrosine and tryptophan biosynthesis PATH: hsa00400

| Locus ID | Gene Ab. | Reaction Stoichiometry | E.C. |
|---|---|---|---|
| 5053 | PAH, PKU1 | PHE + THBP + O2 -> TYR + DHBP + H2O | 1.14.16.1 |
| 10667 | FARS1 | | 6.1.1.20 |
| 2193 | FARSL, CML33 | | 6.1.1.20 |
| 10056 | PheHB | | 6.1.1.20 |
| 8565 | YARS, TYRRS, YTS, YRS | | 6.1.1.1 |

5.16 Urea cycle and metabolism of amino groups PATH: hsa00220

| Locus ID | Gene Ab. | Reaction Stoichiometry | E.C. |
|---|---|---|---|
| 5832 | PYCS | GLUP + NADH -> NAD + PI + GLUGSAL | 2.7.2.11 |
| | | GLUP + NADPH -> NADP + PI + GLUGSAL | 1.2.1.41 |
| 95 | ACY1 | | 3.5.1.14 |

6. Metabolism of Other Amino Acids
6.1 beta-Alanine metabolism PATH: hsa00410
6.2 Taurine and hypotaurine metabolism PATH: hsa00430

| Locus ID | Gene Ab. | Reaction Stoichiometry | E.C. |
|---|---|---|---|
| 2678 | GGT1, GTG, D22S672, D22S732, GGT | RGT + ALA -> CGLY + ALAGLY | 2.3.2.2 |
| 2679 | GGT2, GGT | RGT + ALA -> CGLY + ALAGLY | 2.3.2.2 |
| 2680 | GGT3 | RGT + ALA -> CGLY + ALAGLY | 2.3.2.2 |
| 2687 | GGTLA1, GGT-REL, DKFZP566O011 | RGT + ALA -> CGLY + ALAGLY | 2.3.2.2 |

6.3 Aminophosphonate metabolism PATH: hsa00440

| Locus ID | Gene Ab. | Reaction Stoichiometry | E.C. |
|---|---|---|---|
| 5130 | PCYT1A, CTPCT, CT, PCYT1 | PCHO + CTP -> CDPCHO + PPI | 2.7.7.15 |
| 9791 | PTDSS1, KIAA0024, PSSA | CDPDG + SER <-> CMP + PS | 2.7.8.— |

6.4 Selenoamino acid metabolism PATH: hsa00450

| Locus ID | Gene Ab. | Reaction Stoichiometry | E.C. |
|---|---|---|---|
| 22928 | SPS2 | | 2.7.9.3 |
| 22929 | SPS, SELD | | 2.7.9.3 |

6.5 Cyanoamino acid metabolism PATH: hsa00460
6.6 D-Glutamine and D-glutamate metabolism PATH: hsa00471
6.7 D-Arginine and D-ornithine metabolism PATH: hsa00472
6.9 Glutathione metabolism PATH: hsa00480

| Locus ID | Gene Ab. | Reaction Stoichiometry | E.C. |
|---|---|---|---|
| 5182 | PEPB | | 3.4.11.4 |
| 2655 | GCTG | | 2.3.2.4 |
| 2876 | GPX1, GSHPX1 | 2 RGT + H2O2 <-> OGT | 1.11.1.9 |
| 2877 | GPX2, GSHPX-GI | 2 RGT + H2O2 <-> OGT | 1.11.1.9 |
| 2878 | GPX3 | 2 RGT + H2O2 <-> OGT | 1.11.1.9 |
| 2879 | GPX4 | 2 RGT + H2O2 <-> OGT | 1.11.1.9 |
| 2880 | GPX5 | 2 RGT + H2O2 <-> OGT | 1.11.1.9 |
| 2881 | GPX6 | 2 RGT + H2O2 <-> OGT | 1.11.1.9 |
| 2938 | GSTA1 | | 2.5.1.18 |
| 2939 | GSTA2, GST2 | | 2.5.1.18 |
| 2940 | GSTA3 | | 2.5.1.18 |
| 2941 | GSTA4 | | 2.5.1.18 |
| 2944 | GSTM1, GST1, MU | | 2.5.1.18 |
| 2946 | GSTM2, GST4 | | 2.5.1.18 |
| 2947 | GSTM3, GST5 | | 2.5.1.18 |
| 2948 | GSTM4 | | 2.5.1.18 |
| 2949 | GSTM5 | | 2.5.1.18 |
| 2950 | GSTP1, FAEES3, DFN7, GST3, PI | | 2.5.1.18 |
| 2952 | GSTT1 | | 2.5.1.18 |
| 2953 | GSTT2 | | 2.5.1.18 |
| 4257 | MGST1, GST12, MGST, MGST-I | | 2.5.1.18 |
| 4258 | MGST2, GST2, MGST-II | | 2.5.1.18 |
| 4259 | MGST3, GST-III | | 2.5.1.18 |

7. Metabolism of Complex Carbohydrates
7.1 Starch and sucrose metabolism PATH: hsa00500

| Locus ID | Gene Ab. | Reaction Stoichiometry | E.C. |
|---|---|---|---|
| 6476 | SI | | 3.2.1.10 |
| | | | 3.2.1.48 |
| 11181 | TREH, TRE, TREA | TRE -> 2 GLC | 3.2.1.28 |
| 2990 | GUSB | | 3.2.1.31 |
| 2632 | GBE1 | GLYCOGEN + PI -> G1P | 2.4.1.18 |
| 5834 | PYGB | GLYCOGEN + PI -> G1P | 2.4.1.1 |
| 5836 | PYGL | GLYCOGEN + PI -> G1P | 2.4.1.1 |
| 5837 | PYGM | GLYCOGEN + PI -> G1P | 2.4.1.1 |
| 2997 | GYS1, GYS | UDPG -> UDP + GLYCOGEN | 2.4.1.11 |
| 2998 | GYS2 | UDPG -> UDP + GLYCOGEN | 2.4.1.11 |
| 276 | AMY1A, AMY1 | | 3.2.1.1 |
| 277 | AMY1B, AMY1 | | 3.2.1.1 |

TABLE 1-continued

| Locus ID | Gene Ab. | Reaction Stoichiometry | E.C. |
|---|---|---|---|
| 278 | AMY1C, AMY1 | | 3.2.1.1 |
| 279 | AMY2A, AMY2 | | 3.2.1.1 |
| 280 | AMY2B, AMY2 | | 3.2.1.1 |
| 178 | AGL, GDE | | 2.4.1.25 |
| | | | 3.2.1.33 |
| 10000 | AKT3, PKBG, RAC-GAMMA, PRKBG | | 2.7.1.— |
| 1017 | CDK2 | | 2.7.1.— |
| 1018 | CDK3 | | 2.7.1.— |
| 1019 | CDK4, PSK-J3 | | 2.7.1.— |
| 1020 | CDK5, PSSALRE | | 2.7.1.— |
| 1021 | CDK6, PLSTIRE | | 2.7.1.— |
| 1022 | CDK7, CAK1, STK1, CDKN7 | | 2.7.1.— |
| 1024 | CDK8, K35 | | 2.7.1.— |
| 1025 | CDK9, PITALRE, CDC2L4 | | 2.7.1.— |
| 10298 | PAK4 | | 2.7.1.— |
| 10746 | MAP3K2, MEKK2 | | 2.7.1.— |
| 1111 | CHEK1, CHK1 | | 2.7.1.— |
| 11200 | RAD53, CHK2, CDS1, HUCDS1 | | 2.7.1.— |
| 1195 | CLK1, CLK | | 2.7.1.— |
| 1326 | MAP3K8, COT, EST, ESTF, TPL-2 | | 2.7.1.— |
| 1432 | MAPK14, CSBP2, CSPB1, PRKM14, PRKM15, CSBP1, P38, MXI2 | | 2.7.1.— |
| 1452 | CSNK1A1 | | 2.7.1.— |
| 1453 | CSNK1D, HCKID | | 2.7.1.— |
| 1454 | CSNK1E, HCKIE | | 2.7.1.— |
| 1455 | CSNK1G2 | | 2.7.1.— |
| 1456 | CSNK1G3 | | 2.7.1.— |
| 1612 | DAPK1, DAPK | | 2.7.1.— |
| 1760 | DMPK, DM, DMK, DM1 | | 2.7.1.— |
| 1859 | DYRK1A, DYRK1, DYRK, MNB, MNBH | | 2.7.1.— |
| 208 | AKT2, RAG-BETA, PRKBB, PKBBETA | | 2.7.1.— |
| 269 | AMHR2, AMHR | | 2.7.1.— |
| 27330 | RPS6KA6, RSK4 | | 2.7.1.— |
| 2868 | GPRK2L, GPRK4 | | 2.7.1.— |
| 2869 | GPRK5, GRK5 | | 2.7.1.— |
| 2870 | GPRK6, GRK6 | | 2.7.1.— |
| 29904 | HSU93850 | | 2.7.1.— |
| 30811 | HUNK | | 2.7.1.— |
| 3611 | ILK, P59 | | 2.7.1.— |
| 3654 | IRAK1, IRAK | | 2.7.1.— |
| 369 | ARAF1, PKS2, RAFA1 | | 2.7.1.— |
| 370 | ARAF2P, PKS1, ARAF2 | | 2.7.1.— |
| 3984 | LIMK1, LIMK | | 2.7.1.— |
| 3985 | LIMK2 | | 2.7.1.— |
| 4117 | MAK | | 2.7.1.— |
| 4140 | MARK3, KP78 | | 2.7.1.— |
| 4215 | MAP3K3, MAPKKK3, MEKK3 | | 2.7.1.— |
| 4216 | MAP3K4, MAPKKK4, MTK1, MEKK4, KIAA0213 | | 2.7.1.— |
| 4217 | MAP3K5, ASK1, MAPKKK5, MEKK5 | | 2.7.1.— |
| 4293 | MAP3K9, PRKE1, MLK1 | | 2.7.1.— |
| 4294 | MAP3K10, MLK2, MST | | 2.7.1.— |
| 4342 | MOS | | 2.7.1.— |
| 4751 | NEK2, NLK1 | | 2.7.1.— |
| 4752 | NEK3 | | 2.7.1.— |
| 5058 | PAK1, PAKalpha | | 2.7.1.— |
| 5062 | PAK2, PAK65, PAKgamma | | 2.7.1.— |
| 5063 | PAK3, MRX30, PAK3beta | | 2.7.1.— |
| 5127 | PCTK1, PCTGAIRE | | 2.7.1.— |
| 5128 | PCTK2 | | 2.7.1.— |
| 5129 | PCTK3, PCTAIRE | | 2.7.1.— |
| 5292 | PIM1, PIM | | 2.7.1.— |
| 5347 | PLK, PLK1 | | 2.7.1.— |
| 5562 | PRKAA1 | | 2.7.1.— |
| 5563 | PRKAA2, AMPK, PRKAA | | 2.7.1.— |
| 5578 | PRKCA, PKCA | | 2.7.1.— |
| 5579 | PRKCB1, PKCB, PRKCB, PRKCB2 | | 2.7.1.— |
| 5580 | PRKCD | | 2.7.1.— |
| 5581 | PRKCE | | 2.7.1.— |
| 5582 | PRKCG, PKCC, PKCG | | 2.7.1.— |
| 5583 | PRKCH, PKC-L, PRKCL | | 2.7.1.— |
| 5584 | PRKCI, DXS1179E, PKCI | | 2.7.1.— |
| 5585 | PRKCL1, PAK1, PRK1, DBK, PKN | | 2.7.1.— |
| 5586 | PRKCL2, PRK2 | | 2.7.1.— |
| 5588 | PRKCQ | | 2.7.1.— |
| 5590 | PRKCZ | | 2.7.1.— |

TABLE 1-continued

| Locus ID | Gene Ab. | Reaction Stoichiometry | E.C. |
|---|---|---|---|
| 5594 | MAPK1, PRKM1, P41MAPK, P42MAPK, ERK2, ERK, MAPK2, PRKM2 | | 2.7.1.— |
| 5595 | MAPK3, ERK1, PRKM3, P44ERK1, P44MAPK | | 2.7.1.— |
| 5597 | MAPK6, PRKM6, P97MAPK, ERK3 | | 2.7.1.— |
| 5598 | MAPK7, BMK1, ERK5, PRKM7 | | 2.7.1.— |
| 5599 | MAPK8, JNK, JNK1, SAPK1, PRKM8, JNK1A2 | | 2.7.1.— |
| 5601 | MAPK9, JNK2, PRKM9, P54ASAPK, JUNKINASE | | 2.7.1.— |
| 5602 | MAPK10, JNK3, PRKM10, P493F12, P54BSAPK | | 2.7.1.— |
| 5603 | MAPK13, SAPK4, PRKM13, P38DELTA | | 2.7.1.— |
| 5604 | MAP2K1, MAPKK1, MEK1, MKK1, PRKMK1 | | 2.7.1.— |
| 5605 | MAP2K2, MEK2, PRKMK2 | | 2.7.1.— |
| 5606 | MAP2K3, MEK3, MKK3, PRKMK3 | | 2.7.1.— |
| 5607 | MAP2K5, MEK5, PRKMK5 | | 2.7.1.— |
| 5608 | MAP2K6, MEK6, MKK6, SAPKK3, PRKMK6 | | 2.7.1.— |
| 5609 | MAP2K7, MAPKK7, MKK7, PRKMK7, JNKK2 | | 2.7.1.— |
| 5610 | PRKR, EIF2AK1, PKR | | 2.7.1.— |
| 5613 | PRKX, PKX1 | | 2.7.1.— |
| 5894 | RAF1 | | 2.7.1.— |
| 613 | BCR, CML, PHL, BCR1, D22S11, D22S662 | | 2.7.1.— |
| 6195 | RPS6KA1, HU-1, RSK, RSK1, MAPKAPK1A | | 2.7.1.— |
| 6196 | RPS6KA2, HU-2, MAPKAPK1C, RSK, RSK3 | | 2.7.1.— |
| 6197 | RPS6KA3, RSK2, HU-2, HU-3, RSK, MAPKAPK1B, ISPK-1 | | 2.7.1.— |
| 6198 | RPS6KB1, STK14A | | 2.7.1.— |
| 6199 | RPS6KB2, P70-BETA, P70S6KB | | 2.7.1.— |
| 6300 | MAPK12, ERK6, PRKM12, SAPK3, P38GAMMA, SAPK-3 | | 2.7.1.— |
| 6416 | MAP2K4, JNKK1, MEK4, PRKMK4, SERK1, MKK4 | | 2.7.1.— |
| 6446 | SGK | | 2.7.1.— |
| 658 | BMPR1B, ALK-6, ALK6 | | 2.7.1.— |
| 659 | BMPR2, BMPR-II, BMPR3, BRK-3 | | 2.7.1.— |
| 673 | BRAF | | 2.7.1.— |
| 6792 | STK9 | | 2.7.1.— |
| 6794 | STK11, LKB1, PJS | | 2.7.1.— |
| 6885 | MAP3K7, TAK1 | | 2.7.1.— |
| 699 | BUB1 | | 2.7.1.— |
| 701 | BUB1B, BUBR1, MAD3L | | 2.7.1.— |
| 7016 | TESK1 | | 2.7.1.— |
| 7272 | TTK, MPS1L1 | | 2.7.1.— |
| 7867 | MAPKAPK3, 3PK, MAPKAP3 | | 2.7.1.— |
| 8408 | ULK1 | | 2.7.1.— |
| 8558 | CDK10, PISSLRE | | 2.7.1.— |
| 8621 | CDC2L5, CDC2L, CHED | | 2.7.1.— |
| 8737 | RIPK1, RIP | | 2.7.1.— |
| 8814 | CDKL1, KKIALRE | | 2.7.1.— |
| 8899 | PRP4, PR4H | | 2.7.1.— |
| 9064 | MAP3K6, MAPKKK6 | | 2.7.1.— |
| 9149 | DYRK1B | | 2.7.1.— |
| 92 | ACVR2, ACTRII | | 2.7.1.— |
| 9201 | DCAMKL1, KIAA0369 | | 2.7.1.— |
| 93 | ACVR2B | | 2.7.1.— |
| 983 | CDC2 | | 2.7.1.— |
| 984 | CDC2L1 | | 2.7.1.— |
| 5205 | FIC1, BRIC, PFIC1, PFIC, ATP8B1 | DHPP -> DHP + PI<br>GTP -> GSN + 3 PI<br>DGTP -> DG + 3 PI | 3.6.1.— |

7.2 Glycoprotein biosynthesis PATH: hsa00510

| Locus ID | Gene Ab. | Reaction Stoichiometry | E.C. |
|---|---|---|---|
| 1798 | DPAGT1, DPAGT, UGAT, UAGT, D11S366, DGPT, DPAGT2, GPT | | 2.7.8.15 |
| 29880 | ALG5 | | 2.4.1.117 |
| 8813 | DPM1 | GDPMAN + DOLP -> GDP + DOLMANP | 2.4.1.83 |
| 1650 | DDOST, OST, OST48, KIAA0115 | | 2.4.1.119 |

TABLE 1-continued

| Locus ID | Gene Ab. | Reaction Stoichiometry | E.C. |
|---|---|---|---|
| 6184 | RPN1 | | 2.4.1.119 |
| 6185 | RPN2 | | 2.4.1.119 |
| 10130 | P5 | | 5.3.4.1 |
| 10954 | PDIR | | 5.3.4.1 |
| 11008 | PDI | | 5.3.4.1 |
| 2923 | GRP58, ERp57, ERp60, ERp61, GRP57, P58, PI-PLC, ERP57, ERP60, ERP61 | | 5.3.4.1 |
| 5034 | P4HB, PROHB, PO4DB, ERBA2L | | 5.3.4.1 |
| 7841 | GCS1 | | 3.2.1.106 |
| 4121 | MAN1A1, MAN9, HUMM9 | | 3.2.1.113 |
| 4245 | MGAT1, GLYT1, GLCNAC-TI, GNT-I, MGAT | | 2.4.1.101 |
| 4122 | MAN2A2, MANA2X | | 3.2.1.114 |
| 4124 | MAN2A1, MANA2 | | 3.2.1.114 |
| 4247 | MGAT2, CDGS2, GNT-II, GLCNACTII, GNT2 | | 2.4.1.143 |
| 4248 | MGAT3, GNT-III | | 2.4.1.144 |
| 6487 | SIAT6, ST3GALII | | 2.4.99.6 |
| 6480 | SIAT1 | | 2.4.99.1 |
| 2339 | FNTA, FPTA, PGGT1A | | 2.5.1.— |
| 2342 | FNTB, FPTB | | 2.5.1.— |
| 5229 | PGGT1B, BGGI, GGTI | | 2.5.1.— |
| 5875 | RABGGTA | | 2.5.1.— |
| 5876 | RABGGTB | | 2.5.1.— |
| 1352 | COX10 | | 2.5.1.— |
| 7.3 Glycoprotein degradation PATH: hsa00511 | | | |
| 4758 | NEU1, NEU | | 3.2.1.18 |
| 3073 | HEXA, TSD | | 3.2.1.52 |
| 3074 | HEXB | | 3.2.1.52 |
| 4123 | MAN2C1, MANA, MANA1, MAN6A8 | | 3.2.1.24 |
| 4125 | MAN2B1, MANB, LAMAN | | 3.2.1.24 |
| 4126 | MANBA, MANB1 | | 3.2.1.25 |
| 2517 | FUCA1 | | 3.2.1.51 |
| 2519 | FUCA2 | | 3.2.1.51 |
| 175 | AGA, AGU | | 3.5.1.26 |
| 7.4 Aminosugars metabolism PATH: hsa00530 | | | |
| 6675 | UAP1, SPAG2, AGX1 | UTP + NAGA1P <-> UDPNAG + PPI | 2.7.7.23 |
| 10020 | GNE, GLCNE | | 5.1.3.14 |
| 22951 | CMAS | | 2.7.7.43 |
| 1727 | DIA1 | | 1.6.2.2 |
| 4669 | NAGLU, NAG | | 3.2.1.50 |
| 7.5 Lipopolysaccharide biosynthesis PATH: hsa00540 | | | |
| 6485 | SIAT5, SAT3, STZ | | 2.4.99.— |
| 7903 | SIAT8D, PST, PST1, ST8SIA-IV | | 2.4.99.— |
| 8128 | SIAT8B, STX, ST8SIA-II | | 2.4.99.— |
| 7.7 Glycosaminoglycan degradation PATH: hsa00531 | | | |
| 3423 | IDS, MPS2, SIDS | | 3.1.6.13 |
| 3425 | IDUA, IDA | | 3.2.1.76 |
| 411 | ARSB | | 3.1.6.12 |
| 2799 | GNS, G6S | | 3.1.6.14 |
| 2588 | GALNS, MPS4A, GALNAC6S, GAS | | 3.1.6.4 |
| 8. Metabolism of Complex Lipids | | | |
| 8.1 Glycerolipid metabolism PATH: hsa00561 | | | |
| 10554 | AGPAT1, LPAAT-ALPHA, G15 | AGL3P + 0.017 C100ACP + 0.062 C120ACP + 0.100 C140ACP + 0.270 C160ACP + 0.169 C161ACP + 0.055 C180ACP + 0.235 C181ACP + 0.093 C182ACP -> PA + ACP | 2.3.1.51 |
| 10555 | AGPAT2, LPAAT-BETA | AGL3P + 0.017 C100ACP + 0.062 C120ACP + 0.100 C140ACP + 0.270 C160ACP + 0.169 C161ACP + 0.055 C180ACP + 0.235 C181ACP + 0.093 C182ACP -> PA + ACP | 2.3.1.51 |
| 1606 | DGKA, DAGK, DAGK1 | | 2.7.1.107 |
| 1608 | DGKG, DAGK3 | | 2.7.1.107 |
| 1609 | DGKQ, DAGK4 | | 2.7.1.107 |
| 8525 | DGKZ, DAGK5, HDGKZETA | | 2.7.1.107 |
| 8526 | DGKE, DAGK6, DGK | | 2.7.1.107 |
| 8527 | DGKD, DGKDELTA, KIAA0145 | | 2.7.1.107 |
| 1120 | CHKL | ATP + CHO -> ADP + PCHO | 2.7.1.32 |
| | EKI1 | ATP + ETHM -> ADP + PETHM | 2.7.1.82 |
| 1119 | CHK, CKI | ATP + CHO -> ADP + PCHO | 2.7.1.32 |
| 43 | ACHE, YT | | 3.1.1.7 |
| 1103 | CHAT | | 2.3.1.6 |
| 5337 | PLD1 | | 3.1.4.4 |

TABLE 1-continued

| Locus ID | Gene Ab. | Reaction Stoichiometry | E.C. |
|---|---|---|---|
| 26279 | PLA2G2D, SPLA2S | | 3.1.1.4 |
| 30814 | PLA2G2E | | 3.1.1.4 |
| 5319 | PLA2G1B, PLA2, PLA2A, PPLA2 | | 3.1.1.4 |
| 5320 | PLA2G2A, MOM1, PLA2B, PLA2L | | 3.1.1.4 |
| 5322 | PLA2G5 | | 3.1.1.4 |
| 8398 | PLA2G6, IPLA2 | | 3.1.1.4 |
| 8399 | PLA2G10, SPLA2 | | 3.1.1.4 |
| 1040 | CDS1 | PA + CTP <-> CDPDG + PPI | 2.7.7.41 |
| 10423 | PIS | CDPDG + MYOI -> CMP + PINS | 2.7.8.11 |
| 2710 | GK | GL + ATP -> GL3P + ADP | 2.7.1.30 |
| 2820 | GPD2 | GL3Pm + FADm -> T3P2m + FADH2m | 1.1.99.5 |
| 2819 | GPD1 | T3P2 + NADH <-> GL3P + NAD | 1.1.1.8 |
| 248 | ALPI | AHTD -> DHP + 3 PI | 3.1.3.1 |
| 249 | ALPL, HOPS, TNSALP | AHTD -> DHP + 3 PI | 3.1.3.1 |
| 250 | ALPP | AHTD -> DHP + 3 PI | 3.1.3.1 |
| 251 | ALPPL2 | AHTD -> DHP + 3 PI | 3.1.3.1 |
| 439 | ASNA1, ARSA-I | | 3.6.1.16 |
| 8694 | DGAT, ARGP1 | DAGLY + 0.017 C100ACP + 0.062 C120ACP + 0.100 C140ACP + 0.270 C160ACP + 0.169 C161ACP + 0.055 C180ACP + 0.235 C181ACP + 0.093 C182ACP -> TAGLY + ACP | 2.3.1.20 |
| 3989 | LIPB | | 3.1.1.3 |
| 3990 | LIPC, HL | | 3.1.1.3 |
| 5406 | PNLIP | | 3.1.1.3 |
| 5407 | PNLIPRP1, PLRP1 | | 3.1.1.3 |
| 5408 | PNLIPRP2, PLRP2 | | 3.1.1.3 |
| 8513 | LIPF, HGL, HLAL | | 3.1.1.3 |
| 4023 | LPL, LIPD | | 3.1.1.34 |
| 8443 | GNPAT, DHAPAT, DAP-AT | | 2.3.1.42 |
| 8540 | AGPS, ADAP-S, ADAS, ADHAPS, ADPS, ALDHPSY | | 2.5.1.26 |
| 4186 | MDCR, MDS, LIS1 | | 3.1.1.47 |
| 5048 | PAFAH1B1, LIS1, MDCR, PAFAH | | 3.1.1.47 |
| 5049 | PAFAH1B2 | | 3.1.1.47 |
| 5050 | PAFAH1B3 | | 3.1.1.47 |
| 5051 | PAFAH2, HSD-PLA2 | | 3.1.1.47 |
| 7941 | PLA2G7, PAFAH, LDL-PLA2 | | 3.1.1.47 |

8.2 Inositol phosphate metabolism PATH: hsa00562

| Locus ID | Gene Ab. | Reaction Stoichiometry | E.C. |
|---|---|---|---|
| 5290 | PIK3CA | ATP + PINS -> ADP + PINSP | 2.7.1.137 |
| 5291 | PIK3CB, PIK3C1 | ATP + PINS -> ADP + PINSP | 2.7.1.137 |
| 5293 | PIK3CD | ATP + PINS -> ADP + PINSP | 2.7.1.137 |
| 5294 | PIK3CG | ATP + PINS -> ADP + PINSP | 2.7.1.137 |
| 5297 | PIK4CA, PI4K-ALPHA | ATP + PINS -> ADP + PINS4P | 2.7.1.67 |
| 5305 | PIP5K2A | PINS4P + ATP -> D45PI + ADP | 2.7.1.68 |
| 5330 | PLCB2 | D45PI -> TPI + DAGLY | 3.1.4.11 |
| 5331 | PLCB3 | D45PI -> TPI + DAGLY | 3.1.4.11 |
| 5333 | PLCD1 | D45PI -> TPI + DAGLY | 3.1.4.11 |
| 5335 | PLCG1, PLC1 | D45PI -> TPI + DAGLY | 3.1.4.11 |
| 5336 | PLCG2 | D45PI -> TPI + DAGLY | 3.1.4.11 |
| 3612 | IMPA1, IMPA | MI1P -> MYOI + PI | 3.1.3.25 |
| 3613 | IMPA2 | MI1P -> MYOI + PI | 3.1.3.25 |
| 3628 | INPP1 | | 3.1.3.57 |
| 3632 | INPP5A | | |
| 3633 | INPP5B | | 3.1.3.56 |
| 3636 | INPPL1, SHIP2 | | 3.1.3.56 |
| 4952 | OCRL, LOCR, OCRL1, INPP5F | | 3.1.3.56 |
| 8867 | SYNJ1, INPP5G | | 3.1.3.56 |
| 3706 | ITPKA | | 2.7.1.127 |
| 51477 | ISYNA1 | G6P -> MI1P | 5.5.1.4 |
| 3631 | INPP4A, INPP4 | | 3.1.3.66 |
| 8821 | INPP4B | | 3.1.3.66 |

8.3 Sphingophospholipid biosynthesis PATH: hsa00570

| Locus ID | Gene Ab. | Reaction Stoichiometry | E.C. |
|---|---|---|---|
| 6609 | SMPD1, NPD | | 3.1.4.12 |

8.4 Phospholipid degradation PATH: hsa00580

| Locus ID | Gene Ab. | Reaction Stoichiometry | E.C. |
|---|---|---|---|
| 1178 | CLC | | 3.1.1.5 |
| 5321 | PLA2G4A, CPLA2-ALPHA, PLA2G4 | | 3.1.1.5 |

8.5 Sphingoglycolipid metabolism PATH: hsa00600

| Locus ID | Gene Ab. | Reaction Stoichiometry | E.C. |
|---|---|---|---|
| 10558 | SPTLC1, LCB1, SPTI | PALCOA + SER -> COA + DHSPH + CO2 | 2.3.1.50 |
| 9517 | SPTLC2, KIAA0526, LCB2 | PALCOA + SER -> COA + DHSPH + CO2 | 2.3.1.50 |
| 427 | ASAH, AC, PHP32 | | 3.5.1.23 |
| 7357 | UGCG, GCS | | 2.4.1.80 |
| 2629 | GDA G UC | | 3.2.1.45 |
| 2583 | GALGT, GALNACT | | 2.4.1.92 |
| 6489 | SIAT8A, SIAT8, ST8SIA-I | | 2.4.99.8 |

TABLE 1-continued

| Locus ID | Gene Ab. | Reaction Stoichiometry | E.C. |
|---|---|---|---|
| 6481 | SIAT2 | | 2.4.99.2 |
| 4668 | NAGA, D22S674, GALB | | 3.2.1.49 |
| 9514 | CST | | 2.8.2.11 |
| 410 | ARSA, MLD | | 3.1.6.8 |

8.6 Blood group glycolipid biosynthesis —lact series PATH: hsa00601

| | | | |
|---|---|---|---|
| 28 | ABO | | 2.4.1.40 |
| | | | 2.4.1.37 |
| 2525 | FUT3, LE | | 2.4.1.65 |
| 2527 | FUT5, FUC-TV | | 2.4.1.65 |
| 2528 | FUT6 | | 2.4.1.65 |
| 2523 | FUT1, H, HH | | 2.4.1.69 |
| 2524 | FUT2, SE | | 2.4.1.69 |

8.7 Blood group glycolipid biosynthesis —neolact series PATH: hsa00602

| | | | |
|---|---|---|---|
| 2651 | GCNT2, IGNT, NACGT1, NAGCT1 | | 2.4.1.150 |

8.8 Prostaglandin and leukotriene metabolism PATH: hsa00590

| | | | |
|---|---|---|---|
| 239 | ALOX12, LOG12 | | 1.13.11.31 |
| 246 | ALOX15 | | 1.13.11.33 |
| 240 | ALOX5 | | 1.13.11.34 |
| 4056 | LTC4S | | 2.5.1.37 |
| 4048 | LTA4H | | 3.3.2.6 |
| 4051 | CYP4F3, CYP4F, LTB4H | | 1.14.13.30 |
| 8529 | CYP4F2 | | 1.14.13.30 |
| 5742 | PTGS1, PGHS-1 | | 1.14.99.1 |
| 5743 | PTGS2, COX-2, COX2 | | 1.14.99.1 |
| 27306 | PGDS | | 5.3.99.2 |
| 5730 | PTGDS | | 5.3.99.2 |
| 5740 | PTGIS, CYP8, PGIS | | 5.3.99.4 |
| 6916 | TBXAS1, CYP5 | | 5.3.99.5 |
| 873 | CBR1, CBR | | 1.1.1.184 |
| | | | 1.1.1.189 |
| | | | 1.1.1.197 |
| 874 | CBR3 | | 1.1.1.184 |

9. Metabolism of Cofactors and Vitamins
9.2 Riboflavin metabolism PATH: hsa00740

| | | | |
|---|---|---|---|
| 52 | ACP1 | | 3.1.3.48 |
| | | FMN -> RIBOFLAV + PI | 3.1.3.2 |
| 53 | ACP2 | FMN -> RIBOFLAV + PI | 3.1.3.2 |
| 54 | ACP5, TRAP | FMN -> RIBOFLAV + PI | 3.1.3.2 |
| 55 | ACPP, PAP | FMN -> RIBOFLAV + PI | 3.1.3.2 |

9.3 Vitamin B6 metabolism PATH: hsa00750

| | | | |
|---|---|---|---|
| 8566 | PDXK, PKH, PNK | PYRDX + ATP -> P5P + ADP | 2.7.1.35 |
| | | PDLA + ATP -> PDLA5P + ADP | |
| | | PL + ATP -> PL5P + ADP | |

9.4 Nicotinate and nicotinamide metabolism PATH: hsa00760

| | | | |
|---|---|---|---|
| 23475 | QPRT | QA + PRPP -> NAMN + CO2 + PPI | 2.4.2.19 |
| 4837 | NNMT | | 2.1.1.1 |
| 683 | BST1, CD157 | NAD -> NAM + ADPRIB | 3.2.2.5 |
| 952 | CD38 | NAD -> NAM + ADPRIB | 3.2.2.5 |
| 23530 | NNT | | 1.6.1.2 |

9.5 Pantothenate and CoA biosynthesis PATH: hsa00770
9.6 Biotin metabolism PATH: hsa00780

| | | | |
|---|---|---|---|
| 3141 | HLCS, HCS | | 6.3.4.— |
| | | | 6.3.4.9 |
| | | | 6.3.4.10 |
| | | | 6.3.4.11 |
| | | | 6.3.4.15 |
| 686 | BTD | | 3.5.1.12 |

9.7 Folate biosynthesis PATH: hsa00790

| | | | |
|---|---|---|---|
| 2643 | GCH1, DYT5, GCH, GTPCH1 | GTP -> FOR + AHTD | 3.5.4.16 |
| 1719 | DHFR | DHF + NADPH -> NADP + THF | 1.5.1.3 |
| 2356 | FPGS | THF + ATP + GLU <-> ADP + PI + THFG | 6.3.2.17 |
| 8836 | GGH, GH | | 3.4.19.9 |
| 5805 | PTS | | 4.6.1.10 |
| 6697 | SPR | | 1.1.1.153 |
| 5860 | QDPR, DHPR, PKU2 | NADPH + DHBP -> NADP + THBP | 1.6.99.7 |

9.8 One carbon pool by folate PATH: hsa00670

| | | | |
|---|---|---|---|
| 10840 | FTHFD | | 1.5.1.6 |
| 10588 | MTHFS | ATP + FTHF -> ADP + PI + MTHF | 6.3.3.2 |

TABLE 1-continued

| Locus ID | Gene Ab. | Reaction Stoichiometry | E.C. |
|---|---|---|---|
| 9.10 Porphyrin and chlorophyll metabolism PATH: hsa00860 | | | |
| 210 | ALAD | 2 ALAV -> PBG | 4.2.1.24 |
| 3145 | HMBS, PBGD, UPS | 4 PBG -> HMB + 4 NH3 | 4.3.1.8 |
| 7390 | UROS | HMB -> UPRG | 4.2.1.75 |
| 7389 | UROD | UPRG -> 4 CO2 + CPP | 4.1.1.37 |
| 1371 | CPO, CPX | O2 + CPP -> 2 CO2 + PPHG | 1.3.3.3 |
| 5498 | PPOX, PPO | O2 + PPHGm -> PPIXm | 1.3.3.4 |
| 2235 | FECH, FCE | PPIXm -> PTHm | 4.99.1.1 |
| 3162 | HMOX1, HO-1 | | 1.14.99.3 |
| 3163 | HMOX2, HO-2 | | 1.14.99.3 |
| 644 | BLVRA, BLVR | | 1.3.1.24 |
| 645 | BLVRB, FLR | | 1.3.1.24 |
| | | | 1.6.99.1 |
| 2232 | FDXR, ADXR | | 1.18.1.2 |
| 3052 | HCCS, CCHL | | 4.4.1.17 |
| 1356 | CP | | 1.16.3.1 |
| 9.11 Ubiquinone biosynthesis PATH: hsa00130 | | | |
| 4938 | OAS1, IFI-4, OIAS | | 2.7.7.— |
| 4939 | OAS2, P69 | | 2.7.7.— |
| 5557 | PRIM1 | | 2.7.7.— |
| 5558 | PRIM2A, PRIM2 | | 2.7.7.— |
| 5559 | PRIM2B, PRIM2 | | 2.7.7.— |
| 7015 | TERT, EST2, TCS1, TP2, TRT | | 2.7.7.— |
| 8638 | OASL, TRIP14 | | 2.7.7.— |
| 10. Metabolism of Other Substances | | | |
| 10.1 Terpenoid biosynthesis PATH: hsa00900 | | | |
| 10.2 Flavonoids, stilbene and lignin biosynthesis PATH: hsa00940 | | | |
| 10.3 Alkaloid biosynthesis I PATH: hsa00950 | | | |
| 10.4 Alkaloid biosynthesis II PATH: hsa00960 | | | |
| 10.6 Streptomycin biosynthesis PATH: hsa00521 | | | |
| 10.7 Erythromycin biosynthesis PATH: hsa00522 | | | |
| 10.8 Tetracycline biosynthesis PATH: hsa00253 | | | |
| 10.14 gamma-Hexachlorocyclohexane degradation PATH: hsa00361 | | | |
| 5444 | PON1, ESA, PON | | 3.1.8.1 |
| | | | 3.1.1.2 |
| 5445 | PON2 | | 3.1.1.2 |
| | | | 3.1.8.1 |
| 10.18 1,2-Dichloroethane degradation PATH: hsa00631 | | | |
| 10.20 Tetrachloroethene degradation PATH: hsa00625 | | | |
| 2052 | EPHX1, EPHX, MEH | | 3.3.2.3 |
| 2053 | EPHX2 | | 3.3.2.3 |
| 10.21 Styrene degradation PATH: hsa00643 | | | |
| 11. Transcription (condensed) | | | |
| 11.1 RNA polymerase PATH: hsa03020 | | | |
| 11.2 Transcription factors PATH: hsa03022 | | | |
| 12. Translation (condensed) | | | |
| 12.1 Ribosome PATH: hsa03010 | | | |
| 12.2 Translation factors PATH: hsa03012 | | | |
| 1915 | EEF1A1, EF1A, ALPHA, EEF-1, EEF1A | | 3.6.1.48 |
| 1917 | EEF1A2, EF1A | | 3.6.1.48 |
| 1938 | EEF2, EF2, EEF-2 | | 3.6.1.48 |
| 12.3 Aminoacyl-tRNA biosynthesis PATH: hsa00970 | | | |
| 13. Sorting and Degradation (condensed) | | | |
| 13.1 Protein export PATH: hsa03060 | | | |
| 23478 | SPC18 | | 3.4.21.89 |
| 13.4 Proteasome PATH: hsa03050 | | | |
| 5687 | PSMA6, IOTA, PROS27 | | 3.4.99.46 |
| 5683 | PSMA2, HC3, MU, PMSA2, PSC2 | | 3.4.99.46 |
| 5685 | PSMA4, HC9 | | 3.4.99.46 |
| 5688 | PSMA7, XAPC7 | | 3.4.99.46 |
| 5686 | PSMA5, ZETA, PSC5 | | 3.4.99.46 |
| 5682 | PSMA1, HC2, NU, PROS30 | | 3.4.99.46 |
| 5684 | PSMA3, HC8 | | 3.4.99.46 |
| 5698 | PSMB9, LMP2, RING12 | | 3.4.99.46 |
| 5695 | PSMB7, Z | | 3.4.99.46 |
| 5691 | PSMB3, HC10-II | | 3.4.99.46 |
| 5690 | PSMB2, HC7-I | | 3.4.99.46 |
| 5693 | PSMB5, LMPX, MB1 | | 3.4.99.46 |
| 5689 | PSMB1, HC5, PMSB1 | | 3.4.99.46 |

TABLE 1-continued

| Locus ID | Gene Ab. | Reaction Stoichiometry | E.C. |
|---|---|---|---|
| 5692 | PSMB4, HN3, PROS26 | | 3.4.99.46 |

14. Replication and Repair
14.1 DNA polymerase PATH: hsa03030
14.2 Replication Complex PATH: hsa03032

| | | | |
|---|---|---|---|
| 23626 | SPO11 | | 5.99.1.3 |
| 7153 | TOP2A, TOP2 | | 5.99.1.3 |
| 7155 | TOP2B | | 5.99.1.3 |
| 7156 | TOP3A, TOP3 | | 5.99.1.2 |
| 8940 | TOP3B | | 5.99.1.2 |

22. Enzyme Complex
22.1 Electron Transport System, Complex I PATH: hsa03100
22.2 Electron Transport System, Complex II PATH: hsa03150
22.3 Electron Transport System, Complex III PATH: hsa03140
22.4 Electron Transport System, Complex IV PATH: hsa03130
22.5 ATP Synthase PATH: hsa03110
22.8 ATPases PATH: hsa03230
23. Unassigned
23.1 Enzymes

| | | | |
|---|---|---|---|
| 5538 | PPT1, CLN1, PPT, INCL | C160ACP + H2O -> C160 + ACP | 3.1.2.22 |

23.2 Non-enzymes

| | | | |
|---|---|---|---|
| 22934 | RPIA, RPI | RL5P <-> R5P | 5.3.1.6 |
| 5250 | SLC25A3, PHC | PI + H <-> Hm + PIm | |
| 6576 | | CIT + MALm <-> CITm + MAL | |
| 51166 | LOC51166 | AADP + AKG -> GLU + KADP | 2.6.1.39 |
| 5625 | PRODH | PRO + FAD -> P5C + FADH2 | 1.5.3.— |
| 6517 | SLC2A4, GLUT4 | GLCxt -> GLC | |
| 6513 | SLC2A1, GLUT1, GLUT | GLCxt -> GLC | |
| 26275 | HIBCH, HIBYL-COA-H | HIBCOAm + H2Om -> HIBm + COAm | 3.1.2.4 |
| 23305 | KIAA0837, ACS2, LACS5, LACS2 | C160 + COA + ATP -> AMP + PPI + C160COA | |
| 8611 | PPAP2A, PAP-2A | PA + H2O -> DAGLY + PI | |
| 8612 | PPAP2C, PAP-2C | PA + H2O -> DAGLY + PI | |
| 8613 | PPAP2B, PAP-2B | PA + H2O -> DAGLY + PI | |
| 56994 | LOC56994 | CDPCHO + DAGLY -> PC + CMP | |
| 10400 | PEMT, PEMT2 | SAM + PE -> SAH + PMME | |
| 5833 | PCYT2, ET | PETHM + CTP -> CDPETN + PPI | |
| 10390 | CEPT1 | CDPETN + DAGLY <-> CMP + PE | |
| 8394 | PIP5K1A | PINS4P + ATP -> D45PI + ADP | |
| 8395 | PIP5K1B, STM7, MSS4 | PINS4P + ATP -> D45PI + ADP | |
| 8396 | PIP5K2B | PINS4P + ATP -> D45PI + ADP | |
| 23396 | PIP5K1C, KIAA0589, PIP5K-GAMMA | PINS4P + ATP -> D45PI + ADP | |

24. Our own reactions which need to be found in KEGG

| | | | |
|---|---|---|---|
| | | GL3P <-> GL3Pm | |
| | | T3P2 <-> T3P2m | |
| | | PYR <-> PYRm + Hm | |
| | | ADP + ATPm + PI + H -> Hm + ADPm + ATP + PIm | |
| | | AKG + MALm <-> AKGm + MAL | |
| | | ASPm + GLU + H -> Hm + GLUm + ASP | |
| | | GDP + GTPm + PI + H -> Hm + GDPm + GTP + PIm | |
| | | C160Axt + FABP -> C160FP + ALBxt | |
| | | C160FP -> C160 + FABP | |
| | | C180Axt + FABP -> C180FP + ALBxt | |
| | | C180FP -> C180 + FABP | |
| | | C161Axt + FABP -> C161FP + ALBxt | |
| | | C161FP -> C161 + FABP | |
| | | C181Axt + FABP -> C181FP + ALBxt | |
| | | C181FP -> C181 + FABP | |
| | | C182Axt + FABP -> C182FP + ALBxt | |
| | | C182FP -> C182 + FABP | |
| | | C204Axt + FABP -> C204FP + ALBxt | |
| | | C204FP -> C204 + FABP | |
| | | O2xt -> O2 | |
| | | O2 <-> O2m | |
| | | ACTACm + SUCCOAm -> SUCCm + AACCOAm | |
| | | 3HB -> 3HBm | |
| | | MGCOAm + H2Om -> H3MCOAm | 4.2.1.18 |
| | | OMVAL -> OMVALm | |
| | | OIVAL -> OIVALm | |
| | | OICAP -> OICAPm | |
| | | C160CAR <-> C160CARm | |
| | | CAR <-> CARm | |
| | | DMMCOAm -> LMMCOAm | 5.1.99.1 |
| amino acid metabolism | | | |

TABLE 1-continued

| Locus ID Gene Ab. | Reaction Stoichiometry | E.C. |
|---|---|---|
| | THR -> NH3 + H2O + OBUT | 4.2.1.16 |
| | THR + NAD -> CO2 + NADH + AMA | 1.1.1.103 |
| | THR + NAD + COA -> NADH + ACCOA + GLY | |
| | AASA + NAD -> NADH + AADP | 1.2.1.31 |
| | FKYN + H2O -> FOR + KYN | 3.5.1.9 |
| | CMUSA -> CO2 + AM6SA | 4.1.1.45 |
| | AM6SA + NAD -> AMUCO + NADH | 1.2.1.32 |
| | AMUCO + NADPH -> KADP + NADP + NH4 | 1.5.1.— |
| | CYSS + AKG <-> GLU + SPYR | |
| | URO + H2O -> 4I5P | 4.2.1.49 |
| | 4I5P + H2O -> FIGLU | 3.5.2.7 |
| | GLU <-> GLUm + Hm | |
| | ORN + Hm -> ORNm | |
| | ORN + Hm + CITRm <-> CITR + ORNm | |
| | GLU + ATP + NADPH -> NADP + ADP + PI + GLUGSAL | |
| | GLYAm + ATPm -> ADPm + 2PGm | |
| | AM6SA -> PIC | |
| | SPYR + H2O -> H2SO3 + PYR | |
| | P5C <-> GLUGSAL | |
| fatty acid synthesis | | |
| | MALCOA + ACP <-> MALACP + COA | 2.3.1.39 |
| | ACCOA + ACP <-> ACACP + COA | |
| | ACACP + 4 MALACP + 8 NADPH -> 8 NADP + C100ACP + 4 CO2 + 4 ACP | |
| | ACACP + 5 MALACP + 10 NADPH -> 10 NADP + C120ACP + 5 CO2 + 5 ACP | |
| | ACACP + 6 MALACP + 12 NADPH -> 12 NADP + C140ACP + 6 CO2 + 6 ACP | |
| | ACACP + 6 MALACP + 11 NADPH -> 11 NADP + C141ACP + 6 CO2 + 6 ACP | |
| | ACACP + 7 MALACP + 14 NADPH -> 14 NADP + C160ACP + 7 CO2 + 7 ACP | |
| | ACACP + 7 MALACP + 13 NADPH -> 13 NADP + C161ACP + 7 CO2 + 7 ACP | |
| | ACACP + 8 MALACP + 16 NADPH -> 16 NADP + C180ACP + 8 CO2 + 8 ACP | |
| | ACACP + 8 MALACP + 15 NADPH -> 15 NADP + C181ACP + 8 CO2 + 8 ACP | |
| | ACACP + 8 MALACP + 14 NADPH -> 14 NADP + C182ACP + 8 CO2 + 8 ACP | |
| | C160COA + CAR -> C160CAR + COA | |
| | C160CARm + COAm -> C160COAm + CARm | |
| fatty acid degredation | | |
| | GL3P + 0.017 C100ACP + 0.062 C120ACP + 0.1 C140ACP + 0.27 C160ACP + 0.169 C161ACP + 0.055 C180ACP + 0.235 C181ACP + 0.093 C182ACP -> AGL3P + ACP | |
| | TAGLYm + 3 H2Om -> GLm + 3 C160m | |
| Phospholipid metabolism | | |
| | SAM + PMME -> SAH + PDME | |
| | PDME + SAM -> PC + SAH | |
| | PE + SER <-> PS + ETHM | |
| Muscle contraction | | |
| | MYOACT + ATP -> MYOATP + ACTIN | |
| | MYOATP + ACTIN -> MYOADPAC | |
| | MYOADPAC -> ADP + PI + MYOACT + CONTRACT | |

TABLE 2

// Homo Sapiens Core Metabolic Network //
// Glycolysis //
−1 GLC −1 ATP +1 G6P +1 ADP 0 HK1
−1 G6P −1 H2O +1 GLC +1 PI 0 G6PC
−1 G6P +1 F6P 0 GPIR
−1 F6P −1 ATP +1 FDP +1 ADP 0 PFKL
−1 FDP −1 H2O +1 F6P +1 PI 0 FBP1
−1 FDP +1 T3P2 +1 T3P1 0 ALDOAR
−1 T3P2 +1 T3P1 0 TPI1R
−1 T3P1 −1 PI −1 AND +1 NADH +1 13PDG 0 GAPDR
−1 13PDG −1 ADP +1 3PG +1 ATP 0 PGK1R
−1 13PDG +1 23PDG 0 PGAM1

TABLE 2-continued

−1 23PDG −1 H2O +1 3PG +1 PI 0 PGAM2
−1 3PG +1 2PG 0 PGAM3R
−1 2PG +1 PEP +1 H2O 0 ENO1R
−1 PEP −1 ADP +1 PYR +1 ATP 0 PKLR
−1 PYRm −1 COAm −1 NADm +1 NADHm +1 CO2m +1 ACCOAm 0 PDHA1
−1 AND −1 LAC +1 PYR +1 NADH 0 LDHAR
−1 G1P +1 G6P 0 PGM1R
// TCA //
−1 ACCOAm −1 OAm −1 H2Om +1 COAm +1 CITm 0 CS
−1 CIT +1 ICIT 0 ACO1R
−1 CITm +1 ICITm 0 ACO2R

TABLE 2-continued

```
-1 ICIT -1 NADP +1 NADPH +1 CO2 +1 AKG 0 IDH1
-1 ICITm -1 NADPm +1 NADPHm +1 CO2m +1 AKGm 0 IDH2
-1 ICITm -1 NADm +1 CO2m +1 NADHm +1 AKOm 0 IDH3A
-1 AKGm -1 NADm -1 COAm +1 CO2m +1
NADHm +1 SUCCOAm 0 OGDH
-1 GTPm -1 SUCCm -1 COAm +1
GDPm +1 PIm +1 SUCCAm 0 SUCLG1R
-1 ATPm -1 SUCCm -1 COAm +1
ADPm +1 PIm +1 SUCCAm 0 SUCLA2R
-1 FUMm -1 H2Om +1 MALm 0 FHR
-1 MAL -1 AND +1 NADH +1 OA 0 MDH1R
-1 MALm -1 NADm +1 NADHm +1 OAm 0 MDH2R
-1 PYRm -1 ATPm -1 CO2m +1 ADPm +1 OAm +1 PIm 0 PC
-1 OA -1 GTP +1 PEP +1 GDP +1 CO2 0 PCK1
-1 OAm -1 GTPm +1 PEPm +1 GDPm +1 CO2m 0 PCK2
-1 ATP -1 CIT -1 COA -1 H2O +1
ADP +1 PI +1 ACCOA +1 OA 0 ACLY
// PPP //
-1 G6P -1 NADP +1 D6PGL +1 NADPH 0 G6PDR
-1 D6PGL -1 H2O +1 D6PGC 0 PGLS
-1 D6PGC -1 NADP +1 NADPH +1 CO2 +1 RL5P 0 PGD
-1 RL5P +1 X5P 0 RPER
-1 R5P -1 X5P +1 T3P1 +1 S7P 0 TKT1R
-1 X5P -1 E4P +1 F6P +1 T3P1 0 TKT2R
1 T3P1 -1 S7P +1 E4P +1 F6P 0 TALDO1R
-1 RL5P +1 R5P 0 RPIAR
// Glycogen //
-1 G1P -1 UTP +1 UDPG +1 PPI 0 UGP1
-1 UDPG +1 UDP +1 GLYCOGEN 0 GYS1
-1 GLYCOGEN -1 PI +1 G1P 0 GBE1
// ETS //
-1 MALm -1 NADPm +1 CO2m +1 NADPHm +1 PYRm 0 ME3
-1 MALm -1 NADm +1 CO2m +1 NADHm +1 PYRm 0 ME2
-1 MAL -1 NADP +1 CO2 +1 NADPH +1 PYR 0 ME1
-1 NADHm -1 Qm -4 Hm +1 QH2m +1 NADm +4 H 0 MTND1
-1 SUCCm -1 FADm +1 FUMm +1 FADH2m 0 SDHC1R
-1 FADH2m -1 Qm +1 FADm +1 QH2m 0 SDHC2R
-1 O2m -4 FEROm -4 Hm +4 FERIm +2 H2Om +4 H 0 UQCRFS1
-1 QH2m -2 FERIm -4 Hm +1 Qm +2 FEROm +4 H 0 COX5BL4
-1 ADPm -1 PIm -3 H +1 ATPm +3 Hm +1 H2Om 0 MTAT
-1 ADP -1 ATPm -1 PI -1 H +1
Hm +1 ADPm +1 ATP +1 PIm 0 ATPMC
-1 GDP -1 GTPm -1 PI -1 H +1
Hm +1 GDPm +1 GTP +1 PIm 0 GTPMC
-1 PPI +2 PI 0 PP
-1 ACCOA -1 ATP -1 C02 +1 MALCOA +1 ADP +1 PT 0 ACACAR
-1 GDP -1 ATP +1 GTP +1 ADP 0 GOT3R
```

```
// Transporters //
-1 CIT -1 MALm +1 CITm +1 MAL 0 CITMCR
-1 PYR -1 H +1 PYRm +1 Hm 0 PYRMCR
// Glycerol Phosphate Shuttle //
-1 GL3Pm -1 FADm +1 T3P2m +1 FADH2m 0 GPD2
-1 T3P2 -1 NADH +1 GL3P +1 AND 0 GPD1
-1 GL3P +1 GL3Pm 0 GL3PMCR
-1 T3P2 +1 T3P2m 0 T3P2MCR
// Malate/Aspartate Shuttle //
-1 OAm -1 GLUm +1 ASPm +1 AKGm 0 GOT1R
-1 ASP -1 AKG +1 OA +1 GLU 0 GOT2R
-1 AKG -1 MALm +1 AKGm +1 MAL 0 MALMCR
-1 ASPm -1 GLU -1 H +1 Hm +1 GLUm +1 ASP 0 ASPMC
// Exchange Fluxes //
+1 GLC 0 GLCexR
+1 PYR 0 PYRexR
+1 CO2 0 CO2exR
+1 O2 0 O2exR
+1 PI 0 PIexR
+1 H2O 0 H2OexR
+1 LAC 0 LACexR
+1 CO2m 0 CO2min
-1 CO2m 0 CO2mout
+1 O2m 0 O2min
-1 O2m 0 O2mout
+1 H2Om 0 H2Omin
-1 H2Om 0 H2Omout
+1 PIm 0 PImin
-1 PIm 0 PImout
// Output //
-1 ATP +1 ADP +1 PI 0 Output
0.0 end
end E 0
max
1 Output
0 end
0 GLCexR 1
-1000 PYRexR 0
-1000 LACexR 0
0 end 0
rev. rxn 33
nonrev. rxn 31
total rxn 64
matrix columns 97
unique enzymes 52
```

TABLE 3

| Abbrev. | Reaction | Rxn Name |
|---|---|---|
| Glycolysis | | |
| HK1 | GLC + ATP -> G6P + ADP | HK1 |
| G6PC, G6PT | G6P + H20 -> GLC + P1 | G6PC |
| GPI | G6P <-> F6P | GPI |
| PFKL | F6P + ATP -> FDP + ADP | PFKL |
| FBP1, FBP | FDP + H2O -> F6P + PI | FBP1 |
| ALDOA | FDP <-> T3P2 + T3P1 | ALDOA |
| TPI1 | T3P2 <-> T3P1 | TPI1 |
| GAPD, GAPDH | T3P1 + PI + NAD <-> NADH + 13PDG | GAPD |
| PGK1, PGKA | 13PDG + ADP <-> 3PG + ATP | PGK1 |
| PGAM1, PGAMA | 13PDG <-> 23PDG | PGAM1 |
| | 23PDG + H2O -> 3PG + P1 | PGAM2 |
| | 3PG <-> 2PG | PGAM3 |
| ENO1, PPH, ENO1L1 | 2PG <-> PEP + H2O | ENO1 |
| PKLR, PK1 | PEP + ADP -> PYR + ATP | PKLR |
| PDHA1, PHE1A, PDHA | PYRm + COAm + NADm -> + NADHm + CO2m + ACCOAm | PDHA1 |
| LDHA, LDH1 | NAD + LAC <-> PYR + NADH | LDHA |
| PGM1 | G1P <-> G6P | PGM1 |
| TCA | | |
| CS | ACCOAm + OAm + H2Om -> COAm + CITm | CS |
| ACO1, IREB1, IRP1 | CIT <-> ICIT | ACO1 |
| ACO2 | CITm <-> ICITm | ACO2 |
| IDH1 | ICIT + NADP -> NADPH + CO2 + AKG | IDH1 |
| IDH2 | ICITm + NADPm -> NADPHm + CO2m + AKGm | IDH2 |

TABLE 3-continued

| Abbrev. | Reaction | Rxn Name |
|---|---|---|
| IDH3A | ICITm + NADm -> CO2m + NADHm + AKGm | IDH3A |
| OGDH | AKGm + NADm + COAm -> CO2m + NADHm + SUCCOAm | OGDH |
| SUCLG1, SUCLA1 | GTPm + SUCCm + COAm <-> GDPm + PIm + SUCCOAm | SUCLG1 |
| SUCLA2 | ATPm + SUCCm + COAm <-> ADPm + PIm + SUCCOAm | SUCLA2 |
| FH | FUMm + H2Om <-> MALm | FH |
| MDH1 | MAL + NAD <-> NADH + OA | MDH1 |
| MDH2 | MALm + NADm <-> NADHm + OAm | MDH2 |
| PC, PCB | PYRm + ATPm + CO2m -> ADPm + OAm + PIm | PC |
| ACLY, ATPCL, CLATP | ATP + CIT + COA + H2O -> ADP + PI + ACCOA + OA | ACLY |
| PCK1 | OA + GTP -> PEP + GDP + CO2 | PCK1 |
| PPP | | |
| G6PD, G6PD1 | G6P + NADP <-> D6PGL + NADPH | G6PD |
| PGLS, 6PGL | D6PGL + H2O -> D6PGC | PGLS |
| PGD | D6PGC + NADP -> NADPH + CO2 + RL5P | PGD |
| RPE | RL5P <-> X5P | RPE |
| TKT | R5P + X5P <-> T3P1 + S7P | TKT1 |
|  | X5P + E4P <-> F6P + T3P1 | TKT2 |
| TALDO1 | T3P1 + S7P <-> E4P + F6P | TALDO1 |
| UGP1 | G1P + UTP -> UDPG + PPI | UGP1 |
| ACACA, ACAC, ACC | ACCOA + ATP + CO2 <-> MALCOA + ADP + PI + H | ACACA |
| ETS | | |
| ME3 | MALm + NADPm -> CO2m + NADPHm + PYRm | ME3 |
| MTND1 | NADHm + Qm + 4 Hm -> QH2m + NADm + 4 H | MTND1 |
| SDHC | SUCCm + FADm <-> FUMm + FADH2m | SDHC1 |
|  | FADH2m + Qm <-> FADm + QH2m | SDHC2 |
| UQCRFS1, RIS1 | O2m + 4 FEROm + 4 Hm -> 4 FERIm + 2 H2Om + 4 H | UQCRFS1 |
| COX5BL4 | QH2m + 2 FERIm + 4 Hm -> Qm + 2 FEROm + 4 H | COX5BL4 |
| MTATP6 | ADPm + PIm + 3 H -> ATPm + 3 Hm + H2Om | MTAT |
| PP, SID6-8061 | PPI -> 2 PI | PP |
| Malate Aspartate shunttle | | |
| GOT1 | OAm + GLUm <-> ASPm + AKGm | GOT1 |
| GOT2 | OA + GLU <-> ASP + AKG | GOT2 |
|  | GDP + ATP <-> GTP + ADP | GOT3 |
| Glycogen | | |
| GBE1 | GLYCOGEN + PI -> G1P | GBE1 |
| GYS1, GYS | UDPG -> UDP + GLYCOGEN | GYS1 |
| Glycerol Phosphate Shunttle | | |
| GPD2 | GL3Pm + FADm -> T3P2m + FADH2m | GPD2 |
| GPD1 | T3P2 + NADH -> GL3P + NAD | GPD1 |
| RPIA, RPI | RL5P <-> R5P | RPIA |
| Mitochondria Transport | | |
|  | CIT + MALm <-> CITm + MAL | CITMC |
|  | GL3P <-> GL3Pm | GL3PMC |
|  | T3P2 <-> T3P2m | T3P2MC |
|  | PYR <-> PYRm + Hm | PYRMC |
|  | ADP + ATPm + PI + H -> Hm + ADPm + ATP + PIm | ATPMC |
|  | AKG + MALm <-> AKGm + MAL | MALMC |
|  | ASPm + GLU + H -> Hm + GLUm + ASP | ASPMC |
|  | GDP + GTPm + PI + H -> Hm + GDPm + GTP + PIm | GTPMC |

TABLE 4

Metabolic Reaction for Muscle Cells

| Reaction | Rxt Name |
|---|---|
| GLC + ATP -> G6P + ADP | 0 HK1 |
| G6P <-> F6P | 0 GPI |
| F6P + ATP -> FDP + ADP | 0 PFKL1 |
| FDP + H2O -> F6P + PI | 0 FBP1 |
| FDP <-> T3P2 + T3P1 | 0 ALDOA |
| T3P2 <-> T3P1 | 0 TPI1 |
| T3P1 + PI + NAD <-> NADH + 13PDG | 0 GAPD |
| 13PDG + ADP <-> 3PG + ATP | 0 PGK1 |
| 3PG <-> 2PG | 0 PGAM3 |
| 2PG <-> PEP + H2O | 0 ENO1 |
| PEP + ADP -> PYR + ATP | 0 PK1 |
| PYRm + COAm + NADm -> + NADHm + CO2m + ACCOAm | 0 PDHA1 |
| NAD + LAC <-> PYR + NADH | 0 LDHA |

TABLE 4-continued

| Metabolic Reaction for Muscle Cells | |
|---|---|
| Reaction | Rxt Name |
| G1P <-> G6P | 0 PGM1 |
| ACCOAm + OAm + H2Om -> COAm + CITm | 0 CS |
| CIT <-> ICIT | 0 ACO1 |
| CITm <-> ICITm | 0 ACO2 |
| ICIT + NADP -> NADPH + CO2 + AKG | 0 IDH1 |
| ICITm + NADPm -> NADPHm + CO2m + AKGm | 0 IDH2 |
| ICITm + NADm -> CO2m + NADHm + AKGm | 0 IDH3A |
| AKGm + NADm + COAm -> CO2m + NADHm + SUCCOAm | 0 OGDH |
| GTPm + SUCCm + COAm <-> GDPm + PIm + SUCCOAm | 0 SUCLG1 |
| ATPm + SUCCm + COAm <-> ADPm + PIm + SUCCOAm | 0 SUCLA2 |
| FUMm + H2Om <-> MALm | 0 FH |
| MAL + NAD <-> NADH + OA | 0 MDH1 |
| MALm + NADm <-> NADHm + OAm | 0 MDH2 |
| PYRm + ATPm + CO2m -> ADPm + OAm + PIm | 0 PC |
| ATP + CIT + COA + H2O -> ADP + PI + ACCOA + OA | 0 ACLY |
| OA + GTP -> PEP + GDP + CO2 | 0 PCK1 |
| OAm + GTPm -> PEPm + GDPm + CO2m | 0 PCK2 |
| G6P + NADP <-> D6PGL + NADPH | 0 G6PD |
| D6PGL + H2O -> D6PGC | 0 H6PD |
| D6PGC + NADP -> NADPH + CO2 + RL5P | 0 PGD |
| RL5P <-> X5P | 0 RPE |
| R5P + X5P <-> T3P1 + S7P | 0 TKT1 |
| X5P + E4P <-> F6P + T3P1 | 0 TKT2 |
| T3P1 + S7P <-> E4P + F6P | 0 TALDO1 |
| RL5P <-> R5P | 0 RPIA |
| G1P + UTP -> UDPG + PPI | 0 UGP1 |
| GLYCOGEN + PI -> G1P | 0 GBE1 |
| UDPG -> UDP + GLYCOGEN | 0 GYS1 |
| MALm + NADm -> CO2m + NADHm + PYRm | 0 ME2 |
| MALm + NADPm -> CO2m + NADPHm + PYRm | 0 ME3 |
| MAL + NADP -> CO2 + NADPH + PYR | 0 HUMNDME |
| NADHm + Qm + 4 Hm -> QH2m + NADm + 4 H | 0 MTND1 |
| SUCCm + FADm <-> FUMm + FADH2m | 0 SDHC1 |
| FADH2m + Qm <-> FADm + QH2m | 0 SDHC2 |
| O2m + 4 FEROm + 4 Hm -> 4 FERIm + 2 H2Om + 4 H | 0 UQCRFS1 |
| QH2m + 2 FERIm + 4 Hm -> Qm + 2 FEROm + 4 H | 0 COX5BL4 |
| ADPm + PIm + 3 H -> ATPm + 3 Hm + H2Om | 0 MTAT1 |
| ADP + ATPm + PI + H -> Hm + ADPm + ATP + PIm | 0 ATPMC |
| GDP + GTPm + PI + H -> Hm + GDPm + GTP + PIm | 0 GTPMC |
| PPI -> 2 PI | 0 PP |
| GDP + ATP <-> GTP + ADP | 0 NME1 |
| ACCOA + ATP + CO2 <-> MALCOA + ADP + PI + H | 0 ACACA |
| MALCOA + ACP <-> MALACP + COA | 0 FAS1_1 |
| ACCOA + ACP <-> ACACP + COA | 0 FAS1_2 |
| ACACP + 4 MALACP + 8 NADPH -> 8 NADP + C100ACP + 4 CO2 + 4 ACP | 0 C100SY |
| ACACP + 5 MALACP + 10 NADPH -> 10 NADP + C120ACP + 5 CO2 + 5 ACP | 0 C120SY |
| ACACP + 6 MALACP + 12 NADPH -> 12 NADP + C120ACP + 6 CO2 + 6 ACP | 0 C140SY |
| ACACP + 6 MALACP + 11 NADPH -> 11 NADP + C141ACP + 6 CO2 + 6 ACP | 0 C141SY |
| ACACP + 7 MALACP + 14 NADPH -> 14 NADP + C160ACP + 7 CO2 + 7 ACP | 0 C160SY |
| ACACP + 7 MALACP + 13 NADPH -> 13 NADP + C161ACP + 7 CO2 + 7 ACP | 0 C161SY |
| ACACP + 8 MALACP + 16 NADPH -> 16 NADP + C180ACP + 8 CO2 + 8 ACP | 0 C180SY |
| ACACP + 8 MALACP + 15 NADPH -> 15 NADP + C181ACP + 8 CO2 + 8 ACP | 0 C181SY |
| ACACP + 8 MALACP + 14 NADPH -> 14 NADP + C182ACP + 8 CO2 + 8 ACP | 0 C182SY |
| C160ACP + H2O -> C160 + ACP | 0 PPT1 |
| C160 + COA + ATP -> AMP + PPI + C160COA | 0 KIAA |
| C160COA + CAR -> C160CAR + COA | 0 C160CA |
| C160CARm + COAm -> C160COAm + CARm | 0 C160CB |
| C160CARm + COAm + FADm + NADm -> FADH2m + NADHm + C140COAm + ACCOAm | 0 HADHA |
| C140COAm + 7 COAm + 7 FADm + 7 NADm -> 7 FADH2m + 7 NADHm + 7 ACCOAm | 0 HADH2 |
| TAGLYm + 3 H2Om -> GLm + 3 C160m | 0 TAGRXN |
| GL3P + 0.017 C100ACP + 0.062 C120ACP + 0.1 C140ACP + 0.27 C160ACP + 0.169 C161ACP + 0.055 C180ACP + 0.235 C181ACP + 0.093 C182CP -> AGL3P + ACP | 0 GAT1 |
| AGL3P + 0.017 C100ACP + 0.062 C120ACP + 0.100 C140ACP + 0.270 C160ACP + 0.169 C161ACP + 0.055 C180ACP + C181ACP + 0.093 C182ACP -> PA + ACP | 0 AGPAT1 |

TABLE 4-continued

Metabolic Reaction for Muscle Cells

| Reaction | Rxt Name |
|---|---|
| ATP + CHO -> ADP + PCHO | 0 CHKL1 |
| PCHO + CTP -> CDPCHO + PPI | 0 PCYT1A |
| CDPCHO + DAGLY -> PC + CMP | 0 LOC |
| SAM + PE -> SAH + PMME | 0 PEMT |
| SAM + PMME -> SAH + PDME | 0 MFPS |
| PDME + SAM -> PC + SAH | 0 PNMNM |
| G6P -> MI1P | 0 ISYNA1 |
| MI1P -> MYOI + PI | 0 IMPA1 |
| PA + CTP <-> CDPDG + PPI | 0 CDS1 |
| CDPDG + MYOI -> CMP + PINS | 0 PIS |
| ATP + PINS -> ADP + PINSP | 0 PIK3CA |
| ATP + PINS -> ADP + PINS4P | 0 PIK4CA |
| PINS4P + ATP -> D45PI + ADP | 0 PIP5K1 |
| D45PI -> TPI + DAGLY | 0 PLCB2 |
| PA + H2O -> DAGLY + PI | 0 PPAP2A |
| DAGLY + 0.017 C100ACP + 0.062 C120ACP + 0.100 C140ACP + 0.270 C160ACP + 0.169 C161ACP + 0.055 C180ACP + 0.235 C181ACP + 0.093 C182ACP -> TAGLY + ACP | 0 DGAT |
| CDPDG + SER <-> CMP + PS | 0 PTDS |
| CDPETN + DAGLY <-> CMP + PE | 0 CEPT1 |
| PE + SER <-> PS + ETHM | 0 PESER |
| ATP + ETHM -> ADP + PETHM | 0 EKI1 |
| PETHM + CTP -> CDPETN + PPI | 0 PCYT2 |
| PS -> PE + CO2 | 0 PISD |
| 3HBm + NADm -> NADHm + Hm + ACTACm | 0 BDH |
| ACTACm + SUCCOAm -> SUCCm + AACOAm | 0 3OCT |
| THF + SER <-> GLY + METTHF | 0 SHMT1 |
| THFm + SERm <-> GLYm + METTHFm | 0 SHMT2 |
| SERm + PYRm <-> ALAm + 3HPm | 0 AGXT |
| 3PG + NAD <-> NADH + PHP | 0 PHGDH |
| PHP + GLU <-> AKG + 3PSER | 0 PSA |
| 3PSER + H2O -> PI + SER | 0 PSPH |
| 3HPm + NADHm -> NADm + GLYAm | 0 GLYD |
| SER -> PYR + NH3 + H2O | 0 SDS |
| GLYAm + ATPm -> ADPm + 2PGm | 0 GLTK |
| PYR + GLU <-> AKG + ALA | 0 GPT |
| GLUm + CO2m + 2 ATPm -> 2 ADPm + 2 PIm + CAPm | 0 CPS1 |
| AKGm + NADHm + NH3m <-> NADm + H2Om + GLUm | 0 GLUD1 |
| AKGm + NADPHm + NH3m <-> NADPm + H2Om + GLUm | 0 GLUD2 |
| GLUm + NH3m + ATPm -> GLNm + ADPm + PIm | 0 GLUL |
| ASPm + ATPm + GLNm -> GLUm + ASNm + AMPm + PPIm | 0 ASNS |
| ORN + AKG <-> GLUGSAL + GLU | 0 OAT |
| GLU <-> GLUm + Hm | 0 GLUMT |
| GLU + ATP + NADPH -> NADP + ADP + PI + GLUGSAL | 0 P5CS |
| GLUP + NADH -> NAD + PI + GLUGSAL | 0 PYCS |
| P5C <-> GLUGSAL | 0 SPTC |
| HIS -> NH3 + URO | 0 HAL |
| URO + H2O -> 4I5P | 0 UROH |
| 4I5P + H2O -> FIGLU | 0 IMPR |
| FIGLU + THF -> NFTHF + GLU | 0 FTCD |
| MET + ATP + H2O -> PPI + PI + SAM | 0 MAT1A |
| SAM + DNA -> SAH + DNA5MC | 0 DNMT1 |
| SAH + H2O -> HCYS + ADN | 0 AHCYL1 |
| HCYS + MTHF -> THF + MET | 0 MTR |
| SER + HCYS -> LLCT + H2O | 0 CBS |
| LLCT + H2O -> CYS + HSER | 0 CTH1 |
| OBUT + NH3 <-> HSER | 0 CTH2 |
| CYS + O2 <-> CYSS | 0 CDO1 |
| CYSS + AKG <-> GLU + SPYR | 0 CYSAT |
| SPYR + H2O -> H2SO3 + PYR | 0 SPTB |
| LYS + NADPH + AKG -> NADP + H2O + SAC | 0 LKR1 |
| SAC + H2O + NAD -> GLU + NADH + AASA | 0 LKR2 |
| AASA + NAD -> NADH + AADP | 0 2ASD |
| AADP + AKG -> GLU + KADP | 0 LOC5 |
| TRP + O2 -> FKYN | 0 TDO2 |
| FKYN + H2O -> FOR + KYN | 0 KYNF |
| KYN + NADPH + O2 -> HKYN + NADP + H2O | 0 KMO |
| HKYN + H2O -> HAN + ALA | 0 KYNU2 |
| HAN + O2 -> CMUSA | 0 HAAO |
| CMUSA -> CO2 + AM6SA | 0 ACSD |
| AM6SA -> PIC | 0 SPTA |
| AM6SA + NAD -> AMUCO + NADH | 0 AMSD |
| AMUCO + NADPH -> KADP + NADP + NH4 | 0 2AMR |
| ARG -> ORN + UREA | 0 ARG2 |
| ORN + Hm -> ORNm | 0 ORNMT |
| ORN + Hm + CITRm <-> CITR + ORNm | 0 ORNCITT |

TABLE 4-continued

Metabolic Reaction for Muscle Cells

| Reaction | Rxt Name |
|---|---|
| ORNm + CAPm -> CITRm + Pim + Hm | 0 OTC |
| CITR + ASP + ATP <-> AMP <-> AMP + PPI + ARGSUCC | 0 ASS |
| ARGSUCC -> FUM + ARG | 0 ASL |
| PRO + FAD -> P5C + FADH2 | 0 PRODH |
| P5C + NADPH -> PRO + NADP | 0 PYCR1 |
| THR -> NH3 + H2O + OBUT | 0 WTDH |
| THR + NAD -> CO2 + NADH + AMA | 0 TDH |
| AMA + H2O + FAD -> NH3 + FADH2 + MTHGXL | 0 MAOA |
| GLYm + THFm + NADm <-> METTHFm + NADHm + CO2m + NH3m | 0 AMT |
| PHE + THBP + O2 -> TYR + DHBP + H2O | 0 PAH |
| NADPH + DHBP -> NADP + THBP | 0 QDPR |
| AKG + TYR -> HPHPYR + GLU | 0 TAT |
| HPHPYR + O2 -> HGTS + CO2 | 0 HPD |
| HGTS + O2 -> MACA | 0 HGD |
| MACA -> FACA | 0 GSTZ1 |
| FACA + H2O -> FUM + ACA | 0 FAH |
| AKG + ILE -> OMVAL + GLU | 0 BCAT1A |
| OMVALm + COAm + NADm -> MBCOAm + NADHm + CO2m | 0 BCKDHAA |
| MBCOAm + FADm -> MCCOAm + FADH2m | 0 ACADMA |
| MCCOAm + H2Om -> MHVCOAm | 0 ECHS1B |
| MHVCOAm + NADm -> MAACOAm + NADHm | 0 EHHADHA |
| MAACOAm -> ACCOAm + PROPCOAm | 0 ACAA2 |
| 2 ACCOAm <-> COAm + AACCOAm | 0 ACATm1 |
| AKG + VAL -> OIVAL + GLU | 0 BCAT1B |
| OIVALm + COAm + NADm -> IBCOAm + NADHm + CO2m | 0 BCKDHAB |
| IBCOAm + FADm -> MACOAm + FADH2m | 0 ACADSB |
| MACOAm + H2Om -> HIBCOAm | 0 EHHADHC |
| HIBCOAm + H2Om -> HIBm + COAm | 0 HIBCHA |
| HIBm + NADm -> MMAm + NADHm | 0 EHHADHB |
| MMAm + COAm + NADm -> NADHm + CO2m + PROPCOAm | 0 MMSDH |
| PROPCOAm + CO2m + ATPm -> ADPm + PIm + DMMCOAm | 0 PCCA |
| DMMCOAm -> LMMCOAm | 0 HIBCHF |
| LMMCOAm -> SUCCOAm | 0 MUT |
| AKG + LEU -> OICAP + GLU | 0 BCAT1C |
| OICAPm + COAm + NADm -> IVCOAm + NADHm + CO2m | 0 BCKDHAC |
| OICAPm + COAm + NADH -> IVCOAm + NADHm + CO2m | 0 BCKDHBC |
| OICAPm + COAm + NADHm -> IVCOAm + NADHm + CO2m | 0 DBTC |
| IVCOAm + FADm -> MCRCOAm + FADH2m | 0 IVD |
| MCRCOAm + ATPm + CO2m + H2Om -> MGCOAm + ADPm + Pim | 0 MCCC1 |
| MGCOAm + H2Om -> H3MCOAm | 0 HIBCHB |
| H3MCOAm -> ACCOAm + ACTACm | 0 HMGCL |
| MYOACT + ATP -> MYOATP + ACTIN | 0 MYOSA |
| MYOATP + ACTIN -> MYOADPAC | 0 MYOSB |
| MYOADPAC -> ADP + PI + MYOACT + CONTRACT | 0 MYOSC |
| PCRE + ADP -> CRE + ATP | 0 CREATA |
| AMP + H2O -> PI + ADN | 0 CREATB |
| ATP + AMP <-> 2 ADP | 0 CREATC |
| O2 <-> O2m | 0 O2MT |
| 3HB -> 3HBm | 0 HBMT |
| CIT + MALm <-> CITm + MAL | 0 CITMC |
| PYR <-> PYRm + Hm | 0 PYRMC |
| C160CAR + COAm -> C160COAm + CAR | 0 C160CM |
| OMVAL -> OMVALm | 0 HIBCHC |
| OIVAL -> OIVALm | 0 HIBCHD |
| OICAP -> OICAPm | 0 HIBCHE |
| GL <-> GLm | 0 GLMT |
| GL3Pm + FADm -> T3P2m + FADH2m | 0 GPD2 |
| T3P2 + NADH <-> GL3P + NAD | 0 GPD1 |
| GL3P <-> GL3Pm | 0 GL3PMC |
| T3P2 <-> T3P2m | 0 T3P2MC |
| OAm + GLUm <-> ASPm + AKGm | 0 GOT1 |
| OA + GLU <-> ASP + AKG | 0 GOT2 |
| AKG + MALm <-> AKGm + MAL | 0 MALMC |
| ASPm + GLU + H -> Hm + GLUm + ASP | 0 ASPMC |
| GLCxt -> GLC | 0 GLUT4 |
| O2xt -> O2 | 0 O2UP |
| C160Axt + FABP -> C160FP + ALBxt | 0 FAT1 |
| C160FP -> C160 + FABP | 0 FAT2 |
| C180Axt + FABP -> C180FP + ALBxt | 0 FAT3 |
| C180FP -> C180 + FABP | 0 FAT4 |
| C161Axt + FABP -> C161FP + ALBxt | 0 FAT5 |
| C161FP -> C161 + FABP | 0 FAT6 |
| C181Axt + FABP -> C181FP + ALBxt | 0 FAT7 |
| C181FP -> C181 + FABP | 0 FAT8 |
| C182Axt + FABP -> C182FP + ALBxt | 0 FAT9 |
| C182FP -> C182 + FABP | 0 FAT10 |

TABLE 4-continued

Metabolic Reaction for Muscle Cells

| Reaction | Rxt Name |
| --- | --- |
| C204Axt + FABP -> C204FP + ALBxt | 0 FAT11 |
| C204FP -> C204 + FABP | 0 FAT12 |
| PYRxt + HEXT <-> PYR + H | 0 PYRUP |
| LACxt + HEXT <-> LAC + HEXT | 0 LACUP |
| H <-> HEXT | 0 HextUP |
| CO2 <-> CO2m | 0 CO2MT |
| H2O <-> H2Om | 0 H2OMT |
| ATP + AC + COA -> AMP + PPI + ACCOA | 0 FLJ2 |
| C160CAR <-> C160CARm | 0 C160MT |
| CARm <-> CAR | 0 CARMT |
| CO2xt <-> CO2 | 0 CO2UP |
| H2Oxt <-> H2O | 0 H2OUP |
| PIxt + HEXT <-> HEXT + PI | 0 PIUP |
| <-> GLCxt | 0 GLCexR |
| <-> PYRxt | 0 PYRexR |
| <-> CO2xt | 0 CO2exR |
| <-> O2xt | 0 O2exR |
| <-> PIxt | 0 PIexR |
| <-> H2Oxt | 0 H2OexR |
| <-> LACxt | 0 LACexR |
| <-> C160Axt | 0 C160AexR |
| <-> C161Axt | 0 C161AexR |
| <-> C180Axt | 0 C180AexR |
| <-> C181Axt | 0 C181AexR |
| <-> C182Axt | 0 C182AexR |
| <-> C20Axt | 0 C204AexR |
| <-> ALBxt | 0 ALBexR |
| <-> 3HB | 0 HBexR |
| <-> GLYCOGEN | 0 GLYex |
| <-> PCRE | 0 PCREex |
| <-> TAGLYm | 0 TAGmex |
| <-> ILE | 0 ILEex |
| <-> VAL | 0 VALex |
| <-> CRE | 0 CREex |
| <-> ADN | 0 ADNex |
| <-> PI | 0 PIex |

What is claimed is:

1. A computer readable medium or media having stored thereon computer-implemented instructions suitably programmed to cause a processor to perform the computer executable steps of:
   (a) providing a stoichiometric matrix having rows and columns of elements that correspond to stoichiometric coefficients of a plurality of *Homo sapiens* reactions between a plurality of *Homo sapiens* reactants,
      wherein each of said *Homo sapiens* reactions comprises a reactant identified as a substrate of the reaction and a reactant identified as a product of the reaction, the stoichiometric coefficient relating said substrate and said product,
      wherein at least one of said *Homo sapiens* reactions is annotated to indicate an associated gene encoding a macromolecule that performs said reaction and wherein a plurality of chemically and electrochemically balanced *Homo sapiens* reactions are assigned to a plurality of different membranous compartments;
   (b) providing a gene database comprising information characterizing said associated gene;
   (c) providing a constraint set for said plurality of *Homo sapiens* reactions, the constraint set representing an upper or lower boundary condition of flux through each of the *Homo sapiens* reactions described in the stoichiometric matrix;
   (d) defining an objective function to be a linear combination of fluxes through the *Homo sapiens* reactions described in the stoichiometric matrix that optimizes cell growth, reproduction, apoptosis, energy production, production of a particular compound, or a mechanical property;
   (e) determining at least one steady state flux distribution for said plurality of chemically and electrochemically balanced *Homo sapiens* reactions across said plurality of different membranous compartments by (i) identifying a plurality of flux vectors that each satisfy a steady state condition for the stoichiometric matrix and satisfy the constraint set and (ii) identifying at least one linear combination of the flux vectors that minimizes or maximizes the objective function, wherein said at least one steady state flux distribution is predictive of a *Homo sapiens* physiological function at steady state; and
   (f) providing output to a user of said at least one steady state flux distribution determined in step (e).

2. The computer readable medium or media of claim 1, wherein said plurality of *Homo sapiens* reactions comprises at least one reaction from a peripheral metabolic pathway.

3. The computer readable medium or media of claim 2, wherein said peripheral metabolic pathway is selected from the group consisting of amino acid biosynthesis, amino acid degradation, purine biosynthesis, pyrimidine biosynthesis, lipid biosynthesis, fatty acid metabolism, cofactor biosynthesis and transport processes.

4. The computer readable medium or media of claim 1, wherein said *Homo sapiens* physiological function is selected from the group consisting of growth, energy production, redox equivalent production, biomass production, production of biomass precursors, production of a protein, production of an amino acid, production of a purine, production of a pyrimidine, production of a lipid, production of a fatty acid, production of a cofactor, transport of a metabolite, and consumption of carbon, nitrogen, sulfur, phosphate, hydrogen or oxygen.

5. The computer readable medium or media of claim 1, wherein said *Homo sapiens* physiological function is selected from the group consisting of degradation of a protein, degradation of an amino acid, degradation of a purine, degradation of a pyrimidine, degradation of a lipid, degradation of a fatty acid and degradation of a cofactor.

6. The computer readable medium or media of claim 1, wherein a first substrate or product in said plurality of *Homo sapiens* reactions is assigned to a first compartment and a second substrate or product in said plurality of *Homo sapiens* reactions is assigned to a second compartment.

7. The computer readable medium or media of claim 1, wherein a plurality of said *Homo sapiens* reactions is annotated to indicate a plurality of associated genes and wherein said gene database comprises information characterizing said plurality of associated genes.

8. The computer readable medium or media of claim 1, wherein at least one of said *Homo sapiens* reactions is a regulated reaction and wherein said constraint set includes a variable boundary condition for said regulated reaction.

9. The computer readable medium or media of claim 8, wherein said variable boundary condition is dependent upon an outcome of at least one reaction in said stoichiometric matrix.

10. The computer readable medium or media of claim 8, wherein said variable boundary condition is dependent upon an outcome of a regulatory event.

11. The computer readable medium or media of claim 8, wherein said variable boundary condition is dependent upon time.

12. The computer readable medium or media of claim 8, wherein said variable boundary condition is dependent upon the presence of a biochemical reaction network participant.

13. The computer readable medium or media of claim 12, wherein said participant is selected from the group consisting of a substrate, product, reaction, protein, macromolecule, enzyme and gene.

14. The computer readable medium or media of claim 8, wherein a plurality of said reactions are regulated reactions and said constraint set comprises variable boundary conditions for said regulated reactions.

15. The computer readable medium or media of claim 1, wherein the stoichiometric matrix includes rows and columns of elements that correspond to stoichiometric coefficients of a plurality of *Homo sapiens* reactions between a plurality of *Homo sapiens* skeletal muscle cell reactants, and
wherein said at least one flux distribution is predictive of *Homo sapiens* skeletal muscle cell energy production.

16. A method for predicting a *Homo sapiens* physiological function, the method comprising:
(a) providing a stoichiometric matrix having rows and columns of elements that correspond to stoichiometric coefficients of a plurality of *Homo sapiens* reactions between a plurality of *Homo sapiens* reactants,
wherein each of said *Homo sapiens* reactions comprises a reactant identified as a substrate of the reaction and a reactant identified as a product of the reaction, the stoichiometric coefficient relating said substrate and said product,
wherein at least one of said *Homo sapiens* reactions is annotated to indicate an associated gene encoding a macromolecule that performs said reaction and wherein a plurality of chemically and electrochemically balanced *Homo sapiens* reactions are assigned to a plurality of different membranous compartments;
(b) providing a gene database comprising information characterizing said associated gene;
(c) providing a constraint set for said plurality of *Homo sapiens* reactions, the constraint set representing an upper or lower boundary condition of flux through each of the *Homo sapiens* reactions described in the stoichiometric matrix;
(d) defining an objective function to be a linear combination of fluxes through the *Homo sapiens* reactions described in the stoichiometric matrix that optimizes cell growth, reproduction, apoptosis, energy production, production of a particular compound, or a mechanical property;
(e) determining at least one steady state flux distribution for said plurality of chemically and electrochemically balanced *Homo sapiens* reactions across said plurality of different membranous compartments by (i) identifying a plurality of flux vectors that each satisfy a steady state condition for the stoichiometric matrix and satisfy the constrain set and (ii) identifying at least one linear combination of the flux vectors that minimizes or maximizes said objective function, wherein said at least one steady state flux distribution is predictive of a *Homo sapiens* physiological function; and
(f) providing output to a user of said at least one steady state flux distribution determined ins step (e).

17. The method of claim 16, wherein said plurality of *Homo sapiens* reactions comprises at least one reaction from a peripheral metabolic pathway.

18. The method of claim 17, wherein said peripheral metabolic pathway is selected from the group consisting of amino acid biosynthesis, amino acid degradation, purine biosynthesis, pyrimidine biosynthesis, lipid biosynthesis, fatty acid metabolism, cofactor biosynthesis and transport processes.

19. The method of claim 16, wherein said *Homo sapiens* physiological function is selected from the group consisting of growth, energy production, redox equivalent production, biomass production, production of biomass precursors, production of a protein, production of an amino acid, production of a purine, production of a pyrimidine, production of a lipid, production of a fatty acid, production of a cofactor, transport of a metabolite, and consumption of carbon, nitrogen, sulfur, phosphate, hydrogen or oxygen.

20. The method of claim 16, wherein said *Homo sapiens* physiological function is selected from the group consisting of glycolysis, the TCA cycle, pentose phosphate pathway, respiration, biosynthesis of an amino acid, degradation of an amino acid, biosynthesis of a purine, biosynthesis of a pyrimidine, biosynthesis of a lipid, metabolism of a fatty acid, biosynthesis of a cofactor, transport of a metabolite and metabolism of a carbon source, nitrogen source, oxygen source, phosphate source, hydrogen source or sulfur source.

21. The method of claim 16, further comprising:
(g) providing a modified stoichiometric matrix, wherein said modified stoichiometric matrix comprises at least one row of elements corresponding to stoichiometric coefficients of at least one added reaction, compared to the stoichiometric matrix of step (a), and
(h) determining at least one modified steady state flux distribution by (i) identifying a modified plurality of flux vectors that satisfy the steady state condition for the modified stoichiometric matrix and (ii) identifying at least one linear combination of the modified flux vectors that minimizes or maximizes said objective function, thereby predicting a modified *Homo sapiens* physiological function.

22. The method of claim 21, further comprising identifying at least one participant in said at least one added reaction.

23. The method of claim 22, wherein said identifying at least one participant comprises associating a *Homo sapiens* protein with said at least one reaction.

24. The method of claim 23, further comprising identifying at least one gene that encodes said protein.

25. The method of claim 22, further comprising identifying at least one compound that alters the activity or amount of said at least one participant, thereby identifying a candidate drug or agent that alters a *Homo sapiens* physiological function.

26. The method of claim 16, further comprising:
(e) providing a modified data structure, wherein said modified data structure lacks at least one reaction compared to the data structure of part (a), and
(f) determining at least one flux distribution that minimizes or maximizes said objective function when said constraint set is applied to said modified data structure, thereby predicting a *Homo sapiens* physiological function.

27. The method of claim 26, further comprising identifying at least one participant in said at least one reaction.

28. The method of claim 27, wherein said identifying at least one participant comprises associating a *Homo sapiens* protein with said at least one reaction.

29. The method of claim 28, further comprising identifying at least one gene that encodes said protein that performs said at least one reaction.

30. The method of claim 27, further comprising identifying at least one compound that alters the activity or amount of said at least one participant, thereby identifying a candidate drug or agent that alters a *Homo sapiens* physiological function.

31. The method of claim 16, further comprising:
(g) providing a modified constraint set, wherein said modified constraint set comprises a changed upper or lower boundary condition of flux through at least one reaction compared to the upper or lower boundary condition of flux through that reaction in step (c), and
(h) determining at least one modified steady state flux distribution by (i) identifying a modified plurality of flux vectors that satisfy the steady state condition for the stoichiometric matrix and satisfy the modified constraint set and (ii) identifying at least one linear combination of the modified flux vectors that minimizes or maximizes said objective function, thereby predicting a modified *Homo sapiens* physiological function.

32. The method of claim 31, further comprising identifying at least one participant in said at least one reaction.

33. The method of claim 32, wherein said identifying at least one participant comprises associating a *Homo sapiens* protein with said at least one reaction.

34. The method of claim 33, further comprising identifying at least one gene that encodes said protein.

35. The method of claim 32, further comprising identifying at least one compound that alters the activity or amount of said at least one participant, thereby identifying a candidate drug or agent that alters a *Homo sapiens* physiological function.

36. The method of claim 16, wherein the gene database relates one or more reactions in said data structure with one or more genes or proteins in *Homo sapiens*.

37. The method of claim 16, wherein at least one of said *Homo sapiens* reactions is a regulated reaction and wherein said constraint set includes a variable boundary condition for said regulated reaction.

38. The method of claim 37, wherein said variable boundary condition changes in response to an outcome of at least one reaction in said stoichiometric matrix.

39. The method of claim 37, wherein said variable boundary condition changes in response to an outcome of a regulatory event.

40. The method of claim 37, wherein said variable boundary condition changes in response to time.

41. The method of claim 37, wherein said variable boundary condition changes in response to the presence of a biochemical reaction network participant.

42. The method of claim 41, wherein said participant is selected from the group consisting of a substrate, product, reaction, enzyme, protein, macromolecule and gene.

43. The method of claim 37, wherein a plurality of said reactions are regulated reactions and said constraint set comprises variable boundary conditions for said regulated reactions.

44. The method of claim 16, wherein the stoichiometric matrix includes rows and columns of elements that correspond to stoichiometric coefficients of a plurality of *Homo sapiens* reactions between a plurality of *Homo sapiens* skeletal muscle cell reactants wherein said at least one steady state flux distribution is predictive of *Homo sapiens* skeletal muscle cell energy production.

\* \* \* \* \*

UNITED STATES PATENT AND TRADEMARK OFFICE
CERTIFICATE OF CORRECTION

PATENT NO. : 8,229,673 B2  Page 1 of 1
APPLICATION NO. : 10/402854
DATED : July 24, 2012
INVENTOR(S) : Bernhard O. Palsson et al.

It is certified that error appears in the above-identified patent and that said Letters Patent is hereby corrected as shown below:

On the title page, Item [75] replace the inventor information to read:

Bernhard O. Palsson, La Jolla, CA (US);

Imandokht Famili, San Diego, CA (US);

Markus W. Covert, San Diego, CA (US);

Christophe H. Schilling, San Diego, CA (US).

Signed and Sealed this
Fourth Day of September, 2012

David J. Kappos
*Director of the United States Patent and Trademark Office*